US008470561B2

(12) United States Patent
Kobilka

(10) Patent No.: US 8,470,561 B2
(45) Date of Patent: Jun. 25, 2013

(54) GPCR COMPRISING AN IC2 INSERTION

(75) Inventor: Brian Kobilka, Palo Alto, CA (US)

(73) Assignee: ConfometRX Inc., Palo Alto, CA (US)

( * ) Notice: Subject to any disclaimer, the term of this patent is extended or adjusted under 35 U.S.C. 154(b) by 0 days.

(21) Appl. No.: 13/220,513

(22) Filed: Aug. 29, 2011

(65) Prior Publication Data

US 2012/0219992 A1 Aug. 30, 2012

Related U.S. Application Data

(60) Provisional application No. 61/378,332, filed on Aug. 30, 2010.

(51) Int. Cl.
*C12P 21/04* (2006.01)
*C07K 14/00* (2006.01)

(52) U.S. Cl.
USPC .......................................... 435/69.7; 530/350

(58) Field of Classification Search
None
See application file for complete search history.

(56) References Cited

U.S. PATENT DOCUMENTS

| | | | |
|---|---|---|---|
| 8,260,596 | B2 | 9/2012 | Kobilka et al. |
| 2003/0129649 | A1 | 7/2003 | Kobilka et al. |
| 2003/0198976 | A1 | 10/2003 | Feder et al. |
| 2006/0188964 | A1 | 8/2006 | Mancia et al. |
| 2007/0031832 | A1 | 2/2007 | Watt et al. |
| 2007/0122881 | A1 | 5/2007 | Surber |
| 2009/0118474 | A1 | 5/2009 | Kobilka et al. |
| 2011/0031438 | A1 | 2/2011 | Stevens et al. |
| 2011/0130543 | A1 | 6/2011 | Stevens et al. |

FOREIGN PATENT DOCUMENTS

| | | |
|---|---|---|
| WO | WO 03/000855 | 1/2003 |
| WO | WO 2008/068534 | 6/2008 |
| WO | WO 2009/051769 | 4/2009 |
| WO | WO 2009/055509 | 4/2009 |
| WO | WO 2009/055512 | 4/2009 |
| WO | WO2013021206 | 2/2013 |

OTHER PUBLICATIONS

Ferraguti et al, "Metabotropic Glutamate 1 Receptor: Current Concepts and Perspectives", Pharmacological Reviews, 2008, 60(4):536-581.*
Bell; et al., "Comparison of the Crystal Structure of Bacteriophase T4 Lysozyme at Low, Medium, and High Ionic Strengths", Proteins: Structure, Function, and Genetics (1991), 10:10-21.
Brauner-Osborne; et al., "Structure, pharmacology and therapeutic prospects of family C G-protein coupled receptors", Curr Drug Targets (2007), 8:169-184.
Byrne; et al., "Fusion protein approach to improve the crystal quality of cytochrome bo3 ubiquinol oxidase from *Esscherichia coli*", Bioenergetics (2000), 1459(2-3):449-455.
Cheng; et al., "Kinetics and Equilibria of Lysozyme Precipitation and Crystallization in Concentrated Ammonium Sulfate Solutions", Biotechnology and Bioengineering (2006), 94(1):177-188.

Cherezov; et al., "High-Resolution Crystal Structure of an Engineered Human beta2-Adrenergic G Protein Coupled Receptor", Science (2007), 318(5854):1258-65.
Conn, et al., "Allosteric modulators of GPCRs: a novel approach for the treatment of CNS disorders", Nat Rev Drug Discov (2009), 8:41-54.
Engel; et al., "Insertion of carrier proteins into hydrophilic loops of the *Escherichia coli* lactose permease", Biochemica et Biophysica Acta (2002), 1564:38-46.
Espitalier; et al., "Mechanism of formation of lysozyme crystals in concentrated ammonium sulfate solution from concentration profiles and equilibria: Influence of the 2nd osmotic virial coefficient", Powder Technology (2009), 190:112-117.
Evrard; et al., "Crystal Structure of the Lysozyme from Bacteriophage Lambda and its Relationship with V and C-type Lysozymes", J. Mol. Biol. (1998), 276:151-164.
Forsythe; et al., "Crystallization of chicken egg-white lysozyme from ammonium sulfate", Acta Cryst. (1997), D53:795-797.
Geiser et ai, "Bacteriorhodopsin chimeras containing the third cytoplasmic loop of bovine rhodopsin activate transducin for GTP/GDP exchange Protein", Science (2006),15:1679-90.
Goudet, et al., "Heptahelical domain of metabotropic glutamate receptor 5 behaves like rhodopsin-like receptors" Proc Natl Acad Sci (2004), 6:378-383.
Harada; et al., "Preliminary X-ray Crystallographic Study of Lysozyme Produced by *Streptomyces globisporus*", J. Mol. Biol. (1989), 207:851-852.
Hoffman; et al., "A FLAsH-based FRET approach to determine G protein-coupled receptor activation in living cells", Nature Methods (2005), 2(3):171-6.
International Search Report dated Feb. 2, 2009 of PCT/US2008/011838.
International Search Report dated Jan. 27, 2012 of PCT/US2011/049593.
Jaakola et al., "The 2.6 angstrom crystal structure of a human A2A adenosine receptor bound to an antagonist", Science (2008), 322:1211-1217.
Kim et al., Light-driven activation of beta 2-adrenergic receptor signaling by a chimeric rhodopsin containing the beta 2-adrenergic receptor cytoplasmic loops', Biochemistry (2005), 44:2284-92.
Kobilka; et al., "Conformational complexity of G-protein-coupled receptors", Trends in Pharmacological Sciences (2007),28(8):397-406.
Lan; et al., "An Intracellular Loop 2 Amino Acid Residue Determines Differential Binding of Arrestin to the Dopamine D2 and D3 Receptors", Mol Pharmacol (2009), 75:19-26.
Lapinsh; et al., "Classification of G-protein coupled receptors by alignment-independent extraction of principal chemical properties of primary amino acid sequences", Protein Science (2002), 11:795-805.
Lyne; et al., "Preliminary Crystallographic Examination of a Novel Fungal Lysozyme from Chalaropsis", The Journal of Biological Chemistry (1990), 265(12):6928-6930.

(Continued)

*Primary Examiner* — Suzanne M Noakes
(74) *Attorney, Agent, or Firm* — James S. Keddie; Bozicevic, Field & Francis, LLP

(57) ABSTRACT

Certain embodiments provide a method for crystallizing a GPCR. The method may employ a fusion protein comprising, from N-terminus to C-terminus: a) a first portion of a family C G-protein coupled receptor (GPCR), wherein the first portion comprises the TM1, TM2 and TM3, regions of the GPCR; b) a stable, folded protein insertion; and c) a second portion of the GPCR, wherein the second portion comprises the TM4, TM5 TM6 and TM7 regions of the GPCR.

15 Claims, 12 Drawing Sheets

OTHER PUBLICATIONS

Marana; et al., "Crystallization, data collection and phasing of two digestive lysozymes from *Musca domestica*", Acta Cryst. (2006), F62:750-752.

Prive, "Fusion Proteins as Tools for Crystallization: the Lactose Permease from *Escherichia coli*", Acta Cryst. (1994), D50:375-379.

Prive; et al., "Engineering the Lac Permease for Purification and Crystallization", Journal of Bioenergetics and Biomembranes (1996), 28(1):29-34.

Rasmussen; et al., "Crystal structure of the human beta2 adrenergic G-protein-coupled receptor", Nature (2007), 450(7168):383-7.

Remington; et al., "Structure of the Lysozyme from Bacteriophage T4: An Electron Density Map at 2 4 A Resolution", J. Mol. Biol. (1978), 118:81-98.

Ries-Kautt; et al., "Crystallization of Previously Desalted Lysozyme in the Presence of Sulfate Ions", Acta Cryst. (1994), D50:366-369.

Ries-Kautt; et al., "Relative Effectiveness of Various Ions on the Solubility and Crystal Growth of Lysozyme", The Journal of Biological Chemistry (1989), 264(2):745-748.

Rosenbaum; et al., "GPCR Engineering Yields High-Resolution Structural Insights into beta2-Adrenergic Receptor Function", Science (2007), 318:(5854):1266-73.

Strynadka; et al., "Lysozyme: A model enzyme in protein crystallography", EXS. (1996), 75:185-222.

Topiol; et al., "X-ray structure breakthroughs in the GPCR transmembrane region", Biochemical Pharmacology (2009),78(1):11-20.

Tumova et al., "Insight into the mechanism of dopamine D1-like receptor activation. Evidence for a molecular interplay between the third extracellular loop and the cytoplasmic tail", J. Biol. Chem. (2003),278:8146-53.

U.S. Appl. No. 60/999,951, filed Oct. 22, 2007, 79pgs.
U.S. Appl. No. 61/000,325, filed Oct. 24, 2007, 89pgs.
U.S. Appl. No. 61/060,107, filed Jun. 9, 2008, 108pgs.
U.S. Appl. No. 61/194,961, filed Oct. 1, 2008, 173pgs.

Vilardaga; et al., "Differential Conformational Requirements for Activation of G Proteins and the Regulatory Proteins Arrestin and G Protein-coupled Receptor Kinase in the G Protein-coupled Receptor for Parathyroid Hormone (PTH)/PTH-related Protein", The Journal of Biological Chemistry (2001), 276(36):33435-33443.

Vilardaga; et al., "Measurement of the millisecond activation switch of G protein-coupled receptors in living cells", Nature Biotechnology (2003), 21(7):807-812.

Wang; et al., "Identification of a domain in the angiotensin II type 1 receptor determining G-q coupling by the use of receptor chimeras", Journal of Biological Chemistry (1995),270(28):16677-16682.

Wellendorph, et al., "Molecular basis for amino acid sensing by family C G-protein-coupled receptors", Br J Pharmacol, (2009), 156:869-884.

Wess et al., "Identification of a small intracellular region of the muscarinic m3 receptor as a determinant of selective coupling to PI turnover", FEBS Lett. (1989), 258:133-6.

Wong et al., "Chimeric muscarinic cholinergic: beta-adrenergic receptors that activate Gs in response to muscarinic agonists", J. Biol. Chem. (1990), 265:6219-24.

Yamashita et al., "Distinct roles of the second and third cytoplasmic loops of bovine rhodopsin in G protein activation", J. Biol. Chem. (2000), 275:34272-9.

Yao; et al., "Crystallization and Preliminary X-Ray Structure Analysis of Pigeon Egg-White Lysozyme", J. Biochem. (1992), 111:1-3.

Yu; et al., "Global chimeric exchanges within the intracellular face of the bradykinin B2 receptor with corresponding angiotensin II type Ia receptor regions: Generation of fully functional hybrids showing characteristic signaling of the ATIa receptor", Journal of Cellular Biochemistry (2002),85(4):809-819.

Zhang; et al., "Structure modeling of all identified G protein-coupled receptors in the human genome", PLOS Computational Biology (2006), 2(2):0088-0099.

Pin, et al., "Domains involved in the specificity of G protein activation in phospholipase C-coupled metabotropic glutamate receptors.", The EMBO Journal vol. 13 No. 2 pp. 342-348, 1994.

* cited by examiner mGluR5 Rock 10 protein sequence (SEQ ID NO:1)

DYKDDDDAAA*PVQYLRWGDPEPIAAVVFACLGLLATLFVTVIFIIYRDTPV*
*VKSSSRELCYIILAGICLGYLCTFCLIAKPKQIYCYLQRIGIGLSPAMSYS*
*ALVTKTNRIARILAGSKK*nifemlrideglrlkiykdtegyytigighllt
kspslnaakseldkaigrntngvitkdeaeklfnqdvdaavrgilrnaklk
pvydsldavrraalinmvfqmgetgvagftnslrmlqqkrwdeaavnlaks
rwynqtpnrakrvittfrtgtwday*KICTKKPRFMSACAQLVIAFILICIQ*
*LGIIVALFIMEPPDIMHDYPSIREVYLICNTTNLGVVTPLGYNGLLILSCT*
*FYAFKTRNVPANFNEAKYIAFTMYTTCIIWLAFVPIYFGSNYKIITMCFSV*
*SLSATVALGCMFVPKVYIILAKPERNVRSAFTTSTVVRMHVGDGKSSSAAS*
*RSSSLVNL*HHHHHH*

XXXX: Flag tag
*XXXX*: mGluR5 HD
lowercase: T4L inserted between K677 and K678

FIG. 3

>sp|Q13255|GRM1_HUMAN Metabotropic glutamate receptor 1
OS=Homo sapiens GN=GRM1 PE=1 SV=2 (SEQ ID NO:7)
MVGLLLFFFPAIFLEVSLLPRSPGRKVLLAGASSQRSVARMDGDVIIGALFSVHHQPPA
EKVPERKCGEIREQYGIQRVEAMFHTLDKINADPVLLPNITLGSEIRDSCWHSSVALEQ
SIEFIRDSLISIRDEKDGINRCLPDGQSLPPGRTKKPIAGVIGPGSSSVAIQVQNLLQL
FDIPQIAYSATSIDLSDKTLYKYFLRVVPSDTLQARAMLDIVKRYNWTYVSAVHTEGNY
GESGMDAFKELAAQEGLCIAHSDKIYSNAGEKSFDRLLRKLRERLPKARVVVCFCEGMT
VRGLLSAMRRLGVVGEFSLIGSDGWADRDEVIEGYEVEANGGITIKLQSPEVRSFDDYF
LKLRLDTNTRNPWFPEFWQHRFQCRLPGHLLENPNFKRICTGNESLEENYVQDSKMGFV
INAIYAMAHGLQNMHHALCPGHVGLCDAMKPIDGSKLLDFLIKSSFIGVSGEEVWFDEK
GDAPGRYDIMNLQYTEANRYDYVHVGTWHEGVLNIDDYKIQMNKSGVVRSVCSEPCLKG
QIKVIRKGEVSCCWICTACKENEYVQDEFTCKACDLGWWPNADLTGCEPIPVRYLEWSN
IESIIAIAFSCLGILVTLFVTLIFVLYRDTPVVKSSSRELCYIILAGIFLGYVCPFTLI
AKPTTTSCYLQRLLVGLSSAMCYSALVTKTNRIARILAGSKKKICTRKPRFMSAWAQVI
▲
IASILISVQLTLVVTLIIMEPPMPILSYPSIKEVYLICNTSNLGVVAPLGYNGLLIMSC
TYYAFKTRNVPANFNEAKYIAFTMYTTCIIWLAFVPIYFGSNYKIITTCFAVSLSVTVA
LGCMFTPKMYIIIAKPERNVRSAFTTSDVVRMHVGDGKLPCRSNTFLNIFRRKKAGAGN
ANSNGKSVSWSEPGGGQVPKGQHMWHRLSVHVKTNETACNQTAVIKPLTKSYQGSGKSL
TFSDTSTKTLYNVEEEEDAQPIRFSPPGSPSMVVHRRVPSAATTPPLPPHLTAEETPLF
LAEPALPKGLPPPLQQQQQPPPQQKSLMDQLQGVVSNFSTAIPDFHAVLAGPGGPGNGL
RSLYPPPPPPQHLQMLPLQLSTFGEELVSPPADDDDDSERFKLLQEYVYEHEREGNTEE
DELEEEEEDLQAASKLTPDDSPALTPPSPFRDSVASGSSVPSSPVSESVLCTPPNVSYA
SVILRDYKQSSSTL >sp|Q14416|GRM2_HUMAN Metabotropic glutamate receptor 2
OS=Homo sapiens GN=GRM2 PE=2 SV=2 (SEQ ID NO:8)
MGSLLALLALLLLWGAVAEGPAKKVLTLEGDLVLGGLFPVHQKGGPAEDCGPVNEHRGI
QRLEAMLFALDRINRDPHLLPGVRLGAHILDSCSKDTHALEQALDFVRASLSRGADGSR
HICPDGSYATHGDAPTAITGVIGGSYSDVSIQVANLLRLFQIPQISYASTSAKLSDKSR
YDYFARTVPPDFFQAKAMAEILRFFNWTYVSTVASEGDYGETGIEAFELEARARNICVA
TSEKVGRAMSRAAFEGVVRALLQKPSARVAVLFTRSEDARELLAASQRLNASFTWVASD
GWGALESVVAGSEGAAEGAITIELASYPISDFASYFQSLDPWNNSRNPWFREFWEQRFR
CSFRQRDCAAHSLRAVPFEQESKIMFVVNAVYAMAHALHNMHRALCPNTTRLCDAMRPV
NGRRLYKDFVLNVKFDAPFRPADTHNEVRFDRFGDGIGRYNIFTYLRAGSGRYRYQKVG
YWAEGLTLDTSLIPWASPSAGPLPASRCSEPCLQNEVKSVQPGEVCCWLCIPCQPYEYR
LDEFTCADCGLGYWPNASLTGCFELPQEYIRWGDAWAVGPVTIACLGALATLFVLGVFV
RHNATPVVKASGRELCYILLGGVFLCYCMTFIFIAKPSTAVCTLRRLGLGTAFSVCYSA
LLTKTNRIARIFGGAREGAQRPRFISPASQVAICLALISGQLLIVVAWLVVEAPGTGKE
▲
TAPERREVVTLRCNHRDASMLGSLAYNVLLIALCTLYAFKTRKCPENFNEAKFIGFTMY
TTCIIWLAFLPIFYVTSSDYRVQTTTMCVSVSLSGSVVLGCLFAPKLHIILFQPQKNVV
SHRAPTSRFGSAAARASSSLGQGSGSQFVPTVCNGREVVDSTTSSL

FIG. 4A

\>sp|Q14832|GRM3_HUMAN Metabotropic glutamate receptor 3
OS=Homo sapiens GN=GRM3 PE=2 SV=2 (SEQ ID NO:9)
MKMLTRLQVLTLALFSKGFLLSLGDHNFLRREIKIEGDLVLGGLFPINEKGTGTEECGR
INEDRGIQRLEAMLFAIDEINKDDYLLPGVKLGVHILDTCSRDTYALEQSLEFVRASLT
KVDEAEYMCPDGSYAIQENIPLLIAGVIGGSYSSVSIQVANLLRLFQIPQISYASTSAK
LSDKSRYDYFARTVPPDFYQAKAMAEILRFFNWTYVSTVASEGDYGETGIEAFEQEARL
RNICIATAEKVGRSNIRKSYDSVIRELLQKPNARVVVLFMRSDDSRELIAAASRANASF
TWVASDGWGAQESIIKGSEHVAYGAITLELASQPVRQFDRYFQSLNPYNNHRNPWFRDF
WEQKFQCSLQNKRNHRRVCDKHLAIDSSNYEQESKIMFVVNAVYAMAHALHKMQRTLCP
NTTKLCDAMKILDGKKLYKDYLLKINFTAPFNPNKDADSIVKFDTFGDGMGRYNVFNFQ
NVGGKYSYLKVGHWAETLSLDVNSIHWSRNSVPTSQCSDPCAPNEMKNMQPGDVCCWIC
IPCEPYEYLADEFTCMDCGSGQWPTADLTGCYDLPEDYIRWEDAWAIGPVTIACLGFMC
TCMVVTVFIKHNNTPLVKASGRELCYILLFGVGLSYCMTFFFIAKPSPVICALRRLGLG
SSFAICYSALLTKTNCIARIFDGVKNGAQRPKFISPSSQVFICLGLILVQIVMVSVWLI
▲
LEAPGTRRYTLAEKRETVILKCNVKDSSMLISLTYDVILVILCTVYAFKTRKCPENFNE
AKFIGFTMYTTCIIWLAFLPIFYVTSSDYRVQTTTMCISVSLSGFVVLGCLFAPKVHII
LFQPQKNVVTHRLHLNRFSVSGTGTTYSQSSASTYVPTVCNGREVLDSTTSSL \>sp|Q14833|GRM4_HUMAN Metabotropic glutamate receptor 4
OS=Homo sapiens GN=GRM4 PE=1 SV=1 (SEQ ID NO:10)
MPGKRGLGWWWARLPLCLLLSLYGPWMPSSLGKPKGHPHMNSIRIDGDITLGGLFPVHG
RGSEGKPCGELKKEKGIHRLEAMLFALDRINNDPDLLPNITLGARILDTCSRDTHALEQ
SLTFVQALIEKDGTEVRCGSGGPPIITKPERVVGVIGASGSSVSIMVANILRLFKIPQI
SYASTAPDLSDNSRYDFFSRVVPSDTYQAQAMVDIVRALKWNYVSTVASEGSYGESGVE
AFIQKSREDGGVCIAQSVKIPREPKAGEFDKIIRRLLETSNARAVIIFANEDDIRRVLE
AARRANQTGHFFWMGSDSWGSKIAPVLHLEEVAEGAVTILPKRMSVRGFDRYFSSRTLD
NNRRNIWFAEFWEDNFHCKLSRHALKKGSHVKKCTNRERIGQDSAYEQEGKVQFVIDAV
YAMGHALHAMHRDLCPGRVGLCPRMDPVDGTQLLKYIRNVNFSGIAGNPVTFNENGDAP
GRYDIYQYQLRNDSAEYKVIGSWTDHLHLRIERMHWPGSGQQLPRSICSLPCQPGERKK
TVKGMPCCWHCEPCTGYQYQVDRYTCKTCPYDMRPTENRTGCRPIPIIKLEWGSPWAVL
PLFLAVVGIAATLFVVITFVRYNDTPIVKASGRELSYVLLAGIFLCYATTFLMIAEPDL
GTCSLRRIFLGLGMSISYAALLTKTNRIYRIFEQGKRSVSAPRFISPASQLAITFSLIS
▲
LQLLGICVWFVVDPSHSVVDFQDQRTLDPRFARGVLKCDISDLSLICLLGYSMLLMVTC
TVYAIKTRGVPETFNEAKPIGFTMYTTCIVWLAFIPIFFGTSQSADKLYIQTTTLTVSV
SLSASVSLGMLYMPKVYIILFHPEQNVPKRKRSLKAVVTAATMSNKFTQKGNFRPNGEA
KSELCENLEAPALATKQTYVTYTNHAI \>sp|P41594|GRM5_HUMAN Metabotropic glutamate receptor 5
OS=Homo sapiens GN=GRM5 PE=1 SV=2 (SEQ ID NO:11)
MVLLLILSVLLLKEDVRGSAQSSERRVVAHMPGDIIIGALFSVHHQPTVDKVHERKCGA
VREQYGIQRVEAMLHTLERINSDPTLLPNITLGCEIRDSCWHSAVALEQSIEFIRDSLI
SSEEEEGLVRCVDGSSSSFRSKKPIVGVIGPGSSSVAIQVQNLLQLFNIPQIAYSATSM
DLSDKTLFKYFMRVVPSDAQQARAMVDIVKRYNWTYVSAVHTEGNYGESGMEAFKDMSA
KEGICIAHSYKIYSNAGEQSFDKLLKKLTSHLPKARVVACFCEGMTVRGLLMAMRRLGL

FIG. 4B

AGEFLLLGSDGWADRYDVTDGYQREAVGGITIKLQSPDVKWFDDYYLKLRPETNHRNPW
FQEFWQHRFQCRLEGFPQENSKYNKTCNSSLTLKTHHVQDSKMGFVINAIYSMAYGLHN
MQMSLCPGYAGLCDAMKPIDGRKLLESLMKTNFTGVSGDTILFDENGDSPGRYEIMNFK
EMGKDYFDYINVGSWDNGELKMDDDEVWSKKSNIIRSVCSEPCEKGQIKVIRKGEVSCC
WTCTPCKENEYVFDEYTCKACQLGSWPTDDLTGCDLIPVQYLRWGDPEPIAAVVFACLG
LLATLFVTVVFIIYRDTPVVKSSSRELCYIILAGICLGYLCTFCLIAKPKQIY**CYLQRI
GIGLSPAMSYSALVTKTNRIARILAGSKKKICTKKPRFMSACAQLVIAFILICIQLGII**
▲

VALFIMEPPDIMHDYPSIREVYLICNTTNLGVVTPLGYNGLLILSCTFYAFKTRNVPAN
FNEAKYIAFTMYTTCIIWLAFVPIYFGSNYKIITMCFSVSLSATVALGCMFVPKVYIIL
AKPERNVRSAFTTSTVVRMHVGDGKSSSAASRSSSLVNLWKRRGSSGETLRYKDRRLAQ
HKSEIECFTPKGSMGNGGRATMSSSNGKSVTWAQNEKSSRGQHLWQRLSIHINKKENPN
QTAVIKPFPKSTESRGLGAGAGAGGSAGGVGATGGAGCAGAGPGGPESPDAGPKALYDV
AEAEEHFPAPARPRSPSPISTLSHRAGSASRTDDDVPSLHSEPVARSSSSQGSLMEQIS
SVVTRFTANISELNSMMLSTAAPSPGVGAPLCSSYLIPKEIQLPTTMTTFAEIQPLPAI
EVTGGAQPAAGAQAAGDAARESPAAGPEAAAAKPDLEELVALTPPSPFRDSVDSGSTTP
NSPVSESALCIPSSPKYDTLIIRDYTQSSSSL

>sp|O15303|GRM6_HUMAN Metabotropic glutamate receptor 6
OS=Homo sapiens GN=GRM6 PE=1 SV=2 (SEQ ID NO:12)
MARPRRAREPLLVALLPLAWLQAGLARAAGSVRLAGGLTLGGLFPVHARGAAGRACGQ
LKKEQGVHRLEAMLYALDRVNADPELLPGVRLGARLLDTCSRDTYALEQALSFVQALIR
GRGDGDEVGVRCPGGVPPLRPAPPERVVAVVGASASSVSIMVANVLRLFAIPQISYAST
APELSDSTRYDFFSRVVPPDSYQAQAMVDIVRALGWNYVSTLASEGNYGESGVEAFVQI
SREAGGVCIAQSIKIPREPKPGEFSKVIRRLMETPNARGIIIFANEDDIRRVLEAARQA
NLTGHFLWVGSDSWGAKTSPILSLEDVAVGAITILPKRASIDGFDQYFMTRSLENNRRN
IWFAEFWEENFNCKLTSSGTQSDDSTRKCTGEERIGRDSTYEQEGKVQFVIDAVYAIAH
ALHSMHQALCPGHTGLCPAMEPTDGRMLLQYIRAVRFNGSAGTPVMFNENGDAPGRYDI
FQYQATNGSASSGGYQAVGQWAETLRLDVEALQWSGDPHEVPSSLCSLPCGPGERKKMV
KGVPCCWHCEACDGYRFQVDEFTCEACPGDMRPTPNHTGCRPTPVVRLSWSSPWAAPPL
LLAVLGIVATTTVVATFVRYNNTPIVRASGRELSYVLLTGIFLIYAITFLMVAEPGAAV
CAARRLFLGLGTTLSYSALLTKTNRIYRIFEQGKRSVTPPPFISPTSQLVITFSLTSLQ
▲

VVGMIAWLGARPPHSVIDYEEQRTVDPEQARGVLKCDMSDLSLIGCLGYSLLLMVTCTV
YAIKARGVPETFNEAKPIGFTMYTTCIIWLAFVPIFFGTAQSAEKIYIQTTTLTVSLSL
SASVSLGMLYVPKTYVILFHPEQNVQKRKRSLKATSTVAAPPKGEDAEAHK

>sp|Q14831|GRM7_HUMAN Metabotropic glutamate receptor 7
OS=Homo sapiens GN=GRM7 PE=2 SV=1 (SEQ ID NO:13)
MVQLRKLLRVLTLMKFPCCVLEVLLCALAAAARGQEMYAPHSIRIEGDVTLGGLFPVHA
KGPSGVPCGDIKRENGIHRLEAMLYALDQINSDPNLLPNVTLGARILDTCSRDTYALEQ
SLTFVQALIQKDTSDVRCTNGEPPVFVKPEKVVGVIGASGSSVSIMVANILRLFQIPQI
SYASTAPELSDDRRYDFFSRVVPPDSFQAQAMVDIVKALGWNYVSTLASEGSYGEKGVE
SFTQISKEAGGLCIAQSVRIPQERKDRTIDFDRIIKQLLDTPNSRAVVIFANDEDIKQI
LAAAKRADQVGHFLWVGSDSWGSKINPLHQHEDIAEGAITIQPKRATVEGFDAYFTSRT
LENNRRNVWFAEYWEENFNCKLTISGSKKEDTDRKCTGQERIGKDSNYEQEGKVQFVID

FIG. 4C

```
AVYAMAHALHHMNKDLCADYRGVCPEMEQAGGKKLLKYIRNVNFNGSAGTPVMFNKNGD
APGRYDIFQYQTTNTSNPGYRLIGQWTDELQLNIEDMQWGKGVREIPASVCTLPCKPGQ
RKKTQKGTPCCWTCEPCDGYQYQFDEMTCQHCPYDQRPNENRTGCQDIPIIKLEWHSPW
AVIPVFLAMLGIIATIFVMATFIRYNDTPIVRASGRELSYVLLTGIFLCYIITFLMIAK
PDVAVCSFRRVFLGLGMCISYAALLTKTNRIYRIFEQGKK▲SVTAPRLISPTSQLAITSS

LISVQLLGVFIWFGVDPPNIIIDYDEHKTMNPEQARGVLKCDITDLQIICSLGYSILLM
VTCTVYAIKTRGVPENFNEAKPIGFTMYTTCIVWLAFIPIFFGTAQSAEKLYIQTTTLT
ISMNLSASVALGMLYMPKVYIIIFHPELNVQKRKRSFKAVVTAATMSSRLSHKPSDRPN
GEAKTELCENVDPNSPAAKKKYVSYNNLVI

>sp|O00222|GRM8_HUMAN Metabotropic glutamate receptor 8
OS=Homo sapiens GN=GRM8 PE=2 SV=2 (SEQ ID NO:14)
MVCEGKRSASCPCFFLLTAKFYWILTMMQRTHSQEYAHSIRVDGDIILGGLFPVHAKGE
RGVPCGELKKEKGIHRLEAMLYAIDQINKDPDLLSNITLGVRILDTCSRDTYALEQSLT
FVQALIEKDASDVKCANGDPPIFTKPDKISGVIGAAASSVSIMVANILRLFKIPQISYA
STAPELSDNTRYDFFSRVVPPDSYQAQAMVDIVTALGWNYVSTLASEGNYGESGVEAFT
QISREIGGVCIAQSQKIPREPRPGEFEKIIKRLLETPNARAVIMFANEDDIRRILEAAK
KLNQSGHFLWIGSDSWGSKIAPVYQQEEIAEGAVTILPKRASIDGFDRYFRSRTLANNR
RNVWFAEFWEENFGCKLGSHGKRNSHIKKCTGLERIARDSSYEQEGKVQFVIDAVYSMA
YALHNMHKDLCPGYIGLCPRMSTIDGKELLGYIRAVNFNGSAGTPVTFNENGDAPGRYD
IFQYQITNKSTEYKVIGHWTNQLHLKVEDMQWAHREHTHPASVCSLPCKPGERKKTVKG
VPCCWHCERCEGYNYQVDELSCELCPLDQRPNMNRTGCQLIPIIKLEWHSPWAVVPVFV
AILGIIATTFVIVTFVRYNDTPIVRASGRELSYVLLTGIFLCYSITFLMIAAPDTIICS
FRRVFLGLGMCFSYAALLTKTNRIHRIFEQGKK▲SVTAPKFISPASQLVITFSLISVQLL

GVFVWFVVDPPHIIIDYGEQRTLDPEKARGVLKCDISDLSLICSLGYSILLMVTCTVYA
IKTRGVPETFNEAKPIGFTMYTTCIIWLAFIPIFFGTAQSAEKMYIQTTTLTVSMSLSA
SVSLGMLYMPKVYIIIFHPEQNVQKRKRSFKAVVTAATMQSKLIQKGNDRPNGEVKSEL
CESLETNTSSTKTTYISYSNHSI

>sp|P41180|CASR_HUMAN **Extracellular calcium-sensing
receptor** OS=Homo sapiens GN=CASR PE=1 SV=2 (SEQ ID NO:15)
MAFYSCCWVLLALTWHTSAYGPDQRAQKKGDIILGGLFPIHFGVAAKDQDLKSRPESVE
CIRYNFRGFRWLQAMIFAIEEINSSPALLPNLTLGYRIFDTCNTVSKALEATLSFVAQN
KIDSLNLDEFCNCSEHIPSTIAVVGATGSGVSTAVANLLGLFYIPQVSYASSSRLLSNK
NQFKSFLRTIPNDEHQATAMADIIEYFRWNWVGTIAADDDYGRPGIEKFREEAEERDIC
IDFSELISQYSDEEEIQHVVEVIQNSTAKVIVVFSSGPDLEPLIKEIVRRNITGKIWLA
SEAWASSSLIAMPQYFHVVGGTIGFALKAGQIPGFREFLKKVHPRKSVHNGFAKEFWEE
TFNCHLQEGAKGPLPVDTFLRGHEESGDRFSNSSTAFRPLCTGDENISSVETPYIDYTH
LRISYNVYLAVYSIAHALQDIYTCLPGRGLFTNGSCADIKKVEAWQVLKHLRHLNFTNN
MGEQVTFDECGDLVGNYSIINWHLSPEDGSIVFKEVGYYNVYAKKGERLFINEEKILWS
GFSREVPFSNCSRDCLAGTRKGIIEGEPTCCFECVECPDGEYSDETDASACNKCPDDFW
SNENHTSCIAKEIEFLSWTEPFGIALTLFAVLGIFLTAFVLGVFIKFRNTPIVKATNRE
LSYLLLFSLLCCFSSSLFFIGEPQDWTCRLRQPAFGISFVLCISCILVKTNRVLLVFEA
KI▲PTSFHRKWWGLNLQFLLVFLCTFMQIVICVIWLYTAPPSSYRNQELEDEIIFITCHE
```

FIG. 4D

GSLMALGFLIGYTCLLAAICFFFAFKSRKLPENFNEAKFITFSMLIFFIVWISFIPAYA
STYGKFVSAVEVIAILAASFGLLACIFFNKIYIILFKPSRNTIEEVRCSTAAHAFKVAA
RATLRRSNVSRKRSSSLGGSTGSTPSSSISSKSNSEDPFPQPERQKQQQPLALTQQEQQ
QQPLTLPQQQRSQQQPRCKQKVIFGSGTVTFSLSFDEPQKNAMAHRNSTHQNSLEAQKS
SDTLTRHQPLLPLQCGETDLDLTVQETGLQGPVGGDQRPEVEDPEELSPALVVSSSQSF
VISGGGSTVTENVVNS

>sp|Q9UBS5|GABR1_HUMAN Gamma-aminobutyric acid type B receptor subunit 1 OS=Homo sapiens GN=GABBR1 PE=1 SV=1 (SEQ ID NO:16)
MLLLLLLAPLFLRPPGAGGAQTPNATSEGCQIIHPPWEGGIRYRGLTRDQVKAINFLPV
DYEIEYVCRGEREVVGPKVRKCLANGSWTDMDTPSRCVRICSKSYLTLENGKVFLTGGD
LPALDGARVDFRCDPDFHLVGSSRSICSQGQWSTPKPHCQVNRTPHSERRAVYIGALFP
MSGGWPGGQACQPAVEMALEDVNSRRDILPDYELKLIHHDSKCDPGQATKYLYELLYND
PIKIILMPGCSSVSTLVAEAARMWNLIVLSYGSSSPALSNRQRFPTFFRTHPSATLHNP
TRVKLFEKWGWKKIATIQQTTEVFTSTLDDLEERVKEAGIEITFRQSFFSDPAVPVKNL
KRQDARIIVGLFYETEARKVFCEVYKERLFGKKYVWFLIGWYADNWFKIYDPSINCTVD
EMTEAVEGHITTEIVMLNPANTRSISNMTSQEFVEKLTKRLKRHPEETGGFQEAPLAYD
AIWALALALNKTSGGGGRSGVRLEDFNYNNQTITDQIYRAMNSSSFEGVSGHVVFDASG
SRMAWTLIEQLQGGSYKKIGYYDSTKDDLSWSKTDKWIGGSPPADQTLVIKTFRFLSQK
LFISVSVLSSLGIVLAVVCLSFNIYNSHVRYIQNSQPNLNNLTAVGCSLALAAVFPLGL
DGYHIGRNQFPFVCQARLWLLGLGFSLGYGSMFTKIWWVHTVFTKKEEKKEWRKTLEPW
                                                            ▲
KLYATVGLLVGMDVLTLAIWQIVDPLHRTIETFAKEEPKEDIDVSILPQLEHCSSRKMN
TWLGIFYGYKGLLLLLGIFLAYETKSVSTEKINDHRAVGMAIYNVAVLCLITAPVTMIL
SSQQDAAFAFASLAIVFSSYITLVVLFVPKMRRLITRGEWQSEAQDTMKTGSSTNNNEE
EKSRLLEKENRELEKIIAEKEERVSELRHQLQSRQQLRSRRHPPTPPEPSGGLPRGPPE
PPDRLSCDGSRVHLLYK >sp|O75899|GABR2_HUMAN Gamma-aminobutyric acid type B receptor subunit 2 OS=Homo sapiens GN=GABBR2 PE=1 SV=1 (SEQ ID NO:17)
MASPRSSGQPGPPPPPPPPPARLLLLLLLPLLLPLAPGAWGWARGAPRPPPSSPPLSIM
GLMPLTKEVAKGSIGRGVLPAVELAIEQIRNESLLRPYFLDLRLYDTECDNAKGLKAFY
DAIKYGPNHLMVFGGVCPSVTSIIAESLQGWNLVQLSFAATTPVLADKKKYPYFFRTVP
SDNAVNPAILKLLKHYQWKRVGTLTQDVQRFSEVRNDLTGVLYGEDIEISDTESFSNDP
CTSVKKLKGNDVRIILGQFDQNMAAKVFCCAYEENMYGSKYQWIIPGWYEPSWWEQVHT
EANSSRCLRKNLLAAMEGYIGVDFEPLSSKQIKTISGKTPQQYEREYNNKRSGVGPSKF
HGYAYDGIWVIAKTLQRAMETLHASSRHQRIQDFNYTDHTLGRIILNAMNETNFFGVTG
QVVFRNGERMGTIKFTQFQDSREVKVGEYNAVADTLEIINDTIRFQGSEPPKDKTIILE
QLRKISLPLYSILSALTILGMIMASAFLFFNIKNRNQKLIKMSSPYMNNLIILGGMLSY
ASIFLFGLDGSFVSEKTFETLCTVRTWILTVGYTTAFGAMFAKTWRVHAIFKNVKMKKK
                                                   ▲
IIKDQKLLVIVGGMLLIDLCILICWQAVDPLRRTVEKYSMEPDPAGRDISIRPLLEHCE
NTHMTIWLGIVYAYKGLLMLFGCFLAWETRNVSIPALNDSKYIGMSVYNVGIMCIIGAA

FIG. 4E

VSFLTRDQPNVQFCIVALVIIFCSTITLCLVFVPKLITLRTNPDAATQNRRFQFTQNQK
KEDSKTSTSVTSVNQASTSRLEGLQSENHRLRMKITELDKDLEEVTMQLQDTPEKTTYI
KQNHYQELNDILNLGNFTESTDGGKAILKNHLDQNPQLQWNTTEPSRTCKDPIEDINSP
EHIQRRLSLQLPILHHAYLPSIGGVDASCVSPCVSPTASPRHRHVPPSFRVMVSGL

>sp|Q7RTX1|TS1R1_HUMAN Taste receptor type 1 member 1
OS=Homo sapiens GN=TAS1R1 PE=2 SV=1 (SEQ ID NO:18)
MLLCTARLVGLQLLISCCWAFACHSTESSPDFTLPGDYLLAGLFPLHSGCLQVRHRPEV
TLCDRSCSFNEHGYHLFQAMRLGVEEINNSTALLPNITLGYQLYDVCSDSANVYATLRV
LSLPGQHHIELQGDLLHYSPTVLAVIGPDSTNRAATTAALLSPFLVPMISYAASSETLS
VKRQYPSFLRTIPNDKYQVETMVLLLQKFGWTWISLVGSSDDYGQLGVQALENQATGQG
ICIAFKDIMPFSAQVGDERMQCLMRHLAQAGATVVVVFSSRQLARVFFESVVLTNLTGK
VWVASEAWALSRHITGVPGIQRIGMVLGVAIQKRAVPGLKAFEEAYARADKKAPRPCHK
GSWCSSNQLCRECQAFMAHTMPKLKAFSMSSAYNAYRAVYAVAHGLHQLLGCASGACSR
GRVYPWQLLEQIHKVHFLLHKDTVAFNDNRDPLSSYNIIAWDWNGPKWTFTVLGSSTWS
PVQLNINETKIQWHGKDNQVPKSVCSSDCLEGHQRVVTGFHHCCFECVPCGAGTFLNKS
DLYRCQPCGKEEWAPEGSQTCFPRTVVFLALREHTSWVLLAANTLLLLLLLGTAGLFAW
HLDTPVVRSAGGRLCFLMLGSLAAGSGSLYGFFGEPTRPACLLRQA**LFALGFTIFLSCL
TVRSFQLIIIFKFSTKVPTFYHAWVQNHGAGLFVMISSAAQLLICLTWLVVW**TPLPARE YQRFPHLVMLECTETNSLGFILAFLYNGLLSISAFACSYLGKDLPENYNEAKCVTFSLL
FNFVSWIAFFTTASVYDGKYLPAANMMAGLSSLSSGFGGYFLPKCYVILCRPDLNSTEH
FQASIQDYTRRCGST >sp|Q8TE23|TS1R2_HUMAN Taste receptor type 1 member 2
OS=Homo sapiens GN=TAS1R2 PE=2 SV=2 (SEQ ID NO:19)
MGPRAKTISSLFFLLWVLAEPAENSDFYLPGDYLLGGLFSLHANMKGIVHLNFLQVPMC
KEYEVKVIGYNLMQAMRFAVEEINNDSSLLPGVLLGYEIVDVCYISNNVQPVLYFLAHE
DNLLPIQEDYSNYISRVVAVIGPDNSESVMTVANFLSLFLLPQITYSAISDELRDKVRF
PALLRTTPSADHHIEAMVQLMLHFRWNWIIVLVSSDTYGRDNGQLLGERVARRDICIAF
QETLPTLQPNQNMTSEERQRLVTIVDKLQQSTARVVVVFSPDLTLYHFFNEVLRQNFTG
AVWIASESWAIDPVLHNLTELRHLGTFLGITIQSVPIPGFSEFREWGPQAGPPPLSRTS
QSYTCNQECDNCLNATLSFNTILRLSGERVVYSVYSAVYAVAHALHSLLGCDKSTCTKR
VVYPWQLLEEIWKVNFTLLDHQIFFDPQGDVALHLEIVQWQWDRSQNPFQSVASYYPLQ
RQLKNIQDISWHTINNTIPMSMCSKRCQSGQKKKPVGIHVCCFECIDCLPGTFLNHTED
EYECQACPNNEWSYQSETSCFKRQLVFLEWHEAPTIAVALLAALGFLSTLAILVIFWRH
FQTPIVRSAGGPMCFLMLTLLLVAYMVVPVYVGPPKVSTCLCRQAL**FPLCFTICISCIA
VRSFQIVCAFKMASRFPRAYSYWVRYQGPYVSMAFITVLKMVIVVIGMLATGL**SPTTRT DPDDPKITIVSCNPNYRNSLLFNTSLDLLLSVVGFSFAYMGKELPTNYNEAKFITLSMT
FYFTSSVSLCTFMSAYSGVLVTIVDLLVTVLNLLAISLGYFGPKCYMILFYPERNTPAY
FNSMIQGYTMRRD

FIG. 4F

>sp|Q7RTX0|TS1R3_HUMAN Taste receptor type 1 member 3
OS=Homo sapiens GN=TAS1R3 PE=1 SV=2 (SEQ ID NO:20)
MLGPAVLGLSLWALLHPGTGAPLCLSQQLRMKGDYVLGGLFPLGEAEEAGLRSRTRPSS
PVCTRFSSNGLLWALAMKMAVEEINNKSDLLPGLRLGYDLFDTCSEPVVAMKPSLMFLA
KAGSRDIAAYCNYTQYQPRVLAVIGPHSSELAMVTGKFFSFFLMPQVSYGASMELLSAR
ETFPSFFRTVPSDRVQLTAAAELLQEFGWNWVAALGSDDEYGRQGLSIFSALAAARGIC
IAHEGLVPLPRADDSRLGKVQDVLHQVNQSSVQVVLLFASVHAAHALFNYSISSRLSPK
VWWVASEAWLTSDLVMGLPGMAQMGTVLGFLQRGAQLHEFPQYVKTHLALATDPAFCSAL
GEREQGLEEDVVGQRCPQCDCITLQNVSAGLNHHQTFSVYAAVYSVAQALHNTLQCNAS
GCPAQDPVKPWQLLENMYNLTFHVGGLPLRFDSSGNVDMEYDLKLWVWQGSVPRLHDVG
RFNGSLRTERLKIRWHTSDNQKPVSRCSRQCQEGQVRRVKGFHSCCYDCVDCEAGSYRQ
NPDDIACTFCGQDEWSPERSTRCFRRRSRFLAWGEPAVLLLLLLLSLALGLVLAALGLF
VHHRDSPLVQASGGPLACFGLVCLGLVCLSVLLFPGQPSPARCLAQQPLS**HLPLTGCLS
TLFLQAAEIFVESELPLSWADRLSGCLRGPWAWLVVLLAMLVEVALCTWYLVA**FPPEVV
▲

TDWHMLPTEALVHCRTRSWVSFGLAHATNATLAFLCFLGTFLVRSQPGCYNRARGLTFA
MLAYFITWVSFVPLLANVQVVLRPAVQMGALLLCVLGILAAFHLPRCYLLMRQPGLNTP
EFFLGGGPGDAQGQNDGNTGNQGKHE

>sp|Q5T6X5|GPC6A_HUMAN **G-protein coupled receptor family C
group 6 member A** OS=Homo sapiens GN=GPRC6A PE=1 SV=1 (SEQ
ID NO:21)
MAFLIILITCFVIILATSQPCQTPDDFVAATSPGHIIIGGLFAIHEKMLSSEDSPRRPQ
IQECVGFEISVFLQTLAMIHSIEMINNSTLLPGVKLGYEIYDTCTEVTVAMAATLRFLS
KFNCSRETVEFKCDYSSYMPRVKAVIGSGYSEITMAVSRMLNLQLMPQVGYESTAEILS
DKIRFPSFLRTVPSDFHQIKAMAHLIQKSGWNWIGIITTDDDYGRLALNTFIIQAEANN
VCIAFKEVLPAFLSDNTIEVRINRTLKKIILEAQVNVIVVFLRQFHVFDLFNKAIEMNI
NKMWIASDNWSTATKITTIPNVKKIGKVVGFAFRRGNISSFHSFLQNLHLLPSDSHKLL
HEYAMHLSACAYVKDTDLSQCIFNHSQRTLAYKANKAIERNFVMRNDFLWDYAEPGLIH
SIQLAVFALGYAIRDLCQARDCQNPNAFQPWELLGVLKNVTFTDGWNSFHFDAHGDLNT
GYDVVLWKEINGHMTVTKMAEYDLQNDVFIIPDQETKNEFRNLKQIQSKCSKECSPGQM
KKTTRSQHICCYECQNCPENHYTNQTDMPHCLLCNNKTHWAPVRSTMCFEKEVEYLNWN
DSLAILLLILSLLGIIFVLVVGIIFTRNLNTPVVKSSGGLRVCYVILLCHFLNFASTSF
FIGEPQDFTCKTRQTMFGVSFTLCISCILTKSLKILLAFSFDPKLQKFLKCLYRP**ILII
                                         ▲
FTCTGIQVVICTLWLIFAA**PTVEVNVSLPRVIILECEEGSILAFGTMLGYIAILAFICF
IFAFKGKYENYNEAKFITFGMLIYFIAWITFIPIYATTFGKYVPAVEIIVILISNYGIL
YCTFIPKCYVIICKQEINTKSAFLKMIYSYSSHSVSSIALSPASLDSMSGNVTMTNPSS
SGKSATWQKSKDLQAQAFAHICRENATSVSKTLPRKMSSI

FIG. 4G

Bovine Pancreatic Trypsin Inhibitor (SEQ ID NO:2)
RPDFCLEPPYTGPCKARIIRYFYNAKAGLCQTFVYGGCRAKRNNFKSAEDCMRTCGGA Bovine Calbindin D9K (SEQ ID NO:3)
MKSPEELKGIFEKYAAKEGDPNQLSKEELKLLLQTEFPSLLKGPSTLDELFEELDKNGDGEVSFEEFQV
LVKKISQ Barnase (SEQ ID NO:4)
MAQVINTFDGVADYLQTYHKLPDNYITKSEAQALGWVASKGNLADVAPGKSIGGDIFSNREGKLPGKS
GRTWREADINYTSGFRNSDRILYSSDWLIYKTTDHYQTFTKIR Xylanase II from Trichoderma reesei (SEQ ID NO:5)
ETIQPGTGYNNGYFYSYWNDGHGGVTYTNGPGGQFSVNWSNSGNFVGGKGWQPGTKNKVINFSGS
YNPNGNSYLSVYGWSRNPLIEYYIVENFGTYNPSTGATKLGEVTSDGSVYDIYRTQRVNQPSIIGTATF
YQYWSVRRNHRSSGSVNTANHFNAWAQQGLTLGTMDYQIVAVEGYFSSSGSASITVS Thermostable Glucokinase from Pyrococcus furiosus (SEQ ID NO:6)
MPTWEELYKNAIEKAIKSVPKVKGVLLGYNTNIDAIKYLDSKDLEERIIKAGKEEVIKYSEELPDKINTVSQ
LLGSILWSIRRGKAAELFVESCPVRFYMKRWGWNELRMGGQAGIMANLLGGVYGVPVIVHVPQLSRL
QANLFLDGPIYVPTLENGEVKLIHPKEFSGDEENCIHYIYEFPRGFRVFEFEAPRENRFIGSADDYNTTLF
IREEFRESFSEVIKNVQLAILSGLQALTKENYKEPFEIVKSNLEVLNEREIPVHLEFAFTPDEKVREEILNV
LGMFYSVGLNEVELASIMEILGEKKLAKELLAHDPVDPIAVTEAMLKLAKKTGVKRIHFHTYGYYLALTEY
KGEHVRDALLFAALAAAKAMKGNITSLEEIREATSVPVNEKATQVEEKLRAEYGIKEGIGEVEGYQIAFI
PTKIVAKPKSTVGIGDTISSSAFIGEFSFTL

FIG. 5

SEQUENCE LISTING

<160> NUMBER OF SEQ ID NOS: 22

<210> SEQ ID NO 1
<211> LENGTH: 473
<212> TYPE: PRT
<213> ORGANISM: Artificial Sequence
<220> FEATURE:
<223> OTHER INFORMATION: mGluR5 Rock 10 fusion protein

<400> SEQUENCE: 1

```
Asp Tyr Lys Asp Asp Asp Ala Ala Ala Pro Val Gln Tyr Leu Arg
1               5                   10                  15

Trp Gly Asp Pro Glu Pro Ile Ala Ala Val Val Phe Ala Cys Leu Gly
                20                  25                  30

Leu Leu Ala Thr Leu Phe Val Thr Val Ile Phe Ile Ile Tyr Arg Asp
            35                  40                  45

Thr Pro Val Val Lys Ser Ser Ser Arg Glu Leu Cys Tyr Ile Ile Leu
        50                  55                  60

Ala Gly Ile Cys Leu Gly Tyr Leu Cys Thr Phe Cys Leu Ile Ala Lys
65                  70                  75                  80

Pro Lys Gln Ile Tyr Cys Tyr Leu Gln Arg Ile Gly Ile Gly Leu Ser
                85                  90                  95

Pro Ala Met Ser Tyr Ser Ala Leu Val Thr Lys Thr Asn Arg Ile Ala
                100                 105                 110

Arg Ile Leu Ala Gly Ser Lys Lys Asn Ile Phe Glu Met Leu Arg Ile
            115                 120                 125

Asp Glu Gly Leu Arg Leu Lys Ile Tyr Lys Asp Thr Glu Gly Tyr Tyr
        130                 135                 140

Thr Ile Gly Ile Gly His Leu Leu Thr Lys Ser Pro Ser Leu Asn Ala
145                 150                 155                 160

Ala Lys Ser Glu Leu Asp Lys Ala Ile Gly Arg Asn Thr Asn Gly Val
                165                 170                 175

Ile Thr Lys Asp Glu Ala Glu Lys Leu Phe Asn Gln Asp Val Asp Ala
            180                 185                 190

Ala Val Arg Gly Ile Leu Arg Asn Ala Lys Leu Lys Pro Val Tyr Asp
        195                 200                 205

Ser Leu Asp Ala Val Arg Arg Ala Ala Leu Ile Asn Met Val Phe Gln
    210                 215                 220

Met Gly Glu Thr Gly Val Ala Gly Phe Thr Asn Ser Leu Arg Met Leu
225                 230                 235                 240
```

```
Gln Gln Lys Arg Trp Asp Glu Ala Ala Val Asn Leu Ala Lys Ser Arg
                245                 250                 255

Trp Tyr Asn Gln Thr Pro Asn Arg Ala Lys Arg Val Ile Thr Thr Phe
            260                 265                 270

Arg Thr Gly Thr Trp Asp Ala Tyr Lys Ile Cys Thr Lys Lys Pro Arg
        275                 280                 285

Phe Met Ser Ala Cys Ala Gln Leu Val Ile Ala Phe Ile Leu Ile Cys
    290                 295                 300

Ile Gln Leu Gly Ile Ile Val Ala Leu Phe Ile Met Glu Pro Pro Asp
305                 310                 315                 320

Ile Met His Asp Tyr Pro Ser Ile Arg Glu Val Tyr Leu Ile Cys Asn
                325                 330                 335

Thr Thr Asn Leu Gly Val Val Thr Pro Leu Gly Tyr Asn Gly Leu Leu
            340                 345                 350

Ile Leu Ser Cys Thr Phe Tyr Ala Phe Lys Thr Arg Asn Val Pro Ala
        355                 360                 365

Asn Phe Asn Glu Ala Lys Tyr Ile Ala Phe Thr Met Tyr Thr Thr Cys
    370                 375                 380

Ile Ile Trp Leu Ala Phe Val Pro Ile Tyr Phe Gly Ser Asn Tyr Lys
385                 390                 395                 400

Ile Ile Thr Met Cys Phe Ser Val Ser Leu Ser Ala Thr Val Ala Leu
                405                 410                 415

Gly Cys Met Phe Val Pro Lys Val Tyr Ile Ile Leu Ala Lys Pro Glu
            420                 425                 430

Arg Asn Val Arg Ser Ala Phe Thr Thr Ser Thr Val Val Arg Met His
        435                 440                 445

Val Gly Asp Gly Lys Ser Ser Ala Ala Ser Arg Ser Ser Ser Leu
    450                 455                 460

Val Asn Leu His His His His His
465                 470

<210> SEQ ID NO 2
<211> LENGTH: 58
<212> TYPE: PRT
<213> ORGANISM: Bos taurus

<400> SEQUENCE: 2

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55

<210> SEQ ID NO 3
<211> LENGTH: 76
<212> TYPE: PRT
<213> ORGANISM: Bos taurus

<400> SEQUENCE: 3

Met Lys Ser Pro Glu Glu Leu Lys Gly Ile Phe Glu Lys Tyr Ala Ala
1               5                   10                  15

Lys Glu Gly Asp Pro Asn Gln Leu Ser Lys Glu Glu Leu Lys Leu Leu
            20                  25                  30
```

```
Leu Gln Thr Glu Phe Pro Ser Leu Leu Lys Gly Pro Ser Thr Leu Asp
        35                  40                  45

Glu Leu Phe Glu Glu Leu Asp Lys Asn Gly Asp Gly Glu Val Ser Phe
 50                  55                  60

Glu Glu Phe Gln Val Leu Val Lys Lys Ile Ser Gln
65                  70                  75

<210> SEQ ID NO 4
<211> LENGTH: 111
<212> TYPE: PRT
<213> ORGANISM: Bacillus amyloliquefaciens

<400> SEQUENCE: 4

Met Ala Gln Val Ile Asn Thr Phe Asp Gly Val Ala Asp Tyr Leu Gln
1               5                   10                  15

Thr Tyr His Lys Leu Pro Asp Asn Tyr Ile Thr Lys Ser Glu Ala Gln
            20                  25                  30

Ala Leu Gly Trp Val Ala Ser Lys Gly Asn Leu Ala Asp Val Ala Pro
        35                  40                  45

Gly Lys Ser Ile Gly Gly Asp Ile Phe Ser Asn Arg Glu Gly Lys Leu
 50                  55                  60

Pro Gly Lys Ser Gly Arg Thr Trp Arg Glu Ala Asp Ile Asn Tyr Thr
65                  70                  75                  80

Ser Gly Phe Arg Asn Ser Asp Arg Ile Leu Tyr Ser Ser Asp Trp Leu
                85                  90                  95

Ile Tyr Lys Thr Thr Asp His Tyr Gln Thr Phe Thr Lys Ile Arg
            100                 105                 110

<210> SEQ ID NO 5
<211> LENGTH: 190
<212> TYPE: PRT
<213> ORGANISM: Trichoderma reesei

<400> SEQUENCE: 5

Glu Thr Ile Gln Pro Gly Thr Gly Tyr Asn Asn Gly Tyr Phe Tyr Ser
1               5                   10                  15

Tyr Trp Asn Asp Gly His Gly Gly Val Thr Tyr Thr Asn Gly Pro Gly
            20                  25                  30

Gly Gln Phe Ser Val Asn Trp Ser Asn Ser Gly Asn Phe Val Gly Gly
        35                  40                  45

Lys Gly Trp Gln Pro Gly Thr Lys Asn Lys Val Ile Asn Phe Ser Gly
 50                  55                  60

Ser Tyr Asn Pro Asn Gly Asn Ser Tyr Leu Ser Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
            115                 120                 125

Ile Gly Thr Ala Thr Phe Tyr Gln Tyr Trp Ser Val Arg Arg Asn His
        130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
```

<210> SEQ ID NO 6
<211> LENGTH: 455
<212> TYPE: PRT
<213> ORGANISM: Pyrococcus furiosus

<400> SEQUENCE: 6

```
Met Pro Thr Trp Glu Glu Leu Tyr Lys Asn Ala Ile Glu Lys Ala Ile
1               5                   10                  15
Lys Ser Val Pro Lys Val Lys Gly Val Leu Gly Tyr Asn Thr Asn
            20                  25                  30
Ile Asp Ala Ile Lys Tyr Leu Asp Ser Lys Asp Leu Glu Glu Arg Ile
            35                  40                  45
Ile Lys Ala Gly Lys Glu Val Ile Lys Tyr Ser Glu Glu Leu Pro
        50                  55                  60
Asp Lys Ile Asn Thr Val Ser Gln Leu Leu Gly Ser Ile Leu Trp Ser
65                  70                  75                  80
Ile Arg Arg Gly Lys Ala Ala Glu Leu Phe Val Glu Ser Cys Pro Val
                85                  90                  95
Arg Phe Tyr Met Lys Arg Trp Gly Trp Asn Glu Leu Arg Met Gly Gly
            100                 105                 110
Gln Ala Gly Ile Met Ala Asn Leu Leu Gly Gly Val Tyr Gly Val Pro
        115                 120                 125
Val Ile Val His Val Pro Gln Leu Ser Arg Leu Gln Ala Asn Leu Phe
    130                 135                 140
Leu Asp Gly Pro Ile Tyr Val Pro Thr Leu Glu Asn Gly Glu Val Lys
145                 150                 155                 160
Leu Ile His Pro Lys Glu Phe Ser Gly Asp Glu Asn Cys Ile His
                165                 170                 175
Tyr Ile Tyr Glu Phe Pro Arg Gly Phe Arg Val Phe Glu Phe Glu Ala
            180                 185                 190
Pro Arg Glu Asn Arg Phe Ile Gly Ser Ala Asp Asp Tyr Asn Thr Thr
        195                 200                 205
Leu Phe Ile Arg Glu Glu Phe Arg Glu Ser Phe Ser Glu Val Ile Lys
    210                 215                 220
Asn Val Gln Leu Ala Ile Leu Ser Gly Leu Gln Ala Leu Thr Lys Glu
225                 230                 235                 240
Asn Tyr Lys Glu Pro Phe Glu Ile Val Lys Ser Asn Leu Glu Val Leu
                245                 250                 255
Asn Glu Arg Glu Ile Pro Val His Leu Glu Phe Ala Phe Thr Pro Asp
            260                 265                 270
Glu Lys Val Arg Glu Glu Ile Leu Asn Val Leu Gly Met Phe Tyr Ser
        275                 280                 285
Val Gly Leu Asn Glu Val Glu Leu Ala Ser Ile Met Glu Ile Leu Gly
    290                 295                 300
Glu Lys Lys Leu Ala Lys Glu Leu Leu Ala His Asp Pro Val Asp Pro
305                 310                 315                 320
Ile Ala Val Thr Glu Ala Met Leu Lys Leu Ala Lys Lys Thr Gly Val
                325                 330                 335
Lys Arg Ile His Phe His Thr Tyr Gly Tyr Tyr Leu Ala Leu Thr Glu
            340                 345                 350
Tyr Lys Gly Glu His Val Arg Asp Ala Leu Leu Phe Ala Ala Leu Ala
        355                 360                 365
Ala Ala Ala Lys Ala Met Lys Gly Asn Ile Thr Ser Leu Glu Glu Ile
```

```
                370                 375                 380
Arg Glu Ala Thr Ser Val Pro Val Asn Glu Lys Ala Thr Gln Val Glu
385                 390                 395                 400

Glu Lys Leu Arg Ala Glu Tyr Gly Ile Lys Glu Gly Ile Gly Glu Val
            405                 410                 415

Glu Gly Tyr Gln Ile Ala Phe Ile Pro Thr Lys Ile Val Ala Lys Pro
        420                 425                 430

Lys Ser Thr Val Gly Ile Gly Asp Thr Ile Ser Ser Ala Phe Ile
    435                 440                 445

Gly Glu Phe Ser Phe Thr Leu
    450                 455

<210> SEQ ID NO 7
<211> LENGTH: 1194
<212> TYPE: PRT
<213> ORGANISM: Homo sapiens

<400> SEQUENCE: 7

Met Val Gly Leu Leu Phe Phe Pro Ala Ile Phe Leu Glu Val
1               5                   10                  15

Ser Leu Leu Pro Arg Ser Gly Arg Lys Val Leu Leu Ala Gly Ala
                20                  25                  30

Ser Ser Gln Arg Ser Val Ala Arg Met Asp Gly Asp Val Ile Ile Gly
            35                  40                  45

Ala Leu Phe Ser Val His His Gln Pro Pro Ala Glu Lys Val Pro Glu
    50                  55                  60

Arg Lys Cys Gly Glu Ile Arg Glu Gln Tyr Gly Ile Gln Arg Val Glu
65                  70                  75                  80

Ala Met Phe His Thr Leu Asp Lys Ile Asn Ala Asp Pro Val Leu Leu
                85                  90                  95

Pro Asn Ile Thr Leu Gly Ser Glu Ile Arg Asp Ser Cys Trp His Ser
            100                 105                 110

Ser Val Ala Leu Glu Gln Ser Ile Glu Phe Ile Arg Asp Ser Leu Ile
    115                 120                 125

Ser Ile Arg Asp Glu Lys Asp Gly Ile Asn Arg Cys Leu Pro Asp Gly
130                 135                 140

Gln Ser Leu Pro Pro Gly Arg Thr Lys Lys Pro Ile Ala Gly Val Ile
145                 150                 155                 160

Gly Pro Gly Ser Ser Ser Val Ala Ile Gln Val Gln Asn Leu Leu Gln
                165                 170                 175

Leu Phe Asp Ile Pro Gln Ile Ala Tyr Ser Ala Thr Ser Ile Asp Leu
            180                 185                 190

Ser Asp Lys Thr Leu Tyr Lys Tyr Phe Leu Arg Val Val Pro Ser Asp
    195                 200                 205

Thr Leu Gln Ala Arg Ala Met Leu Asp Ile Val Lys Arg Tyr Asn Trp
210                 215                 220

Thr Tyr Val Ser Ala Val His Thr Glu Gly Asn Tyr Gly Glu Ser Gly
225                 230                 235                 240

Met Asp Ala Phe Lys Glu Leu Ala Ala Gln Glu Gly Leu Cys Ile Ala
                245                 250                 255

His Ser Asp Lys Ile Tyr Ser Asn Ala Gly Glu Lys Ser Phe Asp Arg
            260                 265                 270

Leu Leu Arg Lys Leu Arg Glu Arg Leu Pro Lys Ala Arg Val Val Val
    275                 280                 285

Cys Phe Cys Glu Gly Met Thr Val Arg Gly Leu Leu Ser Ala Met Arg
```

-continued

```
                290                 295                 300
Arg Leu Gly Val Val Gly Glu Phe Ser Leu Ile Gly Ser Asp Gly Trp
305                 310                 315                 320

Ala Asp Arg Asp Glu Val Ile Glu Gly Tyr Glu Val Glu Ala Asn Gly
                325                 330                 335

Gly Ile Thr Ile Lys Leu Gln Ser Pro Glu Val Arg Ser Phe Asp Asp
                340                 345                 350

Tyr Phe Leu Lys Leu Arg Leu Asp Thr Asn Thr Arg Asn Pro Trp Phe
            355                 360                 365

Pro Glu Phe Trp Gln His Arg Phe Gln Cys Arg Leu Pro Gly His Leu
370                 375                 380

Leu Glu Asn Pro Asn Phe Lys Arg Ile Cys Thr Gly Asn Glu Ser Leu
385                 390                 395                 400

Glu Glu Asn Tyr Val Gln Asp Ser Lys Met Gly Phe Val Ile Asn Ala
                405                 410                 415

Ile Tyr Ala Met Ala His Gly Leu Gln Asn Met His His Ala Leu Cys
            420                 425                 430

Pro Gly His Val Gly Leu Cys Asp Ala Met Lys Pro Ile Asp Gly Ser
        435                 440                 445

Lys Leu Leu Asp Phe Leu Ile Lys Ser Ser Phe Ile Gly Val Ser Gly
450                 455                 460

Glu Glu Val Trp Phe Asp Glu Lys Gly Asp Ala Pro Gly Arg Tyr Asp
465                 470                 475                 480

Ile Met Asn Leu Gln Tyr Thr Glu Ala Asn Arg Tyr Asp Tyr Val His
                485                 490                 495

Val Gly Thr Trp His Glu Gly Val Leu Asn Ile Asp Asp Tyr Lys Ile
            500                 505                 510

Gln Met Asn Lys Ser Gly Val Val Arg Ser Val Cys Ser Glu Pro Cys
        515                 520                 525

Leu Lys Gly Gln Ile Lys Val Ile Arg Lys Gly Glu Val Ser Cys Cys
530                 535                 540

Trp Ile Cys Thr Ala Cys Lys Glu Asn Glu Tyr Val Gln Asp Glu Phe
545                 550                 555                 560

Thr Cys Lys Ala Cys Asp Leu Gly Trp Trp Pro Asn Ala Asp Leu Thr
                565                 570                 575

Gly Cys Glu Pro Ile Pro Val Arg Tyr Leu Glu Trp Ser Asn Ile Glu
            580                 585                 590

Ser Ile Ile Ala Ile Ala Phe Ser Cys Leu Gly Ile Leu Val Thr Leu
        595                 600                 605

Phe Val Thr Leu Ile Phe Val Leu Tyr Arg Asp Thr Pro Val Val Lys
610                 615                 620

Ser Ser Ser Arg Glu Leu Cys Tyr Ile Ile Leu Ala Gly Ile Phe Leu
625                 630                 635                 640

Gly Tyr Val Cys Pro Phe Thr Leu Ile Ala Lys Pro Thr Thr Thr Ser
                645                 650                 655

Cys Tyr Leu Gln Arg Leu Leu Val Gly Leu Ser Ser Ala Met Cys Tyr
            660                 665                 670

Ser Ala Leu Val Thr Lys Thr Asn Arg Ile Ala Arg Ile Leu Ala Gly
        675                 680                 685

Ser Lys Lys Lys Ile Cys Thr Arg Lys Pro Arg Phe Met Ser Ala Trp
690                 695                 700

Ala Gln Val Ile Ile Ala Ser Ile Leu Ile Ser Val Gln Leu Thr Leu
705                 710                 715                 720
```

-continued

Val Val Thr Leu Ile Ile Met Glu Pro Pro Met Pro Ile Leu Ser Tyr
            725                 730                 735

Pro Ser Ile Lys Glu Val Tyr Leu Ile Cys Asn Thr Ser Asn Leu Gly
            740                 745                 750

Val Val Ala Pro Leu Gly Tyr Asn Gly Leu Leu Ile Met Ser Cys Thr
            755                 760                 765

Tyr Tyr Ala Phe Lys Thr Arg Asn Val Pro Ala Asn Phe Asn Glu Ala
            770                 775                 780

Lys Tyr Ile Ala Phe Thr Met Tyr Thr Thr Cys Ile Ile Trp Leu Ala
785                 790                 795                 800

Phe Val Pro Ile Tyr Phe Gly Ser Asn Tyr Lys Ile Ile Thr Thr Cys
            805                 810                 815

Phe Ala Val Ser Leu Ser Val Thr Val Ala Leu Gly Cys Met Phe Thr
            820                 825                 830

Pro Lys Met Tyr Ile Ile Ile Ala Lys Pro Glu Arg Asn Val Arg Ser
            835                 840                 845

Ala Phe Thr Thr Ser Asp Val Val Arg Met His Val Gly Asp Gly Lys
            850                 855                 860

Leu Pro Cys Arg Ser Asn Thr Phe Leu Asn Ile Phe Arg Arg Lys Lys
865                 870                 875                 880

Ala Gly Ala Gly Asn Ala Asn Ser Asn Gly Lys Ser Val Ser Trp Ser
            885                 890                 895

Glu Pro Gly Gly Gly Gln Val Pro Lys Gly Gln His Met Trp His Arg
            900                 905                 910

Leu Ser Val His Val Lys Thr Asn Glu Thr Ala Cys Asn Gln Thr Ala
            915                 920                 925

Val Ile Lys Pro Leu Thr Lys Ser Tyr Gln Gly Ser Gly Lys Ser Leu
            930                 935                 940

Thr Phe Ser Asp Thr Ser Thr Lys Thr Leu Tyr Asn Val Glu Glu Glu
945                 950                 955                 960

Glu Asp Ala Gln Pro Ile Arg Phe Ser Pro Gly Ser Pro Ser Met
            965                 970                 975

Val Val His Arg Arg Val Pro Ser Ala Ala Thr Thr Pro Pro Leu Pro
            980                 985                 990

Pro His Leu Thr Ala Glu Glu Thr Pro Leu Phe Leu Ala Glu Pro Ala
            995                 1000                1005

Leu Pro Lys Gly Leu Pro Pro Pro Leu Gln Gln Gln Gln Gln Pro
1010                1015                1020

Pro Pro Gln Gln Lys Ser Leu Met Asp Gln Leu Gln Gly Val Val
1025                1030                1035

Ser Asn Phe Ser Thr Ala Ile Pro Asp Phe His Ala Val Leu Ala
1040                1045                1050

Gly Pro Gly Gly Pro Gly Asn Gly Leu Arg Ser Leu Tyr Pro Pro
1055                1060                1065

Pro Pro Pro Pro Gln His Leu Gln Met Leu Pro Leu Gln Leu Ser
1070                1075                1080

Thr Phe Gly Glu Glu Leu Val Ser Pro Pro Ala Asp Asp Asp Asp
1085                1090                1095

Asp Ser Glu Arg Phe Lys Leu Leu Gln Glu Tyr Val Tyr Glu His
1100                1105                1110

Glu Arg Glu Gly Asn Thr Glu Glu Asp Glu Leu Glu Glu Glu Glu
1115                1120                1125

Glu Asp Leu Gln Ala Ala Ser Lys Leu Thr Pro Asp Asp Ser Pro
1130                1135                1140

```
Ala Leu Thr Pro Pro Ser Pro Phe Arg Asp Ser Val Ala Ser Gly
    1145                1150                1155

Ser Ser Val Pro Ser Ser Pro Val Ser Glu Ser Val Leu Cys Thr
    1160                1165                1170

Pro Pro Asn Val Ser Tyr Ala Ser Val Ile Leu Arg Asp Tyr Lys
    1175                1180                1185

Gln Ser Ser Ser Thr Leu
    1190

<210> SEQ ID NO 8
<211> LENGTH: 872
<212> TYPE: PRT
<213> ORGANISM: Homo sapiens

<400> SEQUENCE: 8

Met Gly Ser Leu Leu Ala Leu Ala Leu Leu Leu Trp Gly Ala
1               5                   10                  15

Val Ala Glu Gly Pro Ala Lys Lys Val Leu Thr Leu Glu Gly Asp Leu
                20                  25                  30

Val Leu Gly Gly Leu Phe Pro Val His Gln Lys Gly Gly Pro Ala Glu
            35                  40                  45

Asp Cys Gly Pro Val Asn Glu His Arg Gly Ile Gln Arg Leu Glu Ala
        50                  55                  60

Met Leu Phe Ala Leu Asp Arg Ile Asn Arg Asp Pro His Leu Leu Pro
65                  70                  75                  80

Gly Val Arg Leu Gly Ala His Ile Leu Asp Ser Cys Ser Lys Asp Thr
                85                  90                  95

His Ala Leu Glu Gln Ala Leu Asp Phe Val Arg Ala Ser Leu Ser Arg
            100                 105                 110

Gly Ala Asp Gly Ser Arg His Ile Cys Pro Asp Gly Ser Tyr Ala Thr
        115                 120                 125

His Gly Asp Ala Pro Thr Ala Ile Thr Gly Val Ile Gly Gly Ser Tyr
    130                 135                 140

Ser Asp Val Ser Ile Gln Val Ala Asn Leu Leu Arg Leu Phe Gln Ile
145                 150                 155                 160

Pro Gln Ile Ser Tyr Ala Ser Thr Ser Ala Lys Leu Ser Asp Lys Ser
                165                 170                 175

Arg Tyr Asp Tyr Phe Ala Arg Thr Val Pro Pro Asp Phe Phe Gln Ala
            180                 185                 190

Lys Ala Met Ala Glu Ile Leu Arg Phe Phe Asn Trp Thr Tyr Val Ser
        195                 200                 205

Thr Val Ala Ser Glu Gly Asp Tyr Gly Glu Thr Gly Ile Glu Ala Phe
    210                 215                 220

Glu Leu Glu Ala Arg Ala Arg Asn Ile Cys Val Ala Thr Ser Glu Lys
225                 230                 235                 240

Val Gly Arg Ala Met Ser Arg Ala Ala Phe Glu Gly Val Val Arg Ala
                245                 250                 255

Leu Leu Gln Lys Pro Ser Ala Arg Val Ala Val Leu Phe Thr Arg Ser
            260                 265                 270

Glu Asp Ala Arg Glu Leu Leu Ala Ala Ser Gln Arg Leu Asn Ala Ser
        275                 280                 285

Phe Thr Trp Val Ala Ser Asp Gly Trp Gly Ala Leu Glu Ser Val Val
    290                 295                 300

Ala Gly Ser Glu Gly Ala Ala Glu Gly Ala Ile Thr Ile Glu Leu Ala
305                 310                 315                 320
```

```
Ser Tyr Pro Ile Ser Asp Phe Ala Ser Tyr Phe Gln Ser Leu Asp Pro
                325                 330                 335

Trp Asn Asn Ser Arg Asn Pro Trp Phe Arg Glu Phe Trp Glu Gln Arg
            340                 345                 350

Phe Arg Cys Ser Phe Arg Gln Arg Asp Cys Ala Ala His Ser Leu Arg
        355                 360                 365

Ala Val Pro Phe Glu Gln Glu Ser Lys Ile Met Phe Val Val Asn Ala
    370                 375                 380

Val Tyr Ala Met Ala His Ala Leu His Asn Met His Arg Ala Leu Cys
385                 390                 395                 400

Pro Asn Thr Thr Arg Leu Cys Asp Ala Met Arg Pro Val Asn Gly Arg
                405                 410                 415

Arg Leu Tyr Lys Asp Phe Val Leu Asn Val Lys Phe Asp Ala Pro Phe
            420                 425                 430

Arg Pro Ala Asp Thr His Asn Glu Val Arg Phe Asp Arg Phe Gly Asp
        435                 440                 445

Gly Ile Gly Arg Tyr Asn Ile Phe Thr Tyr Leu Arg Ala Gly Ser Gly
    450                 455                 460

Arg Tyr Arg Tyr Gln Lys Val Gly Tyr Trp Ala Glu Gly Leu Thr Leu
465                 470                 475                 480

Asp Thr Ser Leu Ile Pro Trp Ala Ser Pro Ala Gly Pro Leu Pro
                485                 490                 495

Ala Ser Arg Cys Ser Glu Pro Cys Leu Gln Asn Glu Val Lys Ser Val
            500                 505                 510

Gln Pro Gly Glu Val Cys Cys Trp Leu Cys Ile Pro Cys Gln Pro Tyr
        515                 520                 525

Glu Tyr Arg Leu Asp Glu Phe Thr Cys Ala Asp Cys Gly Leu Gly Tyr
    530                 535                 540

Trp Pro Asn Ala Ser Leu Thr Gly Cys Phe Glu Leu Pro Gln Glu Tyr
545                 550                 555                 560

Ile Arg Trp Gly Asp Ala Trp Ala Val Gly Pro Val Thr Ile Ala Cys
                565                 570                 575

Leu Gly Ala Leu Ala Thr Leu Phe Val Leu Gly Val Phe Val Arg His
            580                 585                 590

Asn Ala Thr Pro Val Val Lys Ala Ser Gly Arg Glu Leu Cys Tyr Ile
        595                 600                 605

Leu Leu Gly Gly Val Phe Leu Cys Tyr Cys Met Thr Phe Ile Phe Ile
    610                 615                 620

Ala Lys Pro Ser Thr Ala Val Cys Thr Leu Arg Arg Leu Gly Leu Gly
625                 630                 635                 640

Thr Ala Phe Ser Val Cys Tyr Ser Ala Leu Leu Thr Lys Thr Asn Arg
                645                 650                 655

Ile Ala Arg Ile Phe Gly Gly Ala Arg Glu Gly Ala Gln Arg Pro Arg
            660                 665                 670

Phe Ile Ser Pro Ala Ser Gln Val Ala Ile Cys Leu Ala Leu Ile Ser
        675                 680                 685

Gly Gln Leu Leu Ile Val Val Ala Trp Leu Val Val Glu Ala Pro Gly
    690                 695                 700

Thr Gly Lys Glu Thr Ala Pro Glu Arg Arg Glu Val Val Thr Leu Arg
705                 710                 715                 720

Cys Asn His Arg Asp Ala Ser Met Leu Gly Ser Leu Ala Tyr Asn Val
                725                 730                 735

Leu Leu Ile Ala Leu Cys Thr Leu Tyr Ala Phe Lys Thr Arg Lys Cys
```

```
                    740                 745                 750
Pro Glu Asn Phe Asn Glu Ala Lys Phe Ile Gly Phe Thr Met Tyr Thr
                755                 760                 765

Thr Cys Ile Ile Trp Leu Ala Phe Leu Pro Ile Phe Tyr Val Thr Ser
            770                 775                 780

Ser Asp Tyr Arg Val Gln Thr Thr Thr Met Cys Val Ser Val Ser Leu
785                 790                 795                 800

Ser Gly Ser Val Val Leu Gly Cys Leu Phe Ala Pro Lys Leu His Ile
                805                 810                 815

Ile Leu Phe Gln Pro Gln Lys Asn Val Val Ser His Arg Ala Pro Thr
            820                 825                 830

Ser Arg Phe Gly Ser Ala Ala Arg Ala Ser Ser Ser Leu Gly Gln
            835                 840                 845

Gly Ser Gly Ser Gln Phe Val Pro Thr Val Cys Asn Gly Arg Glu Val
    850                 855                 860

Val Asp Ser Thr Thr Ser Ser Leu
865                 870

<210> SEQ ID NO 9
<211> LENGTH: 879
<212> TYPE: PRT
<213> ORGANISM: Homo sapiens

<400> SEQUENCE: 9

Met Lys Met Leu Thr Arg Leu Gln Val Leu Thr Leu Ala Leu Phe Ser
1               5                   10                  15

Lys Gly Phe Leu Leu Ser Leu Gly Asp His Asn Phe Leu Arg Arg Glu
            20                  25                  30

Ile Lys Ile Glu Gly Asp Leu Val Leu Gly Gly Leu Phe Pro Ile Asn
        35                  40                  45

Glu Lys Gly Thr Gly Thr Glu Glu Cys Gly Arg Ile Asn Glu Asp Arg
    50                  55                  60

Gly Ile Gln Arg Leu Glu Ala Met Leu Phe Ala Ile Asp Glu Ile Asn
65                  70                  75                  80

Lys Asp Asp Tyr Leu Leu Pro Gly Val Lys Leu Gly Val His Ile Leu
                85                  90                  95

Asp Thr Cys Ser Arg Asp Thr Tyr Ala Leu Glu Gln Ser Leu Glu Phe
            100                 105                 110

Val Arg Ala Ser Leu Thr Lys Val Asp Glu Ala Glu Tyr Met Cys Pro
        115                 120                 125

Asp Gly Ser Tyr Ala Ile Gln Glu Asn Ile Pro Leu Leu Ile Ala Gly
    130                 135                 140

Val Ile Gly Gly Ser Tyr Ser Ser Val Ser Ile Gln Val Ala Asn Leu
145                 150                 155                 160

Leu Arg Leu Phe Gln Ile Pro Gln Ile Ser Tyr Ala Ser Thr Ser Ala
                165                 170                 175

Lys Leu Ser Asp Lys Ser Arg Tyr Asp Tyr Phe Ala Arg Thr Val Pro
            180                 185                 190

Pro Asp Phe Tyr Gln Ala Lys Ala Met Ala Glu Ile Leu Arg Phe Phe
        195                 200                 205

Asn Trp Thr Tyr Val Ser Thr Val Ala Ser Glu Gly Asp Tyr Gly Glu
    210                 215                 220

Thr Gly Ile Glu Ala Phe Glu Gln Glu Ala Arg Leu Arg Asn Ile Cys
225                 230                 235                 240

Ile Ala Thr Ala Glu Lys Val Gly Arg Ser Asn Ile Arg Lys Ser Tyr
```

```
                     245                 250                 255
Asp Ser Val Ile Arg Glu Leu Leu Gln Lys Pro Asn Ala Arg Val Val
                260                 265                 270
Val Leu Phe Met Arg Ser Asp Asp Ser Arg Glu Leu Ile Ala Ala Ala
                275                 280                 285
Ser Arg Ala Asn Ala Ser Phe Thr Trp Val Ala Ser Asp Gly Trp Gly
                290                 295                 300
Ala Gln Glu Ser Ile Ile Lys Gly Ser Glu His Val Ala Tyr Gly Ala
305                 310                 315                 320
Ile Thr Leu Glu Leu Ala Ser Gln Pro Val Arg Gln Phe Asp Arg Tyr
                325                 330                 335
Phe Gln Ser Leu Asn Pro Tyr Asn Asn His Arg Asn Pro Trp Phe Arg
                340                 345                 350
Asp Phe Trp Glu Gln Lys Phe Gln Cys Ser Leu Gln Asn Lys Arg Asn
                355                 360                 365
His Arg Arg Val Cys Asp Lys His Leu Ala Ile Asp Ser Ser Asn Tyr
                370                 375                 380
Glu Gln Glu Ser Lys Ile Met Phe Val Val Asn Ala Val Tyr Ala Met
385                 390                 395                 400
Ala His Ala Leu His Lys Met Gln Arg Thr Leu Cys Pro Asn Thr Thr
                405                 410                 415
Lys Leu Cys Asp Ala Met Lys Ile Leu Asp Gly Lys Lys Leu Tyr Lys
                420                 425                 430
Asp Tyr Leu Leu Lys Ile Asn Phe Thr Ala Pro Phe Asn Pro Asn Lys
                435                 440                 445
Asp Ala Asp Ser Ile Val Lys Phe Asp Thr Phe Gly Asp Gly Met Gly
                450                 455                 460
Arg Tyr Asn Val Phe Asn Phe Gln Asn Val Gly Gly Lys Tyr Ser Tyr
465                 470                 475                 480
Leu Lys Val Gly His Trp Ala Glu Thr Leu Ser Leu Asp Val Asn Ser
                485                 490                 495
Ile His Trp Ser Arg Asn Ser Val Pro Thr Ser Gln Cys Ser Asp Pro
                500                 505                 510
Cys Ala Pro Asn Glu Met Lys Asn Met Gln Pro Gly Asp Val Cys Cys
                515                 520                 525
Trp Ile Cys Ile Pro Cys Glu Pro Tyr Glu Tyr Leu Ala Asp Glu Phe
                530                 535                 540
Thr Cys Met Asp Cys Gly Ser Gly Gln Trp Pro Thr Ala Asp Leu Thr
545                 550                 555                 560
Gly Cys Tyr Asp Leu Pro Glu Asp Tyr Ile Arg Trp Glu Asp Ala Trp
                565                 570                 575
Ala Ile Gly Pro Val Thr Ile Ala Cys Leu Gly Phe Met Cys Thr Cys
                580                 585                 590
Met Val Val Thr Val Phe Ile Lys His Asn Asn Thr Pro Leu Val Lys
                595                 600                 605
Ala Ser Gly Arg Glu Leu Cys Tyr Ile Leu Leu Phe Gly Val Gly Leu
                610                 615                 620
Ser Tyr Cys Met Thr Phe Phe Ile Ala Lys Pro Ser Pro Val Ile
625                 630                 635                 640
Cys Ala Leu Arg Arg Leu Gly Leu Gly Ser Ser Phe Ala Ile Cys Tyr
                645                 650                 655
Ser Ala Leu Leu Thr Lys Thr Asn Cys Ile Ala Arg Ile Phe Asp Gly
                660                 665                 670
```

```
Val Lys Asn Gly Ala Gln Arg Pro Lys Phe Ile Ser Pro Ser Ser Gln
    675                 680                 685

Val Phe Ile Cys Leu Gly Leu Ile Leu Val Gln Ile Val Met Val Ser
690                 695                 700

Val Trp Leu Ile Leu Glu Ala Pro Gly Thr Arg Arg Tyr Thr Leu Ala
705                 710                 715                 720

Glu Lys Arg Glu Thr Val Ile Leu Lys Cys Asn Val Lys Asp Ser Ser
                725                 730                 735

Met Leu Ile Ser Leu Thr Tyr Asp Val Ile Leu Val Ile Leu Cys Thr
                740                 745                 750

Val Tyr Ala Phe Lys Thr Arg Lys Cys Pro Glu Asn Phe Asn Glu Ala
                755                 760                 765

Lys Phe Ile Gly Phe Thr Met Tyr Thr Thr Cys Ile Ile Trp Leu Ala
                770                 775                 780

Phe Leu Pro Ile Phe Tyr Val Thr Ser Ser Asp Tyr Arg Val Gln Thr
785                 790                 795                 800

Thr Thr Met Cys Ile Ser Val Ser Leu Ser Gly Phe Val Val Leu Gly
                805                 810                 815

Cys Leu Phe Ala Pro Lys Val His Ile Ile Leu Phe Gln Pro Gln Lys
                820                 825                 830

Asn Val Val Thr His Arg Leu His Leu Asn Arg Phe Ser Val Ser Gly
                835                 840                 845

Thr Gly Thr Thr Tyr Ser Gln Ser Ser Ala Ser Thr Tyr Val Pro Thr
850                 855                 860

Val Cys Asn Gly Arg Glu Val Leu Asp Ser Thr Thr Ser Ser Leu
865                 870                 875

<210> SEQ ID NO 10
<211> LENGTH: 912
<212> TYPE: PRT
<213> ORGANISM: Homo sapiens

<400> SEQUENCE: 10

Met Pro Gly Lys Arg Gly Leu Gly Trp Trp Trp Ala Arg Leu Pro Leu
1               5                   10                  15

Cys Leu Leu Leu Ser Leu Tyr Gly Pro Trp Met Pro Ser Ser Leu Gly
                20                  25                  30

Lys Pro Lys Gly His Pro His Met Asn Ser Ile Arg Ile Asp Gly Asp
                35                  40                  45

Ile Thr Leu Gly Gly Leu Phe Pro Val His Gly Arg Gly Ser Glu Gly
        50                  55                  60

Lys Pro Cys Gly Glu Leu Lys Lys Glu Lys Gly Ile His Arg Leu Glu
65                  70                  75                  80

Ala Met Leu Phe Ala Leu Asp Arg Ile Asn Asn Asp Pro Asp Leu Leu
                85                  90                  95

Pro Asn Ile Thr Leu Gly Ala Arg Ile Leu Asp Thr Cys Ser Arg Asp
                100                 105                 110

Thr His Ala Leu Glu Gln Ser Leu Thr Phe Val Gln Ala Leu Ile Glu
                115                 120                 125

Lys Asp Gly Thr Glu Val Arg Cys Gly Ser Gly Gly Pro Pro Ile Ile
        130                 135                 140

Thr Lys Pro Glu Arg Val Val Gly Val Ile Gly Ala Ser Gly Ser Ser
145                 150                 155                 160

Val Ser Ile Met Val Ala Asn Ile Leu Arg Leu Phe Lys Ile Pro Gln
                165                 170                 175
```

```
Ile Ser Tyr Ala Ser Thr Ala Pro Asp Leu Ser Asp Asn Ser Arg Tyr
            180                 185                 190

Asp Phe Phe Ser Arg Val Val Pro Ser Asp Thr Tyr Gln Ala Gln Ala
            195                 200                 205

Met Val Asp Ile Val Arg Ala Leu Lys Trp Asn Tyr Val Ser Thr Val
210                 215                 220

Ala Ser Glu Gly Ser Tyr Gly Glu Ser Gly Val Glu Ala Phe Ile Gln
225                 230                 235                 240

Lys Ser Arg Glu Asp Gly Val Cys Ile Ala Gln Ser Val Lys Ile
                245                 250                 255

Pro Arg Glu Pro Lys Ala Gly Phe Asp Lys Ile Ile Arg Arg Leu
            260                 265                 270

Leu Glu Thr Ser Asn Ala Arg Ala Val Ile Ile Phe Ala Asn Glu Asp
            275                 280                 285

Asp Ile Arg Arg Val Leu Glu Ala Ala Arg Arg Ala Asn Gln Thr Gly
            290                 295                 300

His Phe Phe Trp Met Gly Ser Asp Ser Trp Gly Ser Lys Ile Ala Pro
305                 310                 315                 320

Val Leu His Leu Glu Glu Val Ala Glu Gly Ala Val Thr Ile Leu Pro
                325                 330                 335

Lys Arg Met Ser Val Arg Gly Phe Asp Arg Tyr Phe Ser Ser Arg Thr
            340                 345                 350

Leu Asp Asn Asn Arg Arg Asn Ile Trp Phe Ala Glu Phe Trp Glu Asp
            355                 360                 365

Asn Phe His Cys Lys Leu Ser Arg His Ala Leu Lys Lys Gly Ser His
            370                 375                 380

Val Lys Lys Cys Thr Asn Arg Glu Arg Ile Gly Gln Asp Ser Ala Tyr
385                 390                 395                 400

Glu Gln Glu Gly Lys Val Gln Phe Val Ile Asp Ala Val Tyr Ala Met
                405                 410                 415

Gly His Ala Leu His Ala Met His Arg Asp Leu Cys Pro Gly Arg Val
            420                 425                 430

Gly Leu Cys Pro Arg Met Asp Pro Val Asp Gly Thr Gln Leu Leu Lys
            435                 440                 445

Tyr Ile Arg Asn Val Asn Phe Ser Gly Ile Ala Gly Asn Pro Val Thr
450                 455                 460

Phe Asn Glu Asn Gly Asp Ala Pro Gly Arg Tyr Asp Ile Tyr Gln Tyr
465                 470                 475                 480

Gln Leu Arg Asn Asp Ser Ala Glu Tyr Lys Val Ile Gly Ser Trp Thr
                485                 490                 495

Asp His Leu His Leu Arg Ile Glu Arg Met His Trp Pro Gly Ser Gly
            500                 505                 510

Gln Gln Leu Pro Arg Ser Ile Cys Ser Leu Pro Cys Gln Pro Gly Glu
            515                 520                 525

Arg Lys Lys Thr Val Lys Gly Met Pro Cys Cys Trp His Cys Glu Pro
            530                 535                 540

Cys Thr Gly Tyr Gln Tyr Gln Val Asp Arg Tyr Thr Cys Lys Thr Cys
545                 550                 555                 560

Pro Tyr Asp Met Arg Pro Thr Glu Asn Arg Thr Gly Cys Arg Pro Ile
                565                 570                 575

Pro Ile Ile Lys Leu Glu Trp Gly Ser Pro Trp Ala Val Leu Pro Leu
            580                 585                 590

Phe Leu Ala Val Val Gly Ile Ala Ala Thr Leu Phe Val Val Ile Thr
            595                 600                 605
```

```
Phe Val Arg Tyr Asn Asp Thr Pro Ile Val Lys Ala Ser Gly Arg Glu
    610                 615                 620

Leu Ser Tyr Val Leu Leu Ala Gly Ile Phe Leu Cys Tyr Ala Thr Thr
625                 630                 635                 640

Phe Leu Met Ile Ala Glu Pro Asp Leu Gly Thr Cys Ser Leu Arg Arg
            645                 650                 655

Ile Phe Leu Gly Leu Gly Met Ser Ile Ser Tyr Ala Ala Leu Leu Thr
            660                 665                 670

Lys Thr Asn Arg Ile Tyr Arg Ile Phe Glu Gln Gly Lys Arg Ser Val
            675                 680                 685

Ser Ala Pro Arg Phe Ile Ser Pro Ala Ser Gln Leu Ala Ile Thr Phe
690                 695                 700

Ser Leu Ile Ser Leu Gln Leu Leu Gly Ile Cys Val Trp Phe Val Val
705                 710                 715                 720

Asp Pro Ser His Ser Val Val Asp Phe Gln Asp Gln Arg Thr Leu Asp
                725                 730                 735

Pro Arg Phe Ala Arg Gly Val Leu Lys Cys Asp Ile Ser Asp Leu Ser
            740                 745                 750

Leu Ile Cys Leu Leu Gly Tyr Ser Met Leu Leu Met Val Thr Cys Thr
            755                 760                 765

Val Tyr Ala Ile Lys Thr Arg Gly Val Pro Glu Thr Phe Asn Glu Ala
770                 775                 780

Lys Pro Ile Gly Phe Thr Met Tyr Thr Thr Cys Ile Val Trp Leu Ala
785                 790                 795                 800

Phe Ile Pro Ile Phe Phe Gly Thr Ser Gln Ser Ala Asp Lys Leu Tyr
                805                 810                 815

Ile Gln Thr Thr Thr Leu Thr Val Ser Val Ser Leu Ser Ala Ser Val
                820                 825                 830

Ser Leu Gly Met Leu Tyr Met Pro Lys Val Tyr Ile Ile Leu Phe His
            835                 840                 845

Pro Glu Gln Asn Val Pro Lys Arg Lys Arg Ser Leu Lys Ala Val Val
850                 855                 860

Thr Ala Ala Thr Met Ser Asn Lys Phe Thr Gln Lys Gly Asn Phe Arg
865                 870                 875                 880

Pro Asn Gly Glu Ala Lys Ser Glu Leu Cys Glu Asn Leu Glu Ala Pro
                885                 890                 895

Ala Leu Ala Thr Lys Gln Thr Tyr Val Thr Tyr Thr Asn His Ala Ile
            900                 905                 910

<210> SEQ ID NO 11
<211> LENGTH: 1212
<212> TYPE: PRT
<213> ORGANISM: Homo sapiens

<400> SEQUENCE: 11

Met Val Leu Leu Leu Ile Leu Ser Val Leu Leu Leu Lys Glu Asp Val
1               5                   10                  15

Arg Gly Ser Ala Gln Ser Ser Glu Arg Arg Val Val Ala His Met Pro
            20                  25                  30

Gly Asp Ile Ile Ile Gly Ala Leu Phe Ser Val His His Gln Pro Thr
            35                  40                  45

Val Asp Lys Val His Glu Arg Lys Cys Gly Ala Val Arg Glu Gln Tyr
        50                  55                  60

Gly Ile Gln Arg Val Glu Ala Met Leu His Thr Leu Glu Arg Ile Asn
65                  70                  75                  80
```

```
Ser Asp Pro Thr Leu Leu Pro Asn Ile Thr Leu Gly Cys Glu Ile Arg
                85                  90                  95

Asp Ser Cys Trp His Ser Ala Val Ala Leu Glu Gln Ser Ile Glu Phe
            100                 105                 110

Ile Arg Asp Ser Leu Ile Ser Ser Glu Glu Glu Gly Leu Val Arg
        115                 120                 125

Cys Val Asp Gly Ser Ser Ser Phe Arg Ser Lys Lys Pro Ile Val
    130                 135                 140

Gly Val Ile Gly Pro Gly Ser Ser Val Ala Ile Gln Val Gln Asn
145                 150                 155                 160

Leu Leu Gln Leu Phe Asn Ile Pro Gln Ile Ala Tyr Ser Ala Thr Ser
                165                 170                 175

Met Asp Leu Ser Asp Lys Thr Leu Phe Lys Tyr Phe Met Arg Val Val
            180                 185                 190

Pro Ser Asp Ala Gln Gln Ala Arg Ala Met Val Asp Ile Val Lys Arg
        195                 200                 205

Tyr Asn Trp Thr Tyr Val Ser Ala Val His Thr Glu Gly Asn Tyr Gly
    210                 215                 220

Glu Ser Gly Met Glu Ala Phe Lys Asp Met Ser Ala Lys Glu Gly Ile
225                 230                 235                 240

Cys Ile Ala His Ser Tyr Lys Ile Tyr Ser Asn Ala Gly Glu Gln Ser
                245                 250                 255

Phe Asp Lys Leu Leu Lys Lys Leu Thr Ser His Leu Pro Lys Ala Arg
            260                 265                 270

Val Val Ala Cys Phe Cys Glu Gly Met Thr Val Arg Gly Leu Leu Met
        275                 280                 285

Ala Met Arg Arg Leu Gly Leu Ala Gly Glu Phe Leu Leu Leu Gly Ser
    290                 295                 300

Asp Gly Trp Ala Asp Arg Tyr Asp Val Thr Asp Gly Tyr Gln Arg Glu
305                 310                 315                 320

Ala Val Gly Gly Ile Thr Ile Lys Leu Gln Ser Pro Asp Val Lys Trp
                325                 330                 335

Phe Asp Asp Tyr Tyr Leu Lys Leu Arg Pro Glu Thr Asn His Arg Asn
            340                 345                 350

Pro Trp Phe Gln Glu Phe Trp Gln His Arg Phe Gln Cys Arg Leu Glu
        355                 360                 365

Gly Phe Pro Gln Glu Asn Ser Lys Tyr Asn Lys Thr Cys Asn Ser Ser
    370                 375                 380

Leu Thr Leu Lys Thr His His Val Gln Asp Ser Lys Met Gly Phe Val
385                 390                 395                 400

Ile Asn Ala Ile Tyr Ser Met Ala Tyr Gly Leu His Asn Met Gln Met
                405                 410                 415

Ser Leu Cys Pro Gly Tyr Ala Gly Leu Cys Asp Ala Met Lys Pro Ile
            420                 425                 430

Asp Gly Arg Lys Leu Leu Glu Ser Leu Met Lys Thr Asn Phe Thr Gly
        435                 440                 445

Val Ser Gly Asp Thr Ile Leu Phe Asp Glu Asn Gly Asp Ser Pro Gly
    450                 455                 460

Arg Tyr Glu Ile Met Asn Phe Lys Glu Met Gly Lys Asp Tyr Phe Asp
465                 470                 475                 480

Tyr Ile Asn Val Gly Ser Trp Asp Asn Gly Glu Leu Lys Met Asp Asp
                485                 490                 495

Asp Glu Val Trp Ser Lys Lys Ser Asn Ile Ile Arg Ser Val Cys Ser
```

```
                500             505             510
Glu Pro Cys Glu Lys Gly Gln Ile Lys Val Ile Arg Lys Gly Glu Val
            515                 520                 525
Ser Cys Cys Trp Thr Cys Thr Pro Cys Lys Glu Asn Glu Tyr Val Phe
            530                 535                 540
Asp Glu Tyr Thr Cys Lys Ala Cys Gln Leu Gly Ser Trp Pro Thr Asp
545                 550                 555                 560
Asp Leu Thr Gly Cys Asp Leu Ile Pro Val Gln Tyr Leu Arg Trp Gly
                565                 570                 575
Asp Pro Glu Pro Ile Ala Ala Val Val Phe Ala Cys Leu Gly Leu Leu
            580                 585                 590
Ala Thr Leu Phe Val Thr Val Val Phe Ile Ile Tyr Arg Asp Thr Pro
            595                 600                 605
Val Val Lys Ser Ser Arg Glu Leu Cys Tyr Ile Ile Leu Ala Gly
            610                 615                 620
Ile Cys Leu Gly Tyr Leu Cys Thr Phe Cys Leu Ile Ala Lys Pro Lys
625                 630                 635                 640
Gln Ile Tyr Cys Tyr Leu Gln Arg Ile Gly Ile Gly Leu Ser Pro Ala
                645                 650                 655
Met Ser Tyr Ser Ala Leu Val Thr Lys Thr Asn Arg Ile Ala Arg Ile
            660                 665                 670
Leu Ala Gly Ser Lys Lys Lys Ile Cys Thr Lys Lys Pro Arg Phe Met
            675                 680                 685
Ser Ala Cys Ala Gln Leu Val Ile Ala Phe Ile Leu Ile Cys Ile Gln
            690                 695                 700
Leu Gly Ile Ile Val Ala Leu Phe Ile Met Glu Pro Pro Asp Ile Met
705                 710                 715                 720
His Asp Tyr Pro Ser Ile Arg Glu Val Tyr Leu Ile Cys Asn Thr Thr
                725                 730                 735
Asn Leu Gly Val Val Thr Pro Leu Gly Tyr Asn Gly Leu Leu Ile Leu
            740                 745                 750
Ser Cys Thr Phe Tyr Ala Phe Lys Thr Arg Asn Val Pro Ala Asn Phe
            755                 760                 765
Asn Glu Ala Lys Tyr Ile Ala Phe Thr Met Tyr Thr Thr Cys Ile Ile
770                 775                 780
Trp Leu Ala Phe Val Pro Ile Tyr Phe Gly Ser Asn Tyr Lys Ile Ile
785                 790                 795                 800
Thr Met Cys Phe Ser Val Ser Leu Ser Ala Thr Val Ala Leu Gly Cys
                805                 810                 815
Met Phe Val Pro Lys Val Tyr Ile Ile Leu Ala Lys Pro Glu Arg Asn
            820                 825                 830
Val Arg Ser Ala Phe Thr Thr Ser Thr Val Val Arg Met His Val Gly
            835                 840                 845
Asp Gly Lys Ser Ser Ser Ala Ala Ser Arg Ser Ser Leu Val Asn
            850                 855                 860
Leu Trp Lys Arg Arg Gly Ser Ser Gly Glu Thr Leu Arg Tyr Lys Asp
865                 870                 875                 880
Arg Arg Leu Ala Gln His Lys Ser Glu Ile Glu Cys Phe Thr Pro Lys
                885                 890                 895
Gly Ser Met Gly Asn Gly Gly Arg Ala Thr Met Ser Ser Ser Asn Gly
            900                 905                 910
Lys Ser Val Thr Trp Ala Gln Asn Glu Lys Ser Ser Arg Gly Gln His
            915                 920                 925
```

```
Leu Trp Gln Arg Leu Ser Ile His Ile Asn Lys Lys Glu Asn Pro Asn
            930                 935                 940

Gln Thr Ala Val Ile Lys Pro Phe Pro Lys Ser Thr Glu Ser Arg Gly
945                 950                 955                 960

Leu Gly Ala Gly Ala Gly Ala Gly Gly Ser Ala Gly Gly Val Gly Ala
                965                 970                 975

Thr Gly Gly Ala Gly Cys Ala Gly Ala Gly Pro Gly Gly Pro Glu Ser
                980                 985                 990

Pro Asp Ala Gly Pro Lys Ala Leu Tyr Asp Val Ala Glu  Ala Glu Glu
            995                 1000                1005

His Phe Pro Ala Pro Ala Arg  Pro Arg Ser Pro Ser  Pro Ile Ser
    1010                1015                1020

Thr Leu Ser His Arg Ala Gly  Ser Ala Ser Arg Thr  Asp Asp Asp
    1025                1030                1035

Val Pro Ser Leu His Ser Glu  Pro Val Ala Arg Ser  Ser Ser Ser
    1040                1045                1050

Gln Gly Ser Leu Met Glu Gln  Ile Ser Ser Val Val  Thr Arg Phe
    1055                1060                1065

Thr Ala Asn Ile Ser Glu Leu  Asn Ser Met Met Leu  Ser Thr Ala
    1070                1075                1080

Ala Pro Ser Pro Gly Val Gly  Ala Pro Leu Cys Ser  Ser Tyr Leu
    1085                1090                1095

Ile Pro Lys Glu Ile Gln Leu  Pro Thr Thr Met Thr  Thr Phe Ala
    1100                1105                1110

Glu Ile Gln Pro Leu Pro Ala  Ile Glu Val Thr Gly  Gly Ala Gln
    1115                1120                1125

Pro Ala Ala Gly Ala Gln Ala  Ala Gly Asp Ala Ala  Arg Glu Ser
    1130                1135                1140

Pro Ala Ala Gly Pro Glu Ala  Ala Ala Lys Pro Asp  Leu Glu
    1145                1150                1155

Glu Leu Val Ala Leu Thr Pro  Pro Ser Pro Phe Arg  Asp Ser Val
    1160                1165                1170

Asp Ser Gly Ser Thr Thr Pro  Asn Ser Pro Val Ser  Glu Ser Ala
    1175                1180                1185

Leu Cys Ile Pro Ser Ser Pro  Lys Tyr Asp Thr Leu  Ile Ile Arg
    1190                1195                1200

Asp Tyr Thr Gln Ser Ser Ser  Ser Leu
    1205                1210

<210> SEQ ID NO 12
<211> LENGTH: 877
<212> TYPE: PRT
<213> ORGANISM: Homo sapiens

<400> SEQUENCE: 12

Met Ala Arg Pro Arg Ala Arg Glu Pro Leu Leu Val Ala Leu Leu
1               5                   10                  15

Pro Leu Ala Trp Leu Ala Gln Ala Gly Leu Ala Arg Ala Ala Gly Ser
                20                  25                  30

Val Arg Leu Ala Gly Gly Leu Thr Leu Gly Gly Leu Phe Pro Val His
            35                  40                  45

Ala Arg Gly Ala Ala Gly Arg Ala Cys Gly Gln Leu Lys Lys Glu Gln
        50                  55                  60

Gly Val His Arg Leu Glu Ala Met Leu Tyr Ala Leu Asp Arg Val Asn
65                  70                  75                  80
```

```
Ala Asp Pro Glu Leu Leu Pro Gly Val Arg Leu Gly Ala Arg Leu Leu
                85                  90                  95

Asp Thr Cys Ser Arg Asp Thr Tyr Ala Leu Glu Gln Ala Leu Ser Phe
                100                 105                 110

Val Gln Ala Leu Ile Arg Gly Arg Gly Asp Gly Asp Glu Val Gly Val
            115                 120                 125

Arg Cys Pro Gly Gly Val Pro Pro Leu Arg Pro Ala Pro Pro Glu Arg
            130                 135                 140

Val Val Ala Val Val Gly Ala Ser Ala Ser Ser Val Ser Ile Met Val
145                 150                 155                 160

Ala Asn Val Leu Arg Leu Phe Ala Ile Pro Gln Ile Ser Tyr Ala Ser
                165                 170                 175

Thr Ala Pro Glu Leu Ser Asp Ser Thr Arg Tyr Asp Phe Phe Ser Arg
                180                 185                 190

Val Val Pro Pro Asp Ser Tyr Gln Ala Gln Ala Met Val Asp Ile Val
            195                 200                 205

Arg Ala Leu Gly Trp Asn Tyr Val Ser Thr Leu Ala Ser Glu Gly Asn
210                 215                 220

Tyr Gly Glu Ser Gly Val Glu Ala Phe Val Gln Ile Ser Arg Glu Ala
225                 230                 235                 240

Gly Gly Val Cys Ile Ala Gln Ser Ile Lys Ile Pro Arg Glu Pro Lys
                245                 250                 255

Pro Gly Glu Phe Ser Lys Val Ile Arg Arg Leu Met Glu Thr Pro Asn
                260                 265                 270

Ala Arg Gly Ile Ile Ile Phe Ala Asn Glu Asp Asp Ile Arg Arg Val
            275                 280                 285

Leu Glu Ala Ala Arg Gln Ala Asn Leu Thr Gly His Phe Leu Trp Val
290                 295                 300

Gly Ser Asp Ser Trp Gly Ala Lys Thr Ser Pro Ile Leu Ser Leu Glu
305                 310                 315                 320

Asp Val Ala Val Gly Ala Ile Thr Ile Leu Pro Lys Arg Ala Ser Ile
                325                 330                 335

Asp Gly Phe Asp Gln Tyr Phe Met Thr Arg Ser Leu Glu Asn Asn Arg
                340                 345                 350

Arg Asn Ile Trp Phe Ala Glu Phe Trp Glu Glu Asn Phe Asn Cys Lys
            355                 360                 365

Leu Thr Ser Ser Gly Thr Gln Ser Asp Asp Ser Thr Arg Lys Cys Thr
370                 375                 380

Gly Glu Glu Arg Ile Gly Arg Asp Ser Thr Tyr Glu Gln Glu Gly Lys
385                 390                 395                 400

Val Gln Phe Val Ile Asp Ala Val Tyr Ala Ile Ala His Ala Leu His
                405                 410                 415

Ser Met His Gln Ala Leu Cys Pro Gly His Thr Gly Leu Cys Pro Ala
                420                 425                 430

Met Glu Pro Thr Asp Gly Arg Met Leu Leu Gln Tyr Ile Arg Ala Val
            435                 440                 445

Arg Phe Asn Gly Ser Ala Gly Thr Pro Val Met Phe Asn Glu Asn Gly
450                 455                 460

Asp Ala Pro Gly Arg Tyr Asp Ile Phe Gln Tyr Gln Ala Thr Asn Gly
465                 470                 475                 480

Ser Ala Ser Ser Gly Gly Tyr Gln Ala Val Gly Gln Trp Ala Glu Thr
                485                 490                 495

Leu Arg Leu Asp Val Glu Ala Leu Gln Trp Ser Gly Asp Pro His Glu
                500                 505                 510
```

Val Pro Ser Ser Leu Cys Ser Leu Pro Cys Gly Pro Gly Glu Arg Lys
            515                 520                 525

Lys Met Val Lys Gly Val Pro Cys Cys Trp His Cys Glu Ala Cys Asp
        530                 535                 540

Gly Tyr Arg Phe Gln Val Asp Glu Phe Thr Cys Glu Ala Cys Pro Gly
545                 550                 555                 560

Asp Met Arg Pro Thr Pro Asn His Thr Gly Cys Arg Pro Thr Pro Val
                565                 570                 575

Val Arg Leu Ser Trp Ser Ser Pro Trp Ala Ala Pro Pro Leu Leu Leu
            580                 585                 590

Ala Val Leu Gly Ile Val Ala Thr Thr Thr Val Val Ala Thr Phe Val
        595                 600                 605

Arg Tyr Asn Asn Thr Pro Ile Val Arg Ala Ser Gly Arg Glu Leu Ser
610                 615                 620

Tyr Val Leu Leu Thr Gly Ile Phe Leu Ile Tyr Ala Ile Thr Phe Leu
625                 630                 635                 640

Met Val Ala Glu Pro Gly Ala Ala Val Cys Ala Ala Arg Arg Leu Phe
                645                 650                 655

Leu Gly Leu Gly Thr Thr Leu Ser Tyr Ser Ala Leu Leu Thr Lys Thr
            660                 665                 670

Asn Arg Ile Tyr Arg Ile Phe Glu Gln Gly Lys Arg Ser Val Thr Pro
        675                 680                 685

Pro Pro Phe Ile Ser Pro Thr Ser Gln Leu Val Ile Thr Phe Ser Leu
690                 695                 700

Thr Ser Leu Gln Val Val Gly Met Ile Ala Trp Leu Gly Ala Arg Pro
705                 710                 715                 720

Pro His Ser Val Ile Asp Tyr Glu Glu Gln Arg Thr Val Asp Pro Glu
                725                 730                 735

Gln Ala Arg Gly Val Leu Lys Cys Asp Met Ser Asp Leu Ser Leu Ile
            740                 745                 750

Gly Cys Leu Gly Tyr Ser Leu Leu Leu Met Val Thr Cys Thr Val Tyr
        755                 760                 765

Ala Ile Lys Ala Arg Gly Val Pro Glu Thr Phe Asn Glu Ala Lys Pro
770                 775                 780

Ile Gly Phe Thr Met Tyr Thr Thr Cys Ile Ile Trp Leu Ala Phe Val
785                 790                 795                 800

Pro Ile Phe Phe Gly Thr Ala Gln Ser Ala Glu Lys Ile Tyr Ile Gln
                805                 810                 815

Thr Thr Thr Leu Thr Val Ser Leu Ser Leu Ser Ala Ser Val Ser Leu
            820                 825                 830

Gly Met Leu Tyr Val Pro Lys Thr Tyr Val Ile Leu Phe His Pro Glu
        835                 840                 845

Gln Asn Val Gln Lys Arg Lys Arg Ser Leu Lys Ala Thr Ser Thr Val
850                 855                 860

Ala Ala Pro Pro Lys Gly Glu Asp Ala Glu Ala His Lys
865                 870                 875

<210> SEQ ID NO 13
<211> LENGTH: 915
<212> TYPE: PRT
<213> ORGANISM: Homo sapiens

<400> SEQUENCE: 13

Met Val Gln Leu Arg Lys Leu Leu Arg Val Leu Thr Leu Met Lys Phe
1               5                   10                  15

```
Pro Cys Cys Val Leu Glu Val Leu Leu Cys Ala Leu Ala Ala Ala
            20                  25                  30

Arg Gly Gln Glu Met Tyr Ala Pro His Ser Ile Arg Ile Glu Gly Asp
            35                  40                  45

Val Thr Leu Gly Gly Leu Phe Pro Val His Ala Lys Gly Pro Ser Gly
        50                  55                  60

Val Pro Cys Gly Asp Ile Lys Arg Glu Asn Gly Ile His Arg Leu Glu
65                  70                  75                  80

Ala Met Leu Tyr Ala Leu Asp Gln Ile Asn Ser Asp Pro Asn Leu Leu
                85                  90                  95

Pro Asn Val Thr Leu Gly Ala Arg Ile Leu Asp Thr Cys Ser Arg Asp
                100                 105                 110

Thr Tyr Ala Leu Glu Gln Ser Leu Thr Phe Val Gln Ala Leu Ile Gln
            115                 120                 125

Lys Asp Thr Ser Asp Val Arg Cys Thr Asn Gly Glu Pro Pro Val Phe
        130                 135                 140

Val Lys Pro Glu Lys Val Val Gly Val Ile Gly Ala Ser Gly Ser Ser
145                 150                 155                 160

Val Ser Ile Met Val Ala Asn Ile Leu Arg Leu Phe Gln Ile Pro Gln
                165                 170                 175

Ile Ser Tyr Ala Ser Thr Ala Pro Glu Leu Ser Asp Asp Arg Arg Tyr
                180                 185                 190

Asp Phe Phe Ser Arg Val Val Pro Pro Asp Ser Phe Gln Ala Gln Ala
            195                 200                 205

Met Val Asp Ile Val Lys Ala Leu Gly Trp Asn Tyr Val Ser Thr Leu
        210                 215                 220

Ala Ser Glu Gly Ser Tyr Gly Glu Lys Gly Val Glu Ser Phe Thr Gln
225                 230                 235                 240

Ile Ser Lys Glu Ala Gly Gly Leu Cys Ile Ala Gln Ser Val Arg Ile
                245                 250                 255

Pro Gln Glu Arg Lys Asp Arg Thr Ile Asp Phe Asp Arg Ile Ile Lys
            260                 265                 270

Gln Leu Leu Asp Thr Pro Asn Ser Arg Ala Val Val Ile Phe Ala Asn
        275                 280                 285

Asp Glu Asp Ile Lys Gln Ile Leu Ala Ala Ala Lys Arg Ala Asp Gln
        290                 295                 300

Val Gly His Phe Leu Trp Val Gly Ser Asp Ser Trp Gly Ser Lys Ile
305                 310                 315                 320

Asn Pro Leu His Gln His Glu Asp Ile Ala Glu Gly Ala Ile Thr Ile
                325                 330                 335

Gln Pro Lys Arg Ala Thr Val Glu Gly Phe Asp Ala Tyr Phe Thr Ser
            340                 345                 350

Arg Thr Leu Glu Asn Asn Arg Arg Asn Val Trp Phe Ala Glu Tyr Trp
        355                 360                 365

Glu Glu Asn Phe Asn Cys Lys Leu Thr Ile Ser Gly Ser Lys Lys Glu
        370                 375                 380

Asp Thr Asp Arg Lys Cys Thr Gly Gln Glu Arg Ile Gly Lys Asp Ser
385                 390                 395                 400

Asn Tyr Glu Gln Glu Gly Lys Val Gln Phe Val Ile Asp Ala Val Tyr
                405                 410                 415

Ala Met Ala His Ala Leu His His Met Asn Lys Asp Leu Cys Ala Asp
            420                 425                 430

Tyr Arg Gly Val Cys Pro Glu Met Glu Gln Ala Gly Gly Lys Lys Leu
```

```
                    435                 440                 445
Leu Lys Tyr Ile Arg Asn Val Asn Phe Asn Gly Ser Ala Gly Thr Pro
450                 455                 460

Val Met Phe Asn Lys Asn Gly Asp Ala Pro Gly Arg Tyr Asp Ile Phe
465                 470                 475                 480

Gln Tyr Gln Thr Thr Asn Thr Ser Asn Pro Gly Tyr Arg Leu Ile Gly
                    485                 490                 495

Gln Trp Thr Asp Glu Leu Gln Leu Asn Ile Glu Asp Met Gln Trp Gly
                500                 505                 510

Lys Gly Val Arg Glu Ile Pro Ala Ser Val Cys Thr Leu Pro Cys Lys
            515                 520                 525

Pro Gly Gln Arg Lys Lys Thr Gln Lys Gly Thr Pro Cys Cys Trp Thr
530                 535                 540

Cys Glu Pro Cys Asp Gly Tyr Gln Tyr Gln Phe Asp Glu Met Thr Cys
545                 550                 555                 560

Gln His Cys Pro Tyr Asp Gln Arg Pro Asn Glu Asn Arg Thr Gly Cys
                565                 570                 575

Gln Asp Ile Pro Ile Ile Lys Leu Glu Trp His Ser Pro Trp Ala Val
                580                 585                 590

Ile Pro Val Phe Leu Ala Met Leu Gly Ile Ile Ala Thr Ile Phe Val
                595                 600                 605

Met Ala Thr Phe Ile Arg Tyr Asn Asp Thr Pro Ile Val Arg Ala Ser
            610                 615                 620

Gly Arg Glu Leu Ser Tyr Val Leu Leu Thr Gly Ile Phe Leu Cys Tyr
625                 630                 635                 640

Ile Ile Thr Phe Leu Met Ile Ala Lys Pro Asp Val Ala Val Cys Ser
                645                 650                 655

Phe Arg Arg Val Phe Leu Gly Leu Gly Met Cys Ile Ser Tyr Ala Ala
                660                 665                 670

Leu Leu Thr Lys Thr Asn Arg Ile Tyr Arg Ile Phe Glu Gln Gly Lys
                675                 680                 685

Lys Ser Val Thr Ala Pro Arg Leu Ile Ser Pro Thr Ser Gln Leu Ala
690                 695                 700

Ile Thr Ser Ser Leu Ile Ser Val Gln Leu Leu Gly Val Phe Ile Trp
705                 710                 715                 720

Phe Gly Val Asp Pro Pro Asn Ile Ile Ile Asp Tyr Asp Glu His Lys
                725                 730                 735

Thr Met Asn Pro Glu Gln Ala Arg Gly Val Leu Lys Cys Asp Ile Thr
                740                 745                 750

Asp Leu Gln Ile Ile Cys Ser Leu Gly Tyr Ser Ile Leu Leu Met Val
                755                 760                 765

Thr Cys Thr Val Tyr Ala Ile Lys Thr Arg Gly Val Pro Glu Asn Phe
                770                 775                 780

Asn Glu Ala Lys Pro Ile Gly Phe Thr Met Tyr Thr Thr Cys Ile Val
785                 790                 795                 800

Trp Leu Ala Phe Ile Pro Ile Phe Phe Gly Thr Ala Gln Ser Ala Glu
                805                 810                 815

Lys Leu Tyr Ile Gln Thr Thr Thr Leu Thr Ile Ser Met Asn Leu Ser
                820                 825                 830

Ala Ser Val Ala Leu Gly Met Leu Tyr Met Pro Lys Val Tyr Ile Ile
            835                 840                 845

Ile Phe His Pro Glu Leu Asn Val Gln Lys Arg Lys Arg Ser Phe Lys
850                 855                 860
```

```
Ala Val Val Thr Ala Ala Thr Met Ser Ser Arg Leu Ser His Lys Pro
865                 870                 875                 880

Ser Asp Arg Pro Asn Gly Glu Ala Lys Thr Glu Leu Cys Glu Asn Val
            885                 890                 895

Asp Pro Asn Ser Pro Ala Lys Lys Lys Tyr Val Ser Tyr Asn Asn
            900                 905                 910

Leu Val Ile
        915

<210> SEQ ID NO 14
<211> LENGTH: 908
<212> TYPE: PRT
<213> ORGANISM: Homo sapiens

<400> SEQUENCE: 14

Met Val Cys Glu Gly Lys Arg Ser Ala Ser Cys Pro Cys Phe Phe Leu
1               5                   10                  15

Leu Thr Ala Lys Phe Tyr Trp Ile Leu Thr Met Met Gln Arg Thr His
            20                  25                  30

Ser Gln Glu Tyr Ala His Ser Ile Arg Val Asp Gly Asp Ile Ile Leu
        35                  40                  45

Gly Gly Leu Phe Pro Val His Ala Lys Gly Glu Arg Gly Val Pro Cys
    50                  55                  60

Gly Glu Leu Lys Lys Glu Lys Gly Ile His Arg Leu Glu Ala Met Leu
65                  70                  75                  80

Tyr Ala Ile Asp Gln Ile Asn Lys Asp Pro Asp Leu Leu Ser Asn Ile
                85                  90                  95

Thr Leu Gly Val Arg Ile Leu Asp Thr Cys Ser Arg Asp Thr Tyr Ala
            100                 105                 110

Leu Glu Gln Ser Leu Thr Phe Val Gln Ala Leu Ile Glu Lys Asp Ala
        115                 120                 125

Ser Asp Val Lys Cys Ala Asn Gly Asp Pro Pro Ile Phe Thr Lys Pro
    130                 135                 140

Asp Lys Ile Ser Gly Val Ile Gly Ala Ala Ala Ser Ser Val Ser Ile
145                 150                 155                 160

Met Val Ala Asn Ile Leu Arg Leu Phe Lys Ile Pro Gln Ile Ser Tyr
                165                 170                 175

Ala Ser Thr Ala Pro Glu Leu Ser Asp Asn Thr Arg Tyr Asp Phe Phe
            180                 185                 190

Ser Arg Val Val Pro Pro Asp Ser Tyr Gln Ala Gln Ala Met Val Asp
        195                 200                 205

Ile Val Thr Ala Leu Gly Trp Asn Tyr Val Ser Thr Leu Ala Ser Glu
    210                 215                 220

Gly Asn Tyr Gly Glu Ser Gly Val Glu Ala Phe Thr Gln Ile Ser Arg
225                 230                 235                 240

Glu Ile Gly Gly Val Cys Ile Ala Gln Ser Gln Lys Ile Pro Arg Glu
                245                 250                 255

Pro Arg Pro Gly Glu Phe Glu Lys Ile Ile Lys Arg Leu Leu Glu Thr
            260                 265                 270

Pro Asn Ala Arg Ala Val Ile Met Phe Ala Asn Glu Asp Asp Ile Arg
        275                 280                 285

Arg Ile Leu Glu Ala Ala Lys Lys Leu Asn Gln Ser Gly His Phe Leu
    290                 295                 300

Trp Ile Gly Ser Asp Ser Trp Gly Ser Lys Ile Ala Pro Val Tyr Gln
305                 310                 315                 320
```

```
Gln Glu Glu Ile Ala Glu Gly Ala Val Thr Ile Leu Pro Lys Arg Ala
                325                 330                 335

Ser Ile Asp Gly Phe Asp Arg Tyr Phe Arg Ser Arg Thr Leu Ala Asn
            340                 345                 350

Asn Arg Arg Asn Val Trp Phe Ala Glu Phe Trp Glu Glu Asn Phe Gly
        355                 360                 365

Cys Lys Leu Gly Ser His Gly Lys Arg Asn Ser His Ile Lys Lys Cys
    370                 375                 380

Thr Gly Leu Glu Arg Ile Ala Arg Asp Ser Ser Tyr Glu Gln Glu Gly
385                 390                 395                 400

Lys Val Gln Phe Val Ile Asp Ala Val Tyr Ser Met Ala Tyr Ala Leu
                405                 410                 415

His Asn Met His Lys Asp Leu Cys Pro Gly Tyr Ile Gly Leu Cys Pro
            420                 425                 430

Arg Met Ser Thr Ile Asp Gly Lys Glu Leu Leu Gly Tyr Ile Arg Ala
        435                 440                 445

Val Asn Phe Asn Gly Ser Ala Gly Thr Pro Val Thr Phe Asn Glu Asn
    450                 455                 460

Gly Asp Ala Pro Gly Arg Tyr Asp Ile Phe Gln Tyr Gln Ile Thr Asn
465                 470                 475                 480

Lys Ser Thr Glu Tyr Lys Val Ile Gly His Trp Thr Asn Gln Leu His
                485                 490                 495

Leu Lys Val Glu Asp Met Gln Trp Ala His Arg Glu His Thr His Pro
            500                 505                 510

Ala Ser Val Cys Ser Leu Pro Cys Lys Pro Gly Glu Arg Lys Lys Thr
        515                 520                 525

Val Lys Gly Val Pro Cys Cys Trp His Cys Glu Arg Cys Glu Gly Tyr
    530                 535                 540

Asn Tyr Gln Val Asp Glu Leu Ser Cys Glu Leu Cys Pro Leu Asp Gln
545                 550                 555                 560

Arg Pro Asn Met Asn Arg Thr Gly Cys Gln Leu Ile Pro Ile Ile Lys
                565                 570                 575

Leu Glu Trp His Ser Pro Trp Ala Val Val Pro Val Phe Val Ala Ile
            580                 585                 590

Leu Gly Ile Ile Ala Thr Thr Phe Val Ile Val Thr Phe Val Arg Tyr
        595                 600                 605

Asn Asp Thr Pro Ile Val Arg Ala Ser Gly Arg Glu Leu Ser Tyr Val
    610                 615                 620

Leu Leu Thr Gly Ile Phe Leu Cys Tyr Ser Ile Thr Phe Leu Met Ile
625                 630                 635                 640

Ala Ala Pro Asp Thr Ile Ile Cys Ser Phe Arg Arg Val Phe Leu Gly
                645                 650                 655

Leu Gly Met Cys Phe Ser Tyr Ala Ala Leu Leu Thr Lys Thr Asn Arg
            660                 665                 670

Ile His Arg Ile Phe Glu Gln Gly Lys Lys Ser Val Thr Ala Pro Lys
        675                 680                 685

Phe Ile Ser Pro Ala Ser Gln Leu Val Ile Thr Phe Ser Leu Ile Ser
    690                 695                 700

Val Gln Leu Leu Gly Val Phe Val Trp Phe Val Val Asp Pro Pro His
705                 710                 715                 720

Ile Ile Ile Asp Tyr Gly Glu Gln Arg Thr Leu Asp Pro Glu Lys Ala
                725                 730                 735

Arg Gly Val Leu Lys Cys Asp Ile Ser Asp Leu Ser Leu Ile Cys Ser
            740                 745                 750
```

```
Leu Gly Tyr Ser Ile Leu Leu Met Val Thr Cys Thr Val Tyr Ala Ile
            755                 760                 765

Lys Thr Arg Gly Val Pro Glu Thr Phe Asn Glu Ala Lys Pro Ile Gly
    770                 775                 780

Phe Thr Met Tyr Thr Thr Cys Ile Ile Trp Leu Ala Phe Ile Pro Ile
785                 790                 795                 800

Phe Phe Gly Thr Ala Gln Ser Ala Glu Lys Met Tyr Ile Gln Thr Thr
                805                 810                 815

Thr Leu Thr Val Ser Met Ser Leu Ser Ala Ser Val Ser Leu Gly Met
            820                 825                 830

Leu Tyr Met Pro Lys Val Tyr Ile Ile Phe His Pro Glu Gln Asn
            835                 840                 845

Val Gln Lys Arg Lys Arg Ser Phe Lys Ala Val Thr Ala Ala Thr
    850                 855                 860

Met Gln Ser Lys Leu Ile Gln Lys Gly Asn Asp Arg Pro Asn Gly Glu
865                 870                 875                 880

Val Lys Ser Glu Leu Cys Glu Ser Leu Glu Thr Asn Thr Ser Ser Thr
                885                 890                 895

Lys Thr Thr Tyr Ile Ser Tyr Ser Asn His Ser Ile
            900                 905
```

<210> SEQ ID NO 15
<211> LENGTH: 1078
<212> TYPE: PRT
<213> ORGANISM: Homo sapiens

<400> SEQUENCE: 15

```
Met Ala Phe Tyr Ser Cys Cys Trp Val Leu Leu Ala Leu Thr Trp His
1               5                   10                  15

Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Ser Arg Leu Leu Ser Asn
                165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Asp Tyr Gly Arg Pro Gly Ile Glu
    210                 215                 220
```

-continued

Lys Phe Arg Glu Glu Ala Glu Arg Asp Ile Cys Ile Asp Phe Ser
225                 230                 235                 240

Glu Leu Ile Ser Gln Tyr Ser Asp Glu Glu Ile Gln His Val Val
            245                 250                 255

Glu Val Ile Gln Asn Ser Thr Ala Lys Val Ile Val Phe Ser Ser
                260                 265                 270

Gly Pro Asp Leu Glu Pro Leu Ile Lys Glu Ile Val Arg Arg Asn Ile
        275                 280                 285

Thr Gly Lys Ile Trp Leu Ala Ser Glu Ala Trp Ala Ser Ser Ser Leu
290                 295                 300

Ile Ala Met Pro Gln Tyr Phe His Val Val Gly Thr Ile Gly Phe
305                 310                 315                 320

Ala Leu Lys Ala Gly Gln Ile Pro Gly Phe Arg Glu Phe Leu Lys Lys
            325                 330                 335

Val His Pro Arg Lys Ser Val His Asn Gly Phe Ala Lys Glu Phe Trp
            340                 345                 350

Glu Glu Thr Phe Asn Cys His Leu Gln Glu Gly Ala Lys Gly Pro Leu
            355                 360                 365

Pro Val Asp Thr Phe Leu Arg Gly His Glu Glu Ser Gly Asp Arg Phe
    370                 375                 380

Ser Asn Ser Ser Thr Ala Phe Arg Pro Leu Cys Thr Gly Asp Glu Asn
385                 390                 395                 400

Ile Ser Ser Val Glu Thr Pro Tyr Ile Asp Tyr Thr His Leu Arg Ile
                405                 410                 415

Ser Tyr Asn Val Tyr Leu Ala Val Tyr Ser Ile Ala His Ala Leu Gln
            420                 425                 430

Asp Ile Tyr Thr Cys Leu Pro Gly Arg Gly Leu Phe Thr Asn Gly Ser
            435                 440                 445

Cys Ala Asp Ile Lys Lys Val Glu Ala Trp Gln Val Leu Lys His Leu
450                 455                 460

Arg His Leu Asn Phe Thr Asn Asn Met Gly Glu Gln Val Thr Phe Asp
465                 470                 475                 480

Glu Cys Gly Asp Leu Val Gly Asn Tyr Ser Ile Ile Asn Trp His Leu
                485                 490                 495

Ser Pro Glu Asp Gly Ser Ile Val Phe Lys Glu Val Gly Tyr Tyr Asn
            500                 505                 510

Val Tyr Ala Lys Lys Gly Glu Arg Leu Phe Ile Asn Glu Glu Lys Ile
            515                 520                 525

Leu Trp Ser Gly Phe Ser Arg Glu Val Pro Phe Ser Asn Cys Ser Arg
530                 535                 540

Asp Cys Leu Ala Gly Thr Arg Lys Gly Ile Ile Glu Gly Glu Pro Thr
545                 550                 555                 560

Cys Cys Phe Glu Cys Val Glu Cys Pro Asp Gly Glu Tyr Ser Asp Glu
                565                 570                 575

Thr Asp Ala Ser Ala Cys Asn Lys Cys Pro Asp Asp Phe Trp Ser Asn
            580                 585                 590

Glu Asn His Thr Ser Cys Ile Ala Lys Glu Ile Glu Phe Leu Ser Trp
            595                 600                 605

Thr Glu Pro Phe Gly Ile Ala Leu Thr Leu Phe Ala Val Leu Gly Ile
    610                 615                 620

Phe Leu Thr Ala Phe Val Leu Gly Val Phe Ile Lys Phe Arg Asn Thr
625                 630                 635                 640

Pro Ile Val Lys Ala Thr Asn Arg Glu Leu Ser Tyr Leu Leu Leu Phe

```
                    645                 650                 655
Ser Leu Leu Cys Cys Phe Ser Ser Leu Phe Phe Ile Gly Glu Pro
            660                 665                 670

Gln Asp Trp Thr Cys Arg Leu Arg Gln Pro Ala Phe Gly Ile Ser Phe
        675                 680                 685

Val Leu Cys Ile Ser Cys Ile Leu Val Lys Thr Asn Arg Val Leu Leu
    690                 695                 700

Val Phe Glu Ala Lys Ile Pro Thr Ser Phe His Arg Lys Trp Trp Gly
705                 710                 715                 720

Leu Asn Leu Gln Phe Leu Leu Val Phe Leu Cys Thr Phe Met Gln Ile
                725                 730                 735

Val Ile Cys Val Ile Trp Leu Tyr Thr Ala Pro Pro Ser Ser Tyr Arg
            740                 745                 750

Asn Gln Glu Leu Glu Asp Glu Ile Ile Phe Ile Thr Cys His Glu Gly
                755                 760                 765

Ser Leu Met Ala Leu Gly Phe Leu Ile Gly Tyr Thr Cys Leu Leu Ala
            770                 775                 780

Ala Ile Cys Phe Phe Phe Ala Phe Lys Ser Arg Lys Leu Pro Glu Asn
785                 790                 795                 800

Phe Asn Glu Ala Lys Phe Ile Thr Phe Ser Met Leu Ile Phe Phe Ile
                805                 810                 815

Val Trp Ile Ser Phe Ile Pro Ala Tyr Ala Ser Thr Tyr Gly Lys Phe
            820                 825                 830

Val Ser Ala Val Glu Val Ile Ala Ile Leu Ala Ala Ser Phe Gly Leu
            835                 840                 845

Leu Ala Cys Ile Phe Phe Asn Lys Ile Tyr Ile Ile Leu Phe Lys Pro
        850                 855                 860

Ser Arg Asn Thr Ile Glu Glu Val Arg Cys Ser Thr Ala Ala His Ala
865                 870                 875                 880

Phe Lys Val Ala Ala Arg Ala Thr Leu Arg Arg Ser Asn Val Ser Arg
                885                 890                 895

Lys Arg Ser Ser Ser Leu Gly Gly Ser Thr Gly Ser Thr Pro Ser Ser
            900                 905                 910

Ser Ile Ser Ser Lys Ser Asn Ser Glu Asp Pro Phe Pro Gln Pro Glu
        915                 920                 925

Arg Gln Lys Gln Gln Gln Pro Leu Ala Leu Thr Gln Gln Glu Gln Gln
        930                 935                 940

Gln Gln Pro Leu Thr Leu Pro Gln Gln Arg Ser Gln Gln Gln Pro
945                 950                 955                 960

Arg Cys Lys Gln Lys Val Ile Phe Gly Ser Gly Thr Val Thr Phe Ser
            965                 970                 975

Leu Ser Phe Asp Glu Pro Gln Lys Asn Ala Met Ala His Arg Asn Ser
            980                 985                 990

Thr His Gln Asn Ser Leu Glu Ala Gln Lys Ser Ser Asp Thr Leu Thr
        995                 1000                1005

Arg His Gln Pro Leu Leu Pro Leu Gln Cys Gly Glu Thr Asp Leu
    1010                1015                1020

Asp Leu Thr Val Gln Glu Thr Gly Leu Gln Gly Pro Val Gly Gly
    1025                1030                1035

Asp Gln Arg Pro Glu Val Glu Asp Pro Glu Glu Leu Ser Pro Ala
    1040                1045                1050

Leu Val Val Ser Ser Ser Gln Ser Phe Val Ile Ser Gly Gly Gly
    1055                1060                1065
```

Ser Thr Val Thr Glu Asn Val Val Asn Ser
    1070                1075

<210> SEQ ID NO 16
<211> LENGTH: 961
<212> TYPE: PRT
<213> ORGANISM: Homo sapiens

<400> SEQUENCE: 16

Met Leu Leu Leu Leu Leu Ala Pro Leu Phe Leu Arg Pro Pro Gly
1               5                   10                  15

Ala Gly Gly Ala Gln Thr Pro Asn Ala Thr Ser Glu Gly Cys Gln Ile
            20                  25                  30

Ile His Pro Pro Trp Glu Gly Gly Ile Arg Tyr Arg Gly Leu Thr Arg
                35                  40                  45

Asp Gln Val Lys Ala Ile Asn Phe Leu Pro Val Asp Tyr Glu Ile Glu
        50                  55                  60

Tyr Val Cys Arg Gly Glu Arg Glu Val Val Gly Pro Lys Val Arg Lys
65                  70                  75                  80

Cys Leu Ala Asn Gly Ser Trp Thr Asp Met Asp Thr Pro Ser Arg Cys
                85                  90                  95

Val Arg Ile Cys Ser Lys Ser Tyr Leu Thr Leu Glu Asn Gly Lys Val
            100                 105                 110

Phe Leu Thr Gly Gly Asp Leu Pro Ala Leu Asp Gly Ala Arg Val Asp
        115                 120                 125

Phe Arg Cys Asp Pro Asp Phe His Leu Val Gly Ser Ser Arg Ser Ile
    130                 135                 140

Cys Ser Gln Gly Gln Trp Ser Thr Pro Lys Pro His Cys Gln Val Asn
145                 150                 155                 160

Arg Thr Pro His Ser Glu Arg Arg Ala Val Tyr Ile Gly Ala Leu Phe
                165                 170                 175

Pro Met Ser Gly Gly Trp Pro Gly Gly Gln Ala Cys Gln Pro Ala Val
            180                 185                 190

Glu Met Ala Leu Glu Asp Val Asn Ser Arg Arg Asp Ile Leu Pro Asp
        195                 200                 205

Tyr Glu Leu Lys Leu Ile His His Asp Ser Lys Cys Asp Pro Gly Gln
    210                 215                 220

Ala Thr Lys Tyr Leu Tyr Glu Leu Leu Tyr Asn Asp Pro Ile Lys Ile
225                 230                 235                 240

Ile Leu Met Pro Gly Cys Ser Ser Val Ser Thr Leu Val Ala Glu Ala
                245                 250                 255

Ala Arg Met Trp Asn Leu Ile Val Leu Ser Tyr Gly Ser Ser Ser Pro
            260                 265                 270

Ala Leu Ser Asn Arg Gln Arg Phe Pro Thr Phe Phe Arg Thr His Pro
        275                 280                 285

Ser Ala Thr Leu His Asn Pro Thr Arg Val Lys Leu Phe Glu Lys Trp
    290                 295                 300

Gly Trp Lys Lys Ile Ala Thr Ile Gln Gln Thr Thr Glu Val Phe Thr
305                 310                 315                 320

Ser Thr Leu Asp Asp Leu Glu Glu Arg Val Lys Glu Ala Gly Ile Glu
                325                 330                 335

Ile Thr Phe Arg Gln Ser Phe Phe Ser Asp Pro Ala Val Pro Val Lys
            340                 345                 350

Asn Leu Lys Arg Gln Asp Ala Arg Ile Ile Val Gly Leu Phe Tyr Glu
        355                 360                 365

-continued

```
Thr Glu Ala Arg Lys Val Phe Cys Glu Val Tyr Lys Glu Arg Leu Phe
    370                 375                 380

Gly Lys Lys Tyr Val Trp Phe Leu Ile Gly Trp Tyr Ala Asp Asn Trp
385                 390                 395                 400

Phe Lys Ile Tyr Asp Pro Ser Ile Asn Cys Thr Val Asp Glu Met Thr
                405                 410                 415

Glu Ala Val Glu Gly His Ile Thr Thr Glu Ile Val Met Leu Asn Pro
            420                 425                 430

Ala Asn Thr Arg Ser Ile Ser Asn Met Thr Ser Gln Glu Phe Val Glu
        435                 440                 445

Lys Leu Thr Lys Arg Leu Lys Arg His Pro Glu Glu Thr Gly Gly Phe
    450                 455                 460

Gln Glu Ala Pro Leu Ala Tyr Asp Ala Ile Trp Ala Leu Ala Leu Ala
465                 470                 475                 480

Leu Asn Lys Thr Ser Gly Gly Gly Arg Ser Gly Val Arg Leu Glu
                485                 490                 495

Asp Phe Asn Tyr Asn Asn Gln Thr Ile Thr Asp Gln Ile Tyr Arg Ala
                500                 505                 510

Met Asn Ser Ser Phe Glu Gly Val Ser Gly His Val Val Phe Asp
                515                 520                 525

Ala Ser Gly Ser Arg Met Ala Trp Thr Leu Ile Glu Gln Leu Gln Gly
    530                 535                 540

Gly Ser Tyr Lys Lys Ile Gly Tyr Tyr Asp Ser Thr Lys Asp Asp Leu
545                 550                 555                 560

Ser Trp Ser Lys Thr Asp Lys Trp Ile Gly Ser Pro Pro Ala Asp
                565                 570                 575

Gln Thr Leu Val Ile Lys Thr Phe Arg Phe Leu Ser Gln Lys Leu Phe
                580                 585                 590

Ile Ser Val Ser Val Leu Ser Ser Leu Gly Ile Val Leu Ala Val Val
        595                 600                 605

Cys Leu Ser Phe Asn Ile Tyr Asn Ser His Val Arg Tyr Ile Gln Asn
    610                 615                 620

Ser Gln Pro Asn Leu Asn Asn Leu Thr Ala Val Gly Cys Ser Leu Ala
625                 630                 635                 640

Leu Ala Ala Val Phe Pro Leu Gly Leu Asp Gly Tyr His Ile Gly Arg
                645                 650                 655

Asn Gln Phe Pro Phe Val Cys Gln Ala Arg Leu Trp Leu Leu Gly Leu
                660                 665                 670

Gly Phe Ser Leu Gly Tyr Gly Ser Met Phe Thr Lys Ile Trp Trp Val
        675                 680                 685

His Thr Val Phe Thr Lys Lys Glu Glu Lys Glu Trp Arg Lys Thr
    690                 695                 700

Leu Glu Pro Trp Lys Leu Tyr Ala Thr Val Gly Leu Leu Val Gly Met
705                 710                 715                 720

Asp Val Leu Thr Leu Ala Ile Trp Gln Ile Val Asp Pro Leu His Arg
                725                 730                 735

Thr Ile Glu Thr Phe Ala Lys Glu Glu Pro Lys Glu Asp Ile Asp Val
            740                 745                 750

Ser Ile Leu Pro Gln Leu Glu His Cys Ser Ser Arg Lys Met Asn Thr
        755                 760                 765

Trp Leu Gly Ile Phe Tyr Gly Tyr Lys Gly Leu Leu Leu Leu Gly
    770                 775                 780

Ile Phe Leu Ala Tyr Glu Thr Lys Ser Val Ser Thr Glu Lys Ile Asn
785                 790                 795                 800
```

```
Asp His Arg Ala Val Gly Met Ala Ile Tyr Asn Val Ala Val Leu Cys
                805                 810                 815

Leu Ile Thr Ala Pro Val Thr Met Ile Leu Ser Ser Gln Gln Asp Ala
            820                 825                 830

Ala Phe Ala Phe Ala Ser Leu Ala Ile Val Phe Ser Tyr Ile Thr
        835                 840                 845

Leu Val Val Leu Phe Val Pro Lys Met Arg Leu Ile Thr Arg Gly
    850                 855                 860

Glu Trp Gln Ser Glu Ala Gln Asp Thr Met Lys Thr Gly Ser Ser Thr
865                 870                 875                 880

Asn Asn Asn Glu Glu Glu Lys Ser Arg Leu Leu Glu Lys Glu Asn Arg
                885                 890                 895

Glu Leu Glu Lys Ile Ile Ala Glu Lys Glu Arg Val Ser Glu Leu
                900                 905                 910

Arg His Gln Leu Gln Ser Arg Gln Gln Leu Arg Ser Arg Arg His Pro
                915                 920                 925

Pro Thr Pro Pro Glu Pro Ser Gly Gly Leu Pro Arg Gly Pro Pro Glu
            930                 935                 940

Pro Pro Asp Arg Leu Ser Cys Asp Gly Ser Arg Val His Leu Leu Tyr
945                 950                 955                 960

Lys

<210> SEQ ID NO 17
<211> LENGTH: 941
<212> TYPE: PRT
<213> ORGANISM: Homo sapiens

<400> SEQUENCE: 17

Met Ala Ser Pro Arg Ser Ser Gly Gln Pro Gly Pro Pro Pro Pro Pro
1               5                   10                  15

Pro Pro Pro Pro Ala Arg Leu Leu Leu Leu Leu Leu Pro Leu Leu
            20                  25                  30

Leu Pro Leu Ala Pro Gly Ala Trp Gly Trp Ala Arg Gly Ala Pro Arg
                35                  40                  45

Pro Pro Pro Ser Ser Pro Pro Leu Ser Ile Met Gly Leu Met Pro Leu
50                  55                  60

Thr Lys Glu Val Ala Lys Gly Ser Ile Gly Arg Gly Val Leu Pro Ala
65                  70                  75                  80

Val Glu Leu Ala Ile Glu Gln Ile Arg Asn Glu Ser Leu Leu Arg Pro
                85                  90                  95

Tyr Phe Leu Asp Leu Arg Leu Tyr Asp Thr Glu Cys Asp Asn Ala Lys
                100                 105                 110

Gly Leu Lys Ala Phe Tyr Asp Ala Ile Lys Tyr Gly Pro Asn His Leu
            115                 120                 125

Met Val Phe Gly Gly Val Cys Pro Ser Val Thr Ser Ile Ile Ala Glu
        130                 135                 140

Ser Leu Gln Gly Trp Asn Leu Val Gln Leu Ser Phe Ala Ala Thr Thr
145                 150                 155                 160

Pro Val Leu Ala Asp Lys Lys Lys Tyr Pro Tyr Phe Phe Arg Thr Val
                165                 170                 175

Pro Ser Asp Asn Ala Val Asn Pro Ala Ile Leu Lys Leu Leu Lys His
                180                 185                 190

Tyr Gln Trp Lys Arg Val Gly Thr Leu Thr Gln Asp Val Gln Arg Phe
                195                 200                 205
```

-continued

```
Ser Glu Val Arg Asn Asp Leu Thr Gly Val Leu Tyr Gly Glu Asp Ile
    210                 215                 220

Glu Ile Ser Asp Thr Glu Ser Phe Ser Asn Asp Pro Cys Thr Ser Val
225                 230                 235                 240

Lys Lys Leu Lys Gly Asn Asp Val Arg Ile Ile Leu Gly Gln Phe Asp
                245                 250                 255

Gln Asn Met Ala Ala Lys Val Phe Cys Cys Ala Tyr Glu Glu Asn Met
            260                 265                 270

Tyr Gly Ser Lys Tyr Gln Trp Ile Ile Pro Gly Trp Tyr Glu Pro Ser
        275                 280                 285

Trp Trp Glu Gln Val His Thr Glu Ala Asn Ser Ser Arg Cys Leu Arg
    290                 295                 300

Lys Asn Leu Leu Ala Ala Met Glu Gly Tyr Ile Gly Val Asp Phe Glu
305                 310                 315                 320

Pro Leu Ser Ser Lys Gln Ile Lys Thr Ile Ser Gly Lys Thr Pro Gln
                325                 330                 335

Gln Tyr Glu Arg Glu Tyr Asn Asn Lys Arg Ser Gly Val Gly Pro Ser
            340                 345                 350

Lys Phe His Gly Tyr Ala Tyr Asp Gly Ile Trp Val Ile Ala Lys Thr
        355                 360                 365

Leu Gln Arg Ala Met Glu Thr Leu His Ala Ser Ser Arg His Gln Arg
    370                 375                 380

Ile Gln Asp Phe Asn Tyr Thr Asp His Thr Leu Gly Arg Ile Ile Leu
385                 390                 395                 400

Asn Ala Met Asn Glu Thr Asn Phe Phe Gly Val Thr Gly Gln Val Val
                405                 410                 415

Phe Arg Asn Gly Glu Arg Met Gly Thr Ile Lys Phe Thr Gln Phe Gln
            420                 425                 430

Asp Ser Arg Glu Val Lys Val Gly Glu Tyr Asn Ala Val Ala Asp Thr
        435                 440                 445

Leu Glu Ile Ile Asn Asp Thr Ile Arg Phe Gln Gly Ser Glu Pro Pro
    450                 455                 460

Lys Asp Lys Thr Ile Ile Leu Glu Gln Leu Arg Lys Ile Ser Leu Pro
465                 470                 475                 480

Leu Tyr Ser Ile Leu Ser Ala Leu Thr Ile Leu Gly Met Ile Met Ala
                485                 490                 495

Ser Ala Phe Leu Phe Asn Ile Lys Asn Arg Asn Gln Lys Leu Ile
            500                 505                 510

Lys Met Ser Ser Pro Tyr Met Asn Asn Leu Ile Ile Leu Gly Gly Met
        515                 520                 525

Leu Ser Tyr Ala Ser Ile Phe Leu Phe Gly Leu Asp Gly Ser Phe Val
    530                 535                 540

Ser Glu Lys Thr Phe Glu Thr Leu Cys Thr Val Arg Thr Trp Ile Leu
545                 550                 555                 560

Thr Val Gly Tyr Thr Thr Ala Phe Gly Ala Met Phe Ala Lys Thr Trp
                565                 570                 575

Arg Val His Ala Ile Phe Lys Asn Val Lys Met Lys Lys Lys Ile Ile
            580                 585                 590

Lys Asp Gln Lys Leu Leu Val Ile Val Gly Gly Met Leu Leu Ile Asp
        595                 600                 605

Leu Cys Ile Leu Ile Cys Trp Gln Ala Val Asp Pro Leu Arg Arg Thr
    610                 615                 620

Val Glu Lys Tyr Ser Met Glu Pro Asp Pro Ala Gly Arg Asp Ile Ser
625                 630                 635                 640
```

```
Ile Arg Pro Leu Leu Glu His Cys Glu Asn Thr His Met Thr Ile Trp
            645                 650                 655

Leu Gly Ile Val Tyr Ala Tyr Lys Gly Leu Leu Met Leu Phe Gly Cys
            660                 665                 670

Phe Leu Ala Trp Glu Thr Arg Asn Val Ser Ile Pro Ala Leu Asn Asp
            675                 680                 685

Ser Lys Tyr Ile Gly Met Ser Val Tyr Asn Val Gly Ile Met Cys Ile
            690                 695                 700

Ile Gly Ala Ala Val Ser Phe Leu Thr Arg Asp Gln Pro Asn Val Gln
705                 710                 715                 720

Phe Cys Ile Val Ala Leu Val Ile Ile Phe Cys Ser Thr Ile Thr Leu
            725                 730                 735

Cys Leu Val Phe Val Pro Lys Leu Ile Thr Leu Arg Thr Asn Pro Asp
            740                 745                 750

Ala Ala Thr Gln Asn Arg Arg Phe Gln Phe Thr Gln Asn Gln Lys Lys
            755                 760                 765

Glu Asp Ser Lys Thr Ser Thr Ser Val Thr Ser Val Asn Gln Ala Ser
            770                 775                 780

Thr Ser Arg Leu Glu Gly Leu Gln Ser Glu Asn His Arg Leu Arg Met
785                 790                 795                 800

Lys Ile Thr Glu Leu Asp Lys Asp Leu Glu Glu Val Thr Met Gln Leu
            805                 810                 815

Gln Asp Thr Pro Glu Lys Thr Thr Tyr Ile Lys Gln Asn His Tyr Gln
            820                 825                 830

Glu Leu Asn Asp Ile Leu Asn Leu Gly Asn Phe Thr Glu Ser Thr Asp
            835                 840                 845

Gly Gly Lys Ala Ile Leu Lys Asn His Leu Asp Gln Asn Pro Gln Leu
850                 855                 860

Gln Trp Asn Thr Thr Glu Pro Ser Arg Thr Cys Lys Asp Pro Ile Glu
865                 870                 875                 880

Asp Ile Asn Ser Pro Glu His Ile Gln Arg Arg Leu Ser Leu Gln Leu
            885                 890                 895

Pro Ile Leu His His Ala Tyr Leu Pro Ser Ile Gly Gly Val Asp Ala
            900                 905                 910

Ser Cys Val Ser Pro Cys Val Ser Pro Thr Ala Ser Pro Arg His Arg
            915                 920                 925

His Val Pro Pro Ser Phe Arg Val Met Val Ser Gly Leu
930                 935                 940

<210> SEQ ID NO 18
<211> LENGTH: 841
<212> TYPE: PRT
<213> ORGANISM: Homo sapiens

<400> SEQUENCE: 18

Met Leu Leu Cys Thr Ala Arg Leu Val Gly Leu Gln Leu Leu Ile Ser
1               5                   10                  15

Cys Cys Trp Ala Phe Ala Cys His Ser Thr Glu Ser Ser Pro Asp Phe
            20                  25                  30

Thr Leu Pro Gly Asp Tyr Leu Leu Ala Gly Leu Phe Pro Leu His Ser
            35                  40                  45

Gly Cys Leu Gln Val Arg His Arg Pro Glu Val Thr Leu Cys Asp Arg
        50                  55                  60

Ser Cys Ser Phe Asn Glu His Gly Tyr His Leu Phe Gln Ala Met Arg
65              70                  75                  80
```

-continued

```
Leu Gly Val Glu Glu Ile Asn Asn Ser Thr Ala Leu Leu Pro Asn Ile
                 85                  90                  95
Thr Leu Gly Tyr Gln Leu Tyr Asp Val Cys Ser Asp Ser Ala Asn Val
            100                 105                 110
Tyr Ala Thr Leu Arg Val Leu Ser Leu Pro Gly Gln His His Ile Glu
        115                 120                 125
Leu Gln Gly Asp Leu Leu His Tyr Ser Pro Thr Val Leu Ala Val Ile
    130                 135                 140
Gly Pro Asp Ser Thr Asn Arg Ala Ala Thr Thr Ala Ala Leu Leu Ser
145                 150                 155                 160
Pro Phe Leu Val Pro Met Ile Ser Tyr Ala Ala Ser Ser Glu Thr Leu
                165                 170                 175
Ser Val Lys Arg Gln Tyr Pro Ser Phe Leu Arg Thr Ile Pro Asn Asp
            180                 185                 190
Lys Tyr Gln Val Glu Thr Met Val Leu Leu Leu Gln Lys Phe Gly Trp
        195                 200                 205
Thr Trp Ile Ser Leu Val Gly Ser Ser Asp Asp Tyr Gly Gln Leu Gly
    210                 215                 220
Val Gln Ala Leu Glu Asn Gln Ala Thr Gly Gln Gly Ile Cys Ile Ala
225                 230                 235                 240
Phe Lys Asp Ile Met Pro Phe Ser Ala Gln Val Gly Asp Glu Arg Met
                245                 250                 255
Gln Cys Leu Met Arg His Leu Ala Gln Ala Gly Ala Thr Val Val Val
            260                 265                 270
Val Phe Ser Ser Arg Gln Leu Ala Arg Val Phe Phe Glu Ser Val Val
        275                 280                 285
Leu Thr Asn Leu Thr Gly Lys Val Trp Val Ala Ser Glu Ala Trp Ala
    290                 295                 300
Leu Ser Arg His Ile Thr Gly Val Pro Gly Ile Gln Arg Ile Gly Met
305                 310                 315                 320
Val Leu Gly Val Ala Ile Gln Lys Arg Ala Val Pro Gly Leu Lys Ala
                325                 330                 335
Phe Glu Glu Ala Tyr Ala Arg Ala Asp Lys Lys Ala Pro Arg Pro Cys
            340                 345                 350
His Lys Gly Ser Trp Cys Ser Ser Asn Gln Leu Cys Arg Glu Cys Gln
        355                 360                 365
Ala Phe Met Ala His Thr Met Pro Lys Leu Lys Ala Phe Ser Met Ser
    370                 375                 380
Ser Ala Tyr Asn Ala Tyr Arg Ala Val Tyr Ala Val Ala His Gly Leu
385                 390                 395                 400
His Gln Leu Leu Gly Cys Ala Ser Gly Ala Cys Ser Arg Gly Arg Val
                405                 410                 415
Tyr Pro Trp Gln Leu Leu Glu Gln Ile His Lys Val His Phe Leu Leu
            420                 425                 430
His Lys Asp Thr Val Ala Phe Asn Asp Asn Arg Asp Pro Leu Ser Ser
        435                 440                 445
Tyr Asn Ile Ile Ala Trp Asp Trp Asn Gly Pro Lys Trp Thr Phe Thr
    450                 455                 460
Val Leu Gly Ser Ser Thr Trp Ser Pro Val Gln Leu Asn Ile Asn Glu
465                 470                 475                 480
Thr Lys Ile Gln Trp His Gly Lys Asp Asn Gln Val Pro Lys Ser Val
                485                 490                 495
Cys Ser Ser Asp Cys Leu Glu Gly His Gln Arg Val Val Thr Gly Phe
```

```
                500             505             510
His His Cys Cys Phe Glu Cys Val Pro Cys Gly Ala Gly Thr Phe Leu
            515                 520             525

Asn Lys Ser Asp Leu Tyr Arg Cys Gln Pro Cys Gly Lys Glu Glu Trp
        530                 535             540

Ala Pro Glu Gly Ser Gln Thr Cys Phe Pro Arg Thr Val Val Phe Leu
545                 550             555                 560

Ala Leu Arg Glu His Thr Ser Trp Val Leu Leu Ala Ala Asn Thr Leu
                565             570              575

Leu Leu Leu Leu Leu Leu Gly Thr Ala Gly Leu Phe Ala Trp His Leu
            580             585                 590

Asp Thr Pro Val Val Arg Ser Ala Gly Gly Arg Leu Cys Phe Leu Met
            595             600             605

Leu Gly Ser Leu Ala Ala Gly Ser Gly Ser Leu Tyr Gly Phe Phe Gly
        610             615             620

Glu Pro Thr Arg Pro Ala Cys Leu Leu Arg Gln Ala Leu Phe Ala Leu
625             630             635                 640

Gly Phe Thr Ile Phe Leu Ser Cys Leu Thr Val Arg Ser Phe Gln Leu
                645             650             655

Ile Ile Ile Phe Lys Phe Ser Thr Lys Val Pro Thr Phe Tyr His Ala
                660             665             670

Trp Val Gln Asn His Gly Ala Gly Leu Phe Val Met Ile Ser Ser Ala
            675             680             685

Ala Gln Leu Leu Ile Cys Leu Thr Trp Leu Val Val Trp Thr Pro Leu
        690             695             700

Pro Ala Arg Glu Tyr Gln Arg Phe Pro His Leu Val Met Leu Glu Cys
705             710             715             720

Thr Glu Thr Asn Ser Leu Gly Phe Ile Leu Ala Phe Leu Tyr Asn Gly
                725             730             735

Leu Leu Ser Ile Ser Ala Phe Ala Cys Ser Tyr Leu Gly Lys Asp Leu
                740             745             750

Pro Glu Asn Tyr Asn Glu Ala Lys Cys Val Thr Phe Ser Leu Leu Phe
            755             760             765

Asn Phe Val Ser Trp Ile Ala Phe Phe Thr Thr Ala Ser Val Tyr Asp
        770             775             780

Gly Lys Tyr Leu Pro Ala Ala Asn Met Met Ala Gly Leu Ser Ser Leu
785             790             795             800

Ser Ser Gly Phe Gly Gly Tyr Phe Leu Pro Lys Cys Tyr Val Ile Leu
                805             810             815

Cys Arg Pro Asp Leu Asn Ser Thr Glu His Phe Gln Ala Ser Ile Gln
            820             825             830

Asp Tyr Thr Arg Arg Cys Gly Ser Thr
            835             840

<210> SEQ ID NO 19
<211> LENGTH: 839
<212> TYPE: PRT
<213> ORGANISM: Homo sapiens

<400> SEQUENCE: 19

Met Gly Pro Arg Ala Lys Thr Ile Ser Ser Leu Phe Phe Leu Leu Trp
1               5                   10                  15

Val Leu Ala Glu Pro Ala Glu Asn Ser Asp Phe Tyr Leu Pro Gly Asp
            20                  25                  30

Tyr Leu Leu Gly Gly Leu Phe Ser Leu His Ala Asn Met Lys Gly Ile
```

```
                35                  40                  45
Val His Leu Asn Phe Leu Gln Val Pro Met Cys Lys Glu Tyr Glu Val
 50                  55                  60
Lys Val Ile Gly Tyr Asn Leu Met Gln Ala Met Arg Phe Ala Val Glu
 65                  70                  75                  80
Glu Ile Asn Asn Asp Ser Ser Leu Leu Pro Gly Val Leu Leu Gly Tyr
                 85                  90                  95
Glu Ile Val Asp Val Cys Tyr Ile Ser Asn Asn Val Gln Pro Val Leu
                100                 105                 110
Tyr Phe Leu Ala His Glu Asp Asn Leu Leu Pro Ile Gln Glu Asp Tyr
                115                 120                 125
Ser Asn Tyr Ile Ser Arg Val Ala Val Ile Gly Pro Asp Asn Ser
130                 135                 140
Glu Ser Val Met Thr Val Ala Asn Phe Leu Ser Leu Phe Leu Leu Pro
145                 150                 155                 160
Gln Ile Thr Tyr Ser Ala Ile Ser Asp Glu Leu Arg Asp Lys Val Arg
                165                 170                 175
Phe Pro Ala Leu Leu Arg Thr Thr Pro Ser Ala Asp His His Ile Glu
                180                 185                 190
Ala Met Val Gln Leu Met Leu His Phe Arg Trp Asn Trp Ile Ile Val
                195                 200                 205
Leu Val Ser Ser Asp Thr Tyr Gly Arg Asp Asn Gly Gln Leu Leu Gly
                210                 215                 220
Glu Arg Val Ala Arg Arg Asp Ile Cys Ile Ala Phe Gln Glu Thr Leu
225                 230                 235                 240
Pro Thr Leu Gln Pro Asn Gln Asn Met Thr Ser Glu Glu Arg Gln Arg
                245                 250                 255
Leu Val Thr Ile Val Asp Lys Leu Gln Gln Ser Thr Ala Arg Val Val
                260                 265                 270
Val Val Phe Ser Pro Asp Leu Thr Leu Tyr His Phe Phe Asn Glu Val
                275                 280                 285
Leu Arg Gln Asn Phe Thr Gly Ala Val Trp Ile Ala Ser Glu Ser Trp
                290                 295                 300
Ala Ile Asp Pro Val Leu His Asn Leu Thr Glu Leu Arg His Leu Gly
305                 310                 315                 320
Thr Phe Leu Gly Ile Thr Ile Gln Ser Val Pro Ile Pro Gly Phe Ser
                325                 330                 335
Glu Phe Arg Glu Trp Gly Pro Gln Ala Gly Pro Pro Pro Leu Ser Arg
                340                 345                 350
Thr Ser Gln Ser Tyr Thr Cys Asn Gln Glu Cys Asp Asn Cys Leu Asn
                355                 360                 365
Ala Thr Leu Ser Phe Asn Thr Ile Leu Arg Leu Ser Gly Glu Arg Val
                370                 375                 380
Val Tyr Ser Val Tyr Ser Ala Val Tyr Ala Val Ala His Ala Leu His
385                 390                 395                 400
Ser Leu Leu Gly Cys Asp Lys Ser Thr Cys Thr Lys Arg Val Val Tyr
                405                 410                 415
Pro Trp Gln Leu Leu Glu Glu Ile Trp Lys Val Asn Phe Thr Leu Leu
                420                 425                 430
Asp His Gln Ile Phe Phe Asp Pro Gln Gly Asp Val Ala Leu His Leu
                435                 440                 445
Glu Ile Val Gln Trp Gln Trp Asp Arg Ser Gln Asn Pro Phe Gln Ser
                450                 455                 460
```

Val Ala Ser Tyr Tyr Pro Leu Gln Arg Gln Leu Lys Asn Ile Gln Asp
465                 470                 475                 480

Ile Ser Trp His Thr Ile Asn Asn Thr Ile Pro Met Ser Met Cys Ser
            485                 490                 495

Lys Arg Cys Gln Ser Gly Gln Lys Lys Pro Val Gly Ile His Val
        500                 505                 510

Cys Cys Phe Glu Cys Ile Asp Cys Leu Pro Gly Thr Phe Leu Asn His
        515                 520                 525

Thr Glu Asp Glu Tyr Glu Cys Gln Ala Cys Pro Asn Asn Glu Trp Ser
        530                 535                 540

Tyr Gln Ser Glu Thr Ser Cys Phe Lys Arg Gln Leu Val Phe Leu Glu
545                 550                 555                 560

Trp His Glu Ala Pro Thr Ile Ala Val Ala Leu Leu Ala Ala Leu Gly
                565                 570                 575

Phe Leu Ser Thr Leu Ala Ile Leu Val Ile Phe Trp Arg His Phe Gln
                580                 585                 590

Thr Pro Ile Val Arg Ser Ala Gly Gly Pro Met Cys Phe Leu Met Leu
            595                 600                 605

Thr Leu Leu Leu Val Ala Tyr Met Val Val Pro Val Tyr Val Gly Pro
610                 615                 620

Pro Lys Val Ser Thr Cys Leu Cys Arg Gln Ala Leu Phe Pro Leu Cys
625                 630                 635                 640

Phe Thr Ile Cys Ile Ser Cys Ile Ala Val Arg Ser Phe Gln Ile Val
                645                 650                 655

Cys Ala Phe Lys Met Ala Ser Arg Phe Pro Arg Ala Tyr Ser Tyr Trp
            660                 665                 670

Val Arg Tyr Gln Gly Pro Tyr Val Ser Met Ala Phe Ile Thr Val Leu
            675                 680                 685

Lys Met Val Ile Val Val Ile Gly Met Leu Ala Thr Gly Leu Ser Pro
690                 695                 700

Thr Thr Arg Thr Asp Pro Asp Pro Lys Ile Thr Ile Val Ser Cys
705                 710                 715                 720

Asn Pro Asn Tyr Arg Asn Ser Leu Leu Phe Asn Thr Ser Leu Asp Leu
            725                 730                 735

Leu Leu Ser Val Val Gly Phe Ser Phe Ala Tyr Met Gly Lys Glu Leu
            740                 745                 750

Pro Thr Asn Tyr Asn Glu Ala Lys Phe Ile Thr Leu Ser Met Thr Phe
            755                 760                 765

Tyr Phe Thr Ser Ser Val Ser Leu Cys Thr Phe Met Ser Ala Tyr Ser
            770                 775                 780

Gly Val Leu Val Thr Ile Val Asp Leu Leu Val Thr Val Leu Asn Leu
785                 790                 795                 800

Leu Ala Ile Ser Leu Gly Tyr Phe Gly Pro Lys Cys Tyr Met Ile Leu
                805                 810                 815

Phe Tyr Pro Glu Arg Asn Thr Pro Ala Tyr Phe Asn Ser Met Ile Gln
                820                 825                 830

Gly Tyr Thr Met Arg Arg Asp
            835

<210> SEQ ID NO 20
<211> LENGTH: 852
<212> TYPE: PRT
<213> ORGANISM: Homo sapiens

<400> SEQUENCE: 20

-continued

```
Met Leu Gly Pro Ala Val Leu Gly Leu Ser Leu Trp Ala Leu Leu His
1               5                   10                  15

Pro Gly Thr Gly Ala Pro Leu Cys Leu Ser Gln Gln Leu Arg Met Lys
            20                  25                  30

Gly Asp Tyr Val Leu Gly Gly Leu Phe Pro Leu Gly Glu Ala Glu Glu
            35                  40                  45

Ala Gly Leu Arg Ser Arg Thr Arg Pro Ser Ser Pro Val Cys Thr Arg
    50                  55                  60

Phe Ser Ser Asn Gly Leu Leu Trp Ala Leu Ala Met Lys Met Ala Val
65                  70                  75                  80

Glu Glu Ile Asn Asn Lys Ser Asp Leu Leu Pro Gly Leu Arg Leu Gly
                85                  90                  95

Tyr Asp Leu Phe Asp Thr Cys Ser Glu Pro Val Val Ala Met Lys Pro
            100                 105                 110

Ser Leu Met Phe Leu Ala Lys Ala Gly Ser Arg Asp Ile Ala Ala Tyr
            115                 120                 125

Cys Asn Tyr Thr Gln Tyr Gln Pro Arg Val Leu Ala Val Ile Gly Pro
    130                 135                 140

His Ser Ser Glu Leu Ala Met Val Thr Gly Lys Phe Phe Ser Phe Phe
145                 150                 155                 160

Leu Met Pro Gln Val Ser Tyr Gly Ala Ser Met Glu Leu Leu Ser Ala
                165                 170                 175

Arg Glu Thr Phe Pro Ser Phe Phe Arg Thr Val Pro Ser Asp Arg Val
            180                 185                 190

Gln Leu Thr Ala Ala Ala Glu Leu Leu Gln Glu Phe Gly Trp Asn Trp
    195                 200                 205

Val Ala Ala Leu Gly Ser Asp Asp Glu Tyr Gly Arg Gln Gly Leu Ser
210                 215                 220

Ile Phe Ser Ala Leu Ala Ala Ala Arg Gly Ile Cys Ile Ala His Glu
225                 230                 235                 240

Gly Leu Val Pro Leu Pro Arg Ala Asp Asp Ser Arg Leu Gly Lys Val
                245                 250                 255

Gln Asp Val Leu His Gln Val Asn Gln Ser Ser Val Gln Val Val Leu
            260                 265                 270

Leu Phe Ala Ser Val His Ala Ala His Ala Leu Phe Asn Tyr Ser Ile
    275                 280                 285

Ser Ser Arg Leu Ser Pro Lys Val Trp Val Ala Ser Glu Ala Trp Leu
290                 295                 300

Thr Ser Asp Leu Val Met Gly Leu Pro Gly Met Ala Gln Met Gly Thr
305                 310                 315                 320

Val Leu Gly Phe Leu Gln Arg Gly Ala Gln Leu His Glu Phe Pro Gln
                325                 330                 335

Tyr Val Lys Thr His Leu Ala Leu Ala Thr Asp Pro Ala Phe Cys Ser
            340                 345                 350

Ala Leu Gly Glu Arg Glu Gln Gly Leu Glu Glu Asp Val Val Gly Gln
    355                 360                 365

Arg Cys Pro Gln Cys Asp Cys Ile Thr Leu Gln Asn Val Ser Ala Gly
370                 375                 380

Leu Asn His His Gln Thr Phe Ser Val Tyr Ala Ala Val Tyr Ser Val
385                 390                 395                 400

Ala Gln Ala Leu His Asn Thr Leu Gln Cys Asn Ala Ser Gly Cys Pro
                405                 410                 415

Ala Gln Asp Pro Val Lys Pro Trp Gln Leu Leu Glu Asn Met Tyr Asn
            420                 425                 430
```

```
Leu Thr Phe His Val Gly Gly Leu Pro Leu Arg Phe Asp Ser Ser Gly
        435                 440                 445
Asn Val Asp Met Glu Tyr Asp Leu Lys Leu Trp Val Trp Gln Gly Ser
    450                 455                 460
Val Pro Arg Leu His Asp Val Gly Arg Phe Asn Gly Ser Leu Arg Thr
465                 470                 475                 480
Glu Arg Leu Lys Ile Arg Trp His Thr Ser Asp Asn Gln Lys Pro Val
                485                 490                 495
Ser Arg Cys Ser Arg Gln Cys Gln Glu Gly Gln Val Arg Arg Val Lys
            500                 505                 510
Gly Phe His Ser Cys Cys Tyr Asp Cys Val Asp Cys Glu Ala Gly Ser
        515                 520                 525
Tyr Arg Gln Asn Pro Asp Asp Ile Ala Cys Thr Phe Cys Gly Gln Asp
    530                 535                 540
Glu Trp Ser Pro Glu Arg Ser Thr Arg Cys Phe Arg Arg Ser Arg
545                 550                 555                 560
Phe Leu Ala Trp Gly Glu Pro Ala Val Leu Leu Leu Leu Leu Leu Leu
                565                 570                 575
Ser Leu Ala Leu Gly Leu Val Leu Ala Ala Leu Gly Leu Phe Val His
            580                 585                 590
His Arg Asp Ser Pro Leu Val Gln Ala Ser Gly Gly Pro Leu Ala Cys
        595                 600                 605
Phe Gly Leu Val Cys Leu Gly Leu Val Cys Leu Ser Val Leu Leu Phe
    610                 615                 620
Pro Gly Gln Pro Ser Pro Ala Arg Cys Leu Ala Gln Gln Pro Leu Ser
625                 630                 635                 640
His Leu Pro Leu Thr Gly Cys Leu Ser Thr Leu Phe Leu Gln Ala Ala
                645                 650                 655
Glu Ile Phe Val Glu Ser Glu Leu Pro Leu Ser Trp Ala Asp Arg Leu
            660                 665                 670
Ser Gly Cys Leu Arg Gly Pro Trp Ala Trp Leu Val Val Leu Leu Ala
        675                 680                 685
Met Leu Val Glu Val Ala Leu Cys Thr Trp Tyr Leu Val Ala Phe Pro
    690                 695                 700
Pro Glu Val Val Thr Asp Trp His Met Leu Pro Thr Glu Ala Leu Val
705                 710                 715                 720
His Cys Arg Thr Arg Ser Trp Val Ser Phe Gly Leu Ala His Ala Thr
                725                 730                 735
Asn Ala Thr Leu Ala Phe Leu Cys Phe Leu Gly Thr Phe Leu Val Arg
            740                 745                 750
Ser Gln Pro Gly Cys Tyr Asn Arg Ala Arg Gly Leu Thr Phe Ala Met
        755                 760                 765
Leu Ala Tyr Phe Ile Thr Trp Val Ser Phe Val Pro Leu Leu Ala Asn
    770                 775                 780
Val Gln Val Val Leu Arg Pro Ala Val Gln Met Gly Ala Leu Leu Leu
785                 790                 795                 800
Cys Val Leu Gly Ile Leu Ala Ala Phe His Leu Pro Arg Cys Tyr Leu
                805                 810                 815
Leu Met Arg Gln Pro Gly Leu Asn Thr Pro Glu Phe Phe Leu Gly Gly
            820                 825                 830
Gly Pro Gly Asp Ala Gln Gly Gln Asn Asp Gly Asn Thr Gly Asn Gln
        835                 840                 845
Gly Lys His Glu
```

<210> SEQ ID NO 21
<211> LENGTH: 926
<212> TYPE: PRT
<213> ORGANISM: Homo sapiens

<400> SEQUENCE: 21

```
Met Ala Phe Leu Ile Ile Leu Ile Thr Cys Phe Val Ile Ile Leu Ala
1               5                   10                  15

Thr Ser Gln Pro Cys Gln Thr Pro Asp Asp Phe Val Ala Ala Thr Ser
            20                  25                  30

Pro Gly His Ile Ile Ile Gly Gly Leu Phe Ala Ile His Glu Lys Met
        35                  40                  45

Leu Ser Ser Glu Asp Ser Pro Arg Arg Pro Gln Ile Gln Glu Cys Val
    50                  55                  60

Gly Phe Glu Ile Ser Val Phe Leu Gln Thr Leu Ala Met Ile His Ser
65                  70                  75                  80

Ile Glu Met Ile Asn Asn Ser Thr Leu Leu Pro Gly Val Lys Leu Gly
                85                  90                  95

Tyr Glu Ile Tyr Asp Thr Cys Thr Glu Val Thr Val Ala Met Ala Ala
            100                 105                 110

Thr Leu Arg Phe Leu Ser Lys Phe Asn Cys Ser Arg Glu Thr Val Glu
        115                 120                 125

Phe Lys Cys Asp Tyr Ser Ser Tyr Met Pro Arg Val Lys Ala Val Ile
    130                 135                 140

Gly Ser Gly Tyr Ser Glu Ile Thr Met Ala Val Ser Arg Met Leu Asn
145                 150                 155                 160

Leu Gln Leu Met Pro Gln Val Gly Tyr Glu Ser Thr Ala Glu Ile Leu
                165                 170                 175

Ser Asp Lys Ile Arg Phe Pro Ser Phe Leu Arg Thr Val Pro Ser Asp
            180                 185                 190

Phe His Gln Ile Lys Ala Met Ala His Leu Ile Gln Lys Ser Gly Trp
        195                 200                 205

Asn Trp Ile Gly Ile Ile Thr Thr Asp Asp Asp Tyr Gly Arg Leu Ala
    210                 215                 220

Leu Asn Thr Phe Ile Ile Gln Ala Glu Ala Asn Asn Val Cys Ile Ala
225                 230                 235                 240

Phe Lys Glu Val Leu Pro Ala Phe Leu Ser Asp Asn Thr Ile Glu Val
                245                 250                 255

Arg Ile Asn Arg Thr Leu Lys Lys Ile Ile Leu Glu Ala Gln Val Asn
            260                 265                 270

Val Ile Val Val Phe Leu Arg Gln Phe His Val Phe Asp Leu Phe Asn
        275                 280                 285

Lys Ala Ile Glu Met Asn Ile Asn Lys Met Trp Ile Ala Ser Asp Asn
    290                 295                 300

Trp Ser Thr Ala Thr Lys Ile Thr Thr Ile Pro Asn Val Lys Lys Ile
305                 310                 315                 320

Gly Lys Val Val Gly Phe Ala Phe Arg Arg Gly Asn Ile Ser Ser Phe
                325                 330                 335

His Ser Phe Leu Gln Asn Leu His Leu Leu Pro Ser Asp Ser His Lys
            340                 345                 350

Leu Leu His Glu Tyr Ala Met His Leu Ser Ala Cys Ala Tyr Val Lys
        355                 360                 365

Asp Thr Asp Leu Ser Gln Cys Ile Phe Asn His Ser Gln Arg Thr Leu
```

-continued

```
              370                 375                 380
Ala Tyr Lys Ala Asn Lys Ala Ile Glu Arg Asn Phe Val Met Arg Asn
385                 390                 395                 400

Asp Phe Leu Trp Asp Tyr Ala Glu Pro Gly Leu Ile His Ser Ile Gln
                405                 410                 415

Leu Ala Val Phe Ala Leu Gly Tyr Ala Ile Arg Asp Leu Cys Gln Ala
                420                 425                 430

Arg Asp Cys Gln Asn Pro Asn Ala Phe Gln Pro Trp Glu Leu Leu Gly
                435                 440                 445

Val Leu Lys Asn Val Thr Phe Thr Asp Gly Trp Asn Ser Phe His Phe
450                 455                 460

Asp Ala His Gly Asp Leu Asn Thr Gly Tyr Asp Val Val Leu Trp Lys
465                 470                 475                 480

Glu Ile Asn Gly His Met Thr Val Thr Lys Met Ala Glu Tyr Asp Leu
                485                 490                 495

Gln Asn Asp Val Phe Ile Ile Pro Asp Gln Glu Thr Lys Asn Glu Phe
                500                 505                 510

Arg Asn Leu Lys Gln Ile Gln Ser Lys Cys Ser Lys Glu Cys Ser Pro
                515                 520                 525

Gly Gln Met Lys Lys Thr Thr Arg Ser Gln His Ile Cys Cys Tyr Glu
                530                 535                 540

Cys Gln Asn Cys Pro Glu Asn His Tyr Thr Asn Gln Thr Asp Met Pro
545                 550                 555                 560

His Cys Leu Leu Cys Asn Asn Lys Thr His Trp Ala Pro Val Arg Ser
                565                 570                 575

Thr Met Cys Phe Glu Lys Glu Val Glu Tyr Leu Asn Trp Asn Asp Ser
                580                 585                 590

Leu Ala Ile Leu Leu Leu Ile Leu Ser Leu Leu Gly Ile Ile Phe Val
                595                 600                 605

Leu Val Val Gly Ile Ile Phe Thr Arg Asn Leu Asn Thr Pro Val Val
                610                 615                 620

Lys Ser Ser Gly Gly Leu Arg Val Cys Tyr Val Ile Leu Leu Cys His
625                 630                 635                 640

Phe Leu Asn Phe Ala Ser Thr Ser Phe Phe Ile Gly Glu Pro Gln Asp
                645                 650                 655

Phe Thr Cys Lys Thr Arg Gln Thr Met Phe Gly Val Ser Phe Thr Leu
                660                 665                 670

Cys Ile Ser Cys Ile Leu Thr Lys Ser Leu Lys Ile Leu Leu Ala Phe
                675                 680                 685

Ser Phe Asp Pro Lys Leu Gln Lys Phe Leu Lys Cys Leu Tyr Arg Pro
690                 695                 700

Ile Leu Ile Ile Phe Thr Cys Thr Gly Ile Gln Val Val Ile Cys Thr
705                 710                 715                 720

Leu Trp Leu Ile Phe Ala Ala Pro Thr Val Glu Val Asn Val Ser Leu
                725                 730                 735

Pro Arg Val Ile Ile Leu Glu Cys Glu Glu Gly Ser Ile Leu Ala Phe
                740                 745                 750

Gly Thr Met Leu Gly Tyr Ile Ala Ile Leu Ala Phe Ile Cys Phe Ile
                755                 760                 765

Phe Ala Phe Lys Gly Lys Tyr Glu Asn Tyr Asn Glu Ala Lys Phe Ile
                770                 775                 780

Thr Phe Gly Met Leu Ile Tyr Phe Ile Ala Trp Ile Thr Phe Ile Pro
785                 790                 795                 800
```

```
Ile Tyr Ala Thr Thr Phe Gly Lys Tyr Val Pro Ala Val Glu Ile Ile
                805                 810                 815

Val Ile Leu Ile Ser Asn Tyr Gly Ile Leu Tyr Cys Thr Phe Ile Pro
            820                 825                 830

Lys Cys Tyr Val Ile Ile Cys Lys Gln Glu Ile Asn Thr Lys Ser Ala
        835                 840                 845

Phe Leu Lys Met Ile Tyr Ser Tyr Ser Ser His Ser Val Ser Ser Ile
    850                 855                 860

Ala Leu Ser Pro Ala Ser Leu Asp Ser Met Ser Gly Asn Val Thr Met
865                 870                 875                 880

Thr Asn Pro Ser Ser Ser Gly Lys Ser Ala Thr Trp Gln Lys Ser Lys
                885                 890                 895

Asp Leu Gln Ala Gln Ala Phe Ala His Ile Cys Arg Glu Asn Ala Thr
            900                 905                 910

Ser Val Ser Lys Thr Leu Pro Arg Lys Arg Met Ser Ser Ile
        915                 920                 925

<210> SEQ ID NO 22
<211> LENGTH: 7
<212> TYPE: PRT
<213> ORGANISM: Artificial Sequence
<220> FEATURE:
<223> OTHER INFORMATION: Synthetic amino acid sequence

<400> SEQUENCE: 22

Asp Tyr Lys Asp Asp Asp Ala
1               5
```

GPCR COMPRISING AN IC2 INSERTION

CROSS-REFERENCING

This application claims the benefit of U.S. provisional patent application Ser. No. 61/378,332, filed on Aug. 30, 2010, which application is incorporated herein in its entirety.

GOVERNMENT RIGHTS

This work was supported in part by Small Business Innovation Research grant number R43MH088091-01. The federal government has certain rights in this invention.

BACKGROUND

G-protein-coupled receptors (GPCRs) are a large family of proteins that are involved in a wide range of functions (including various autocrine, paracrine and endocrine processes). GPCRs show considerable diversity at the sequence level and can be separated into distinct families on the basis of their sequence.

The family C GPCR receptors (which are also known as family 3 GPCRs) are generally composed of four elements: an N-terminal signal sequence, a large hydrophilic extracellular agonist-binding region containing several conserved cysteine residues which may be involved in disulphide bonds, a shorter region containing seven transmembrane domains, and a C-terminal cytoplasmic domain of variable length (see, e.g., Bräuner-Osborne, Curr. Drug Targets 2007 8: 169-84). Family C GPCR members include the metabotropic glutamate receptors, the extracellular calcium-sensing receptors, the gamma-amino-butyric acid (GABA) type B receptors, and the vomeronasal type-2 receptors, for example (see, e.g., Tanabe Neuron 1992 8: 169-79; Brown, Nature 1993 366: 575-80; Sullivan, J. Pharmacol. Exp. Ther. 2000 293: 460-7; and Ryba, Neuron 1997 19: 371-9).

As family C GPCRs are involved in many important physiological processes, they are promising targets for drug development.

SUMMARY OF THE INVENTION

A fusion protein is provided. In certain embodiments, the fusion protein comprises: a) a first portion of a family C G-protein coupled receptor (GPCR), where the first portion comprises the TM1, TM2 and TM3 regions of the GPCR; b) a stable, folded protein insertion, e.g., the amino acid sequence of lysozyme; and c) a second portion of the GPCR, where the second portion comprises the TM4, TM5, TM6 and TM7 regions of the GPCR. The polypeptide may be employed in crystallization methods, for example.

In certain embodiments, the stable, folded protein insertion is a polypeptide than can fold autonomously in a variety of cellular expression hosts, and is resistant to chemical and thermal denaturation. In particular embodiments, the stable folded protein insertion may be a protein that is known to be highly crystallizable, in a variety of space groups and crystal packing arrangements. In certain cases, the stable, folded protein insertion may also shield the fusion protein from proteolysis between the TM3 and TM4 domains, and may itself be protease resistant. Lysozyme is one such polypeptide, however many others are known.

Also provided is a nucleic acid encoding the above described fusion protein, and a cell comprising the same. The fusion protein may be disposed on the plasma membrane of the cell.

Also provided are crystals comprising the above described fusion protein, folded into an active form.

The above-described cell may be employed in a method comprising: culturing the cell to produce the fusion protein; and isolating the fusion protein from the cell. The method may further comprise crystallizing the fusion protein to make crystals which, in certain embodiments, may involve combining the fusion protein with lipid prior to crystallization. In certain embodiments, the fusion protein is crystallized using a bicelle crystallization method or a lipidic cubic phase crystallization method. The method may further comprise obtaining atomic coordinates of the fusion protein from the crystal.

Also provided is a method of determining a crystal structure. This method may comprise receiving an above described fusion protein, crystallizing the fusion protein to produce a crystal; and obtaining atomic coordinates of the fusion protein from the crystals. In other embodiments, the method may comprise forwarding a fusion protein to a remote location where the protein may be crystallized and analyzed, and receiving the atomic coordinates of the fusion protein.

In particular embodiments, a composition comprising a fusion protein in crystalline form is provided in which the fusion protein comprises, from N-terminus to C-terminus: a) a first portion of a family C G-protein coupled receptor (GPCR), wherein the first portion comprises TM1, TM2, and TM3 regions of the GPCR; b) a domain comprising the amino acid sequence of a lysozyme; and c) a second portion of the GPCR, wherein the second portion comprises TM4, TM5, TM6 and TM7 regions of the GPCR.

In particular embodiments, the first and second portions of the GPCR comprise the amino acid sequence of a naturally occurring GPCR.

In other embodiments, the first and second portions of the GPCR comprise the amino acid sequence of a non-naturally occurring GPCR.

In some embodiments, the first portion or the second portion of the GPCR comprises an affinity tag.

The domain, in certain cases, may comprise an amino acid sequence having at least 80% identity to the amino acid sequence of a wild-type lysozyme. For example, in certain cases, the domain may comprise an amino acid sequence that is at least 95% identical to the amino acid sequence of T4 lysozyme.

In particular embodiments, the GPCR may selected from the group consisting of: calcium-sensing receptor (CASR), GPRC6A (GPRC6A), GABAB receptor 1 (GABBR1); GABAB receptor 2 (GABBR2), GPR156 (GPR156), mGluR1 (GRM1), mGluR2 (GRM2), mGluR3 (GRM3), mGluR4 (GRM4), mGluR5 (GRM5), mGluR6 (GRM6), mGluR7 (GRM7) mGluR8 (GRM8), RAIG1 (GPRC5A), RAIG2 (GPRC5B), RAIG3 (GPRC5C), RAIG4 (GPRC5D), taste receptor, type 1, member 1 (TAS1R1), taste receptor, type 1, member 2 (TAS1R2), taste receptor, type 1, member 3 (TAS1R3), GPR158 (GPR158), GPR179 (GPR179); bride of sevenless protein and vomeronasal receptor, type 2.

In some embodiments, the fusion protein is bound to a ligand for the GPCR.

In particular embodiments, the domain of b) spaces the C-terminal end of the TM3 region and the N-terminal end of the TM4 region of the GPCR such that the closest alpha carbon atoms at the C-terminal end and the N-terminal end are spaced by a distance in the range of from 6 Å to 16 Å.

Also provided is a composition comprising a polypeptide in crystalline form, wherein the polypeptide comprises, from N-terminus to C-terminus: a) a first portion of a family C G-protein coupled receptor (GPCR), wherein the first portion comprises the amino acid sequence that is N-terminal to the IC2 loop of the GPCR; b) a domain comprising the amino acid sequence of a lysozyme; and c) a second portion of the GPCR, wherein the second portion comprises the amino acid sequence that is C-terminal to the IC2 loop of the GPCR.

Also provided is a composition comprising a polypeptide in crystalline form, wherein the polypeptide comprises: a G-protein coupled receptor (GPCR) comprising an IC2 loop comprising the amino acid sequence of a lysozyme.

BRIEF DESCRIPTION OF THE FIGURES

FIG. 3 shows the amino acid and nucleotide sequences of an exemplary lysozyme fusion protein.

FIGS. 4A-4G show exemplary the amino acid sequences of several representative family C GPCRs, and an insertion point for a stable, folded protein insertion in each of the GPCRs. The TM3 and TM4 regions of each of the GPCRs is bolded and underlined in these figures.

FIG. 5 shows the amino acid sequences of exemplary stable, folder protein insertions that may be employed in a subject fusion protein.

DEFINITIONS

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with general dictionaries of many of the terms used in this disclosure. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

Figure 1:
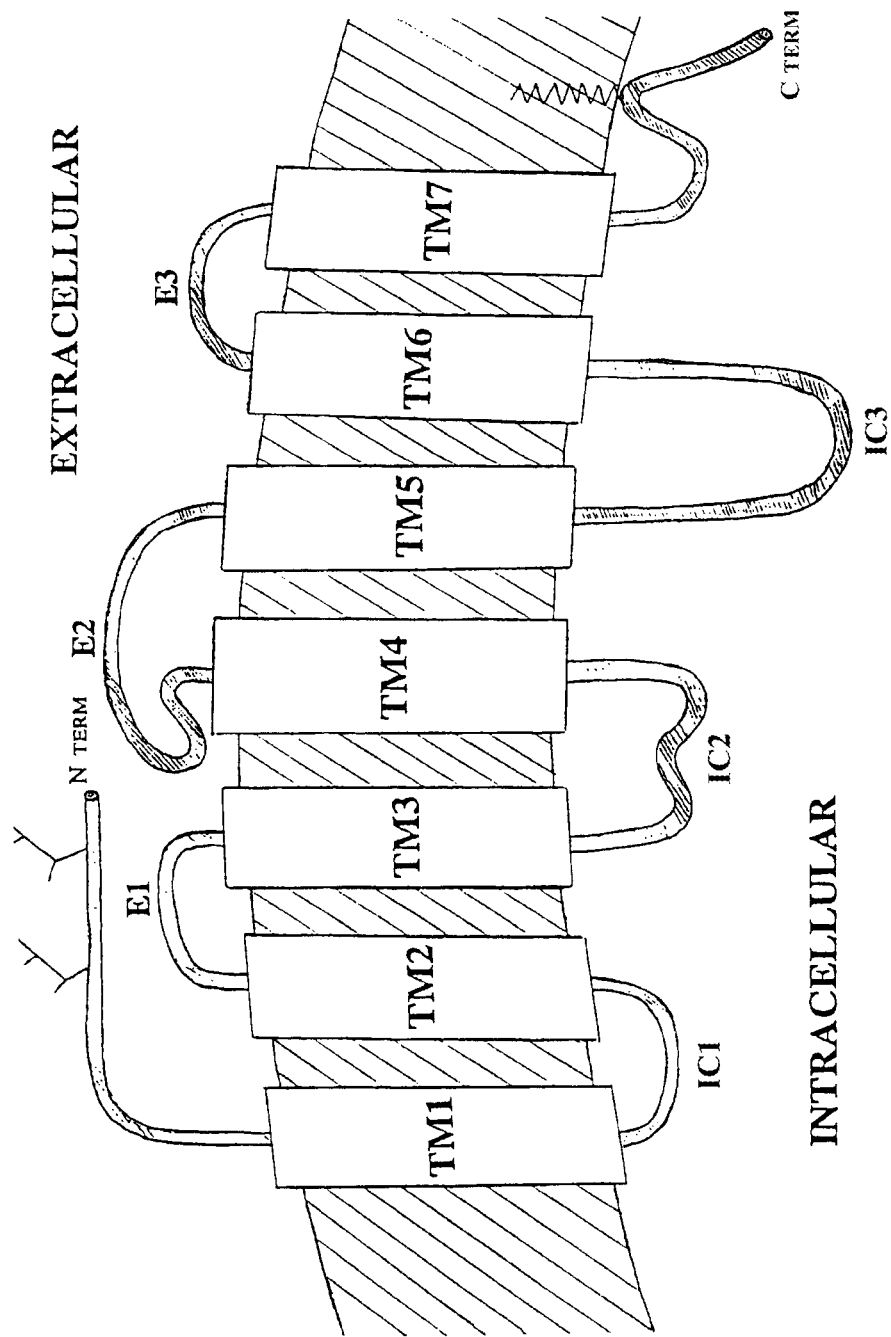
FIG. 1 is a schematic illustration of a GPCR, showing the canonical transmembrane regions (TM1, TM2, TM3, TM4, TM5, TM6, and TM7), intracellular regions (IC1, IC2, and IC3), and extracellular regions (EC1, EC2, and EC3).

"G-protein coupled receptors" or "GPCRs" are polypeptides that share a common structural motif, referred to herein as the "heptahelical domain", having seven regions of between 22 to 24 hydrophobic amino acids that form seven alpha helices, each of which spans a membrane. As illustrated in FIG. 1, each span is identified by number, i.e., transmembrane-1 (TM1), transmembrane-2 (TM2), etc. The transmembrane helices are joined by regions of amino acids between transmembrane-2 and transmembrane-3, transmembrane-4 and transmembrane-5, and transmembrane-6 and transmembrane-7 on the exterior, or "extracellular" side, of the cell membrane, referred to as "extracellular" regions 1, 2 and 3 (EC1, EC2 and EC3), respectively. The transmembrane helices are also joined by regions of amino acids between transmembrane-1 and transmembrane-2, transmembrane-3 and transmembrane-4, and transmembrane-5 and transmembrane-6 on the interior, or "intracellular" side, of the cell membrane, referred to as "intracellular" regions 1, 2 and 3 (IC1, IC2 and IC3), respectively. The "carboxy" ("C") terminus of the receptor lies in the intracellular space within the cell, and the "amino" ("N") terminus of the receptor lies in the extracellular space outside of the cell. GPCR structure and classification is generally well known in the art, and further discussion of GPCRs may be found in Probst, DNA Cell Biol. 1992 11:1-20; Marchese et al Genomics 23: 609-618, 1994; and the following books: Jürgen Wess (Ed) Structure-Function Analysis of G Protein-Coupled Receptors published by Wiley-Liss (1st edition; Oct. 15, 1999); Kevin R. Lynch (Ed) Identification and Expression of G Protein-Coupled Receptors published by John Wiley & Sons (March 1998) and Tatsuya Haga (Ed), G Protein-Coupled Receptors, published by CRC Press (Sep. 24, 1999); and Steve Watson (Ed) G-Protein Linked Receptor Factsbook, published by Academic Press (1st edition; 1994). A schematic representation of a typical GPCR is shown in FIG. 1.

A "family C" GPCR shares its plasma membrane topology with other GPCRs, as it is composed of an extracellular amino terminal domain (ATD) that is commonly referred to as having a bi-lobular "Venus-flytrap" module (VFTM), seven transmembrane spanning segments separated by alternating intracellular and extracellular loops (the "heptahelical domain"), and an intracellular carboxy terminal region. The most notable structural feature of the family C receptors is an unusually large ADT (up to 500-600 in length in certain cases) that contains the binding site for the endogenous agonist of the receptor. Unless otherwise indicated, if a particular GPCR is referred to herein (e.g., "mGluR5") the reference is to the receptor from humans as well as the ortholog of that receptor from other species (e.g., other mammals such as mouse, non-human primates, rat, dog, etc).

The term "naturally-occurring" in reference to a GPCR means a GPCR that is naturally produced (for example and not limitation, by a mammal or by a human). Such GPCRs are found in nature. The term "non-naturally occurring" in reference to a GPCR means a GPCR that is not naturally-occurring. Wild-type GPCRs that have been made constitutively active through mutation, and variants of naturally-occurring GPCRs, e.g., epitope-tagged GPCR and GPCRs lacking their native N-terminus are examples of non-naturally occurring GPCRs. Non-naturally occurring versions of a naturally occurring GPCR are activated by the same ligand as the naturally-occurring GPCR.

The term "ligand" means a molecule that specifically binds to a GPCR. A ligand may be, for example a polypeptide, a lipid, a small molecule, an antibody. A "native ligand" is a ligand that is an endogenous, natural ligand for a native GPCR. A ligand may be a GPCR "antagonist", "agonist", "partial agonist" or "inverse agonist", or the like.

A "modulator" is a ligand that increases or decreases a GPCR intracellular response when it is in contact with, e.g., binds, to a GPCR that is expressed in a cell. This term includes agonists, including partial agonists and inverse agonists, and antagonists.

A "deletion" is defined as a change in either amino acid or nucleotide sequence in which one or more amino acid or nucleotide residues, respectively, are absent as compared to an amino acid sequence or nucleotide sequence of a parental GPCR polypeptide or nucleic acid. In the context of a GPCR or a fragment thereof, a deletion can involve deletion of about 2, about 5, about 10, up to about 20, up to about 30 or up to about 50 or more amino acids. A GPCR or a fragment thereof may contain more than one deletion.

An "insertion" or "addition" is that change in an amino acid or nucleotide sequence which has resulted in the addition of one or more amino acid or nucleotide residues, respectively, as compared to an amino acid sequence or nucleotide sequence of a parental GPCR. "Insertion" generally refers to addition to one or more amino acid residues within an amino acid sequence of a polypeptide, while "addition" can be an insertion or refer to amino acid residues added at an N- or C-terminus, or both termini. In the context of a GPCR or fragment thereof, an insertion or addition is usually of about 1, about 3, about 5, about 10, up to about 20, up to about 30 or up to about 50 or more amino acids. A GPCR or fragment thereof may contain more than one insertion. Reference to particular GPCR or group of GPCRs by name, e.g., reference to the serotonin or histamine receptor, is intended to refer to the wild type receptor as well as active variants of that receptor that can bind to the same ligand as the wild type receptor and/or transduce a signal in the same way as the wild type receptor.

A "substitution" results from the replacement of one or more amino acids or nucleotides by different amino acids or nucleotides, respectively as compared to an amino acid sequence or nucleotide sequence of a parental GPCR or a fragment thereof. It is understood that a GPCR or a fragment thereof may have conservative amino acid substitutions which have substantially no effect on GPCR activity. By conservative substitutions is intended combinations such as gly, ala; val, ile, leu; asp, glu; asn, gln; ser, thr; lys, arg; and phe, tyr.

The term "biologically active", with respect to a GPCR, refers to a GPCR having a biochemical function (e.g., a binding function, a signal transduction function, or an ability to change conformation as a result of ligand binding) of a naturally occurring GPCR.

As used herein, the terms "determining," "measuring," "assessing," and "assaying" are used interchangeably and include both quantitative and qualitative determinations. Reference to an "amount" of a GPCR in these contexts is not intended to require quantitative assessment, and may be either qualitative or quantitative, unless specifically indicated otherwise.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term "fusion protein" or grammatical equivalents thereof is meant a protein composed of a plurality of polypeptide components, that while typically unjoined in their native state, are joined by their respective amino and carboxyl termini through a peptide linkage to form a single continuous polypeptide. Fusion proteins may be a combination of two, three or even four or more different proteins. The term polypeptide includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially pure" refers to a compound that is removed from its natural environment and is at least 60% free, at least 75% free, or at least 90% free from other components with which it is naturally associated.

A "coding sequence" or a sequence that "encodes" a selected polypeptide, is a nucleic acid molecule which can be transcribed (in the case of DNA) and translated (in the case of mRNA) into a polypeptide, for example, in a host cell when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence.

"Operably linked" refers to an arrangement of elements wherein the components so described are configured so as to perform their usual function. In the case of a promoter, a promoter that is operably linked to a coding sequence will effect the expression of a coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes comprising non-native nucleic acid sequences, and the like.

A "vector" is capable of transferring gene sequences to a host cell. Typically, "vector construct," "expression vector," and "gene transfer vector," mean any nucleic acid construct capable of directing the expression of a gene of interest and which can transfer gene sequences to host cells, which can be accomplished by genomic integration of all or a portion of the vector, or transient or inheritable maintenance of the vector as an extrachromosomal element. Thus, the term includes cloning, and expression vehicles, as well as integrating vectors.

An "expression cassette" comprises any nucleic acid construct capable of directing the expression of a gene/coding sequence of interest, which is operably linked to a promoter of the expression cassette. Such cassettes can be constructed into a "vector," "vector construct," "expression vector," or "gene transfer vector," in order to transfer the expression cassette into a host cell. Thus, the term includes cloning and expression vehicles, as well as viral vectors.

A first polynucleotide is "derived from" or "corresponds to" a second polynucleotide if it has the same or substantially the same nucleotide sequence as a region of the second polynucleotide, its cDNA, complements thereof, or if it displays sequence identity as described above.

A first polypeptide is "derived from" or "corresponds to" a second polypeptide if it is (i) encoded by a first polynucleotide derived from a second polynucleotide, or (ii) displays sequence identity to the second polypeptides as described above.

The term "stable, folded protein insertion" refers to a folded region of polypeptide that is inserted between two neighboring domains (e.g., the TM3 and TM4 domains of a GPCR), such that the domains are spaced relative to each other at a distance that allows them to interact as in the wild-type protein. When folded, such a domain does not readily become inactive or denatured. The term "stable, folded protein insertion" excludes an amino acid sequence of a fluorescent protein (e.g., GFP, CFP or YFP), and excludes amino acid sequences that are at least 90% identical to the entire IC2 loop of another wild type GPCR. The IC2 loop of a wild type GPCR does not contain stable, folded protein domain.

The term "active form" or "native state" of a protein is a protein that is folded in a way so as to be active. A GPCR is in its active form if it can bind ligand, alter conformation in response to ligand binding, and/or transduce a signal which may or may not be induced by ligand binding. An active or native protein is not denatured.

The term "stable domain" is a polypeptide domain that, when folded in its active form, is stable, i.e., does not readily become inactive or denatured.

The term "folds autonomously" indicates a protein that folds into its active form in a cell, without biochemical denaturation and renaturation of the protein, and without chaperones.

The term "naturally-occurring" refers to an object that is found in nature.

The term "non-naturally-occurring" refers to an object that is not found in nature.

DETAILED DESCRIPTION OF EXEMPLARY EMBODIMENTS

In the following description, the fusion protein is described first, followed by a discussion of the crystallization method in which the fusion protein may be employed.
Fusion Proteins As noted above, a fusion protein is provided. In certain embodiments, the fusion protein comprises: a) a first portion of a family C G-protein coupled receptor (GPCR), where the first portion comprises the TM1, TM2 and TM3 regions of the GPCR; b) a stable, folded protein insertion c) a second portion of the GPCR, where the second portion comprises the TM4, TM5, TM6 and TM7 regions of the GPCR. In particular embodiments, the stable, folded protein insertion spaces the ends of the TM3 region and the TM4 region of the GPCR at a distance (e.g., in the range of 6 Å to 16 Å) that does not abolish the activity of the GPCR. The stable, folded protein insertion provides a polar surface area for crystal lattice contacts, allowing the protein to be crystallized.

In very general terms, such a protein may be made by inserting into the IC2 region of the GPCR a stable, folded protein that holds the two flanking portions of the GPCR (i.e. the portion that lies N-terminal to the IC2 region and the portion that lies C-terminal to the IC2 region) together at a distance that is compatible with a functional GPCR in terms of pharmacologic and dynamic properties. For clarity, the terms "inserting" includes inserting a sequence between two amino acids in an existing region as well as inserting a sequence into a region in which amino acids have been deleted. As such, an "insertion" may be made by inserting a sequence between two amino acid residues in an IC2 region, or by replacing (i.e., substituting) at least one amino acid residue in an IC2 region with a sequence.
GPCRs Any family C GPCR is suitable for use in the subject methods, as long as it has TM3 and TM4 regions that are identifiable in the sequence of the GPCR. A discussion of the phylogenetic relationships between the different family C GPCRs are reviewed in Bräuner-Osborne, (Curr. Drug Targets 2007 8: 169-84), Wellendorph (Br J Pharmacol. 2009 156:869-84) and Hermans (Biochem J. 2001 359: 465-84), which are incorporated by reference for disclosure of a description of the structural and functional characteristics of family C GPCRs, as well examples of the same.

Family C GPCRs include: a) Calcium-sensing receptor-related GPCRs, including: calcium-sensing receptor (CASR) and GPRC6A (GPRC6A); b) GABAB (gamma-aminobutyric acid) receptors, including: GABAB receptor 1 (GABBR1); GABAB receptor 2 (GABBR2) and GPR156 (GPR156); c) metabotropic glutamate receptors (mGluR), including: mGluR1 (GRM1), mGluR2 (GRM2), mGluR3 (GRM3), mGluR4 (GRM4), mGluR5 (GRM5), mGluR6 (GRM6), mGluR7 (GRM7) and mGluR8 (GRM8); d) retinoic acid-inducible orphan G protein-coupled receptors (RAIG), including; RAIG1 (GPRC5A), RAIG2 (GPRC5B), RAIG3 (GPRC5C) and RAIG4 (GPRC5D); e) taste receptors, including: taste receptor, type 1, member 1 (TAS1R1), taste receptor, type 1, member 2 (TAS1R2), taste receptor, type 1, member 3 (TAS1R3); 0 orphan receptors, e.g., GPR158 (GPR158) and GPR179 (GPR179); and g) other GPCRs including the bride of sevenless protein vomeronasal receptor, type 2. Amino acid sequences of a representative number of Family C receptors are set forth in FIG. 4.

It is recognized that both native (naturally occurring) and altered native (non-naturally occurring) GPCRs may be used in the subject methods. In certain embodiments, therefore, an altered native GPCR (e.g. a native GPCR that is altered by an amino acid substitution, deletion and/or insertion) such that it binds the same ligand as a corresponding native GPCR, and/or couples to a G-protein as a result of the binding. In certain cases, at least the heptahelical domain of a GPCR employed herein may have an amino acid sequence that is at least 80% identical to, e.g., at least 90% identical, at least 85% identical, at least 90% identical, at least 95% identical, or at least 98% identical, to the corresponding sequence of a naturally occurring GPCR. A GPCR employed herein may optionally contain the extracellular amino terminal domain of a GPCR, and/or the C-terminal domain of a GPCR. Without the extracellular amino terminal domain, a Family C GPCR does not bind the native ligand. However, such a GPCR does bind allosteric modulators and can activate G proteins (see, e.g., Goudet et al. Proc. Natl. Acad. Sci. 2004 101: 378-383). Positive allosteric modulators (PAMs) enhance signalling whereas negative allosteric modulators (NAMs) dampen the response to ligand. In certain cases, however, a full length receptor may be employed. In other words, in certain embodiments, a native GPCR may be "trimmed back" from its N-terminus and/or its C-terminus to leave its heptahelical domain, prior to crystallization.

Figure 2:
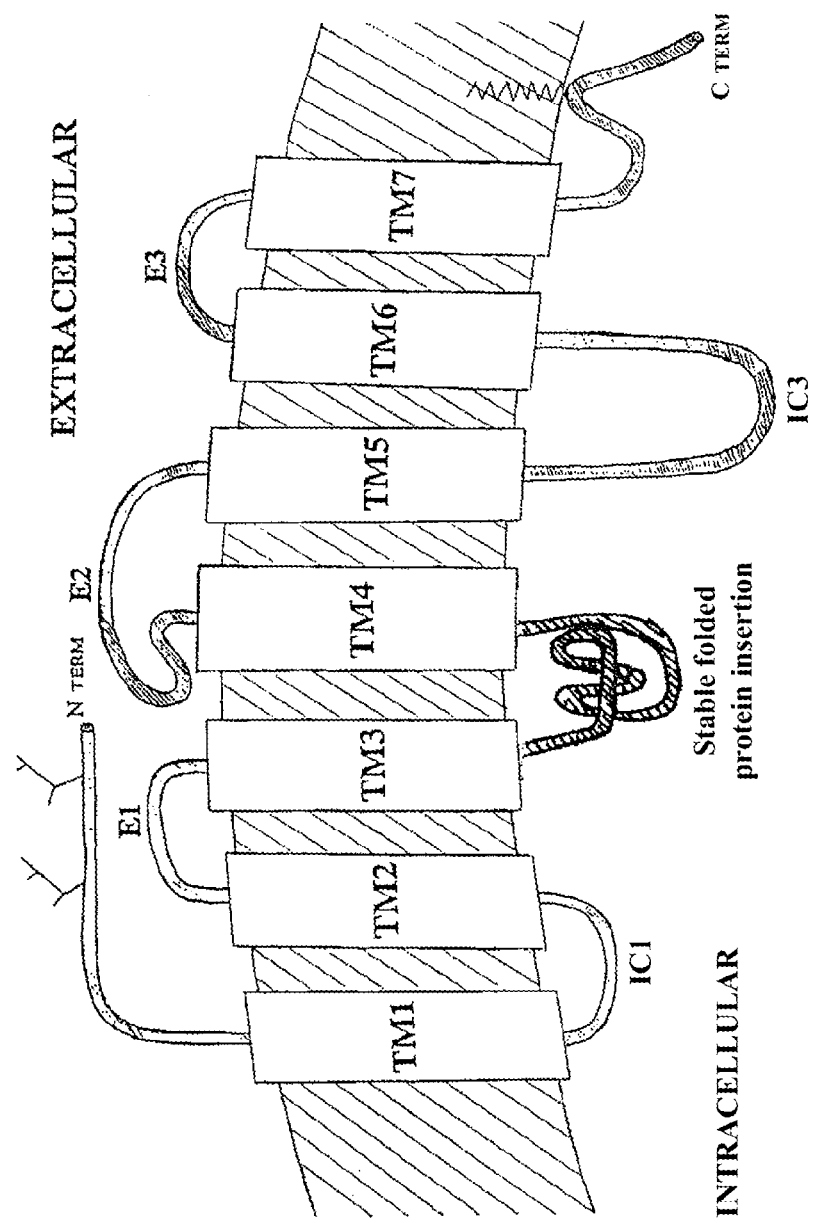
FIG. 2 is a schematic illustration of a subject fusion protein, showing a stable, folded protein insertion between the TM3 and TM4 regions of a GPCR.

In the subject methods, the region between the TM3 and TM4 regions of a GPCR (i.e., the IC2 region) is usually identified, and the amino acid sequence of a stable, folded insertion protein is inserted into that region to form a fusion protein. The stable, folded protein insertion spaces the TM3 and TM4 regions relative to one another. A schematic representation of the prototypical structure of a GPCR is provided in FIG. 1, where these regions, in the context of the entire structure of a GPCR, may be seen. A schematic representation of a subject fusion protein is shown in FIG. 2. In one embodiment, the IC2 loop of the GPCR is contains a stable, folded protein insertion. In particular embodiment, amino acids may be deleted from the IC2 loop of the GPCR in addition to inserting the stable, folded protein insertion into the loop.

The IC2 region of a GPCR lies in between transmembrane regions TM3 and TM4 and, may be in the range of about 15 amino acids to about 30 amino acids in length, for example. The TM3, IC2, and TM4 regions are readily discernable by one of skill in the art using, for example, a program for identifying transmembrane regions; once transmembrane regions TM3 and TM4 regions are identified, the IC2 region will be apparent. The TM3, IC2, and TM5 regions may also be identified using such methods as pairwise or multiple sequence alignment (e.g. using the GAP or BESTFIT of the University of Wisconsin's GCG program, or CLUSTAL alignment programs, Higgins et al., Gene. 1988 73:237-44), using a target GPCR and, for example, GPCRs of known structure.

Suitable programs for identifying transmembrane regions include those described by Moller et al., (Bioinformatics, 17:646-653, 2001). A particularly suitable program is called "TMHMM" Krogh et al., (Journal of Molecular Biology, 305:567-580, 2001). To use these programs via a user interface, a sequence corresponding to a GPCR or a fragment thereof is entered into the user interface and the program run. Such programs are currently available over the world wide web, for example at the website of the Center for Biological Sequence Analysis at cbs.dtu.dk/services/. The output of these programs may be variable in terms its format, however they usually indicate transmembrane regions of a GPCR using amino acid coordinates of a GPCR.

When TM regions of a GPCR polypeptide are determined using TMHMM, the prototypical GPCR profile is usually obtained: an N-terminus that is extracellular, followed by a segment comprising seven TM regions, and further followed by a C-terminus that is intracellular. TM numbering for this prototypical GPCR profile begins with the most N-terminally disposed TM region (TM1) and concludes with the most C-terminally disposed TM region (TM7).

Accordingly, in certain embodiments, the amino acid coordinates of the TM3, IC-2, and TM4 regions of a GPCR are identified by a suitable method such as TMHMM.

In certain cases, once the TM3-IC2-TM4 segment is identified for a GPCR, a suitable region of amino acids is chosen for substitution with the amino acid sequence of the a stable, folded protein insertion. In certain embodiments, the substituted region may be identified using conserved or semi-conserved amino acids in the TM3 and TM4 transmembrane regions. In certain embodiments and depending on the GPCR used, the N-terminus of the stable, folded protein insertion is linked to the amino acid that is 15 to 25 (e.g., 15, 16, 17, 18, 19, 20, 21, 22, 23, 24, or 25; e.g., 20-23) residues C-terminal to a conserved tyrosine in the TM3 of the GPCR, although linkages outside of this region are envisioned. In certain embodiments and depending on the GPCR used, the C-terminus of the stable, folded protein insertion may be linked to the amino acid that is 10 to 20 (e.g., 10, 11, 12, 13, 14, 15, 16, 17, 18, 19, or 20; e.g., 15-18) residues N-terminal a conserved glutamine in the beginning of the TM4 region of the GPCR, although linkages outside of this region are envisioned. In certain cases, the insertion may be placed between two amino acids in the IC2 region. Depending on which GPCR is being used, the insertion may placed immediately C-terminal to the amino acid that is 5, 6, 7, 8, 9, 10, 11, 12, 13, 14, 15, 16, 17, 18, 19, 20, 21, 22, 23, 24, 24, or 26 amino acids C-terminal of the end of the TM3 region, for example. In particular embodiments, this position may be optimized.

For GPCRs that contain no conserved tyrosine residue in TM3 or glutamine residue in TM4, positions for inserting an a stable, folded protein insertion can be determined based on two considerations: a) alignment of the sequence of the GPCR with receptor members of the same subfamily (which contained conserved proline residues in TM3 or TM4; b) by identifying the juxtaposition to the TM3/TM4 regions by hydrophobicity analysis.

In addition to introducing a stable, folded protein insertion into the IC2 region of a GPCR, as described above, in certain cases, the C-terminal region of the GPCR (which in some GPCRs may be C-terminal to a cysteine palmitoylation site, may be deleted. In certain cases, the 20-30 amino acids immediately C-terminal to the cysteine palmitoylation site are not deleted.

Stable, Folded Protein Insertions

In certain embodiments, a stable, folded protein insertion of a subject fusion protein may be a soluble, stable protein (e.g., a protein displaying resistance to thermal and chemical denaturation) that folds autonomously of the GPCR portion of the fusion protein, in a cell. In certain cases, the stable, folded protein insertion may have no cysteine residues (or may be engineered to have no cysteine residues) in order to avoid potential disulphide bonds between the stable, folded protein insertion and a GPCR portion of the fusion protein, or internal disulphide bonds. Stable, folded protein insertions are conformationally restrained, and are resistant to protease cleavage.

In certain cases, stable, folded protein insertions may contain most or all of the amino acid sequence of a polypeptide that is readily crystallized. Such proteins may be characterized by a large number of deposits in the protein data bank (www.rcsb.org) in a variety of space groups and crystal packing arrangements. While examples that employ lysozyme as stable, folded protein insertion are discussed below, the general principles may be used to employ any of a number of polypeptides that have the characteristics discussed above. Suitable stable, folded protein insertion candidates include those containing the amino acid sequence of proteins that are readily crystallized including, but not limited to: lysozyme, glucose isomerase, xylanase, trypsin inhibitor, crambin, ribonuclease. Other suitable polypeptides may be found at the BMCD database (Gilliland et al 1994. The Biological Macromolecule Crystallization Database, Version 3.0: New Features, Data, and the NASA Archive for Protein Crystal Growth Data. Acta Crystallogr. D50 408-413), as published to the world wide web.

In certain embodiments, the stable, folded protein insertion used may be at least 80% identical (e.g., at least 85% identical, at least 90% identical, at least 95% identical or at least 98% identical to a wild type protein. Many suitable wild type proteins, including non-naturally occurring variants thereof, are readily crystallizable.

In one embodiment, the autonomously folding stable domain may be of the lysozyme superfamily, which share a common structure and are readily crystallized. Such proteins are described in, e.g., Wohlkönig et al (Structural Relationships in the Lysozyme Superfamily: Significant Evidence for Glycoside Hydrolase Signature Motifs. PLoS ONE 2010 5: e15388).

As noted above, one such stable, folded protein insertion that may be employed in a subject fusion protein is lysozyme. Lysozyme is a highly crystallizable protein (see, e.g., Strynadka et al Lysozyme: a model enzyme in protein crystallography EXS 1996 75: 185-222) and at present over 200 atomic coordinates for various lysozymes, including many wild-type lysozymes and variants thereof, including lysozymes from phage T4, human, swan, rainbow trout, guinea fowl, soft-shelled turtle, tapes japonica, nurse shark, mouse sperm, dog, chicken, hen, cow, and phage P1, as well as man-made variants thereof, have been deposited in NCBI's structure database. A subject fusion protein may contain any of a wide variety of lysozyme sequences. See, e.g., Strynadka et al (*Lysozyme: a model enzyme in protein crystallography* (EXS. 1996; 75:185-222), Evrard et al (*Crystal structure of the lysozyme from bacteriophage lambda and its relationship with V and C-type lysozymes*) J. Mol. Biol. 1998 276:151-64), Forsythe et al (*Crystallization of chicken egg-white lysozyme from ammonium sulfate*. Acta Crystallogr D Biol Crystallogr. 1997 53:795-7), Remington et al (*Structure of the Lysozyme from Bacteriophage T4: An Electron Density Map at 2.4A Resolution*), Lyne et al (*Preliminary crystallographic examination of a novel fungal lysozyme from Chalaropsis*. J Biol Chem. 1990 265:6928-30), Marana et al. (*Crystallization, data collection and phasing of two digestive lysozymes from Musca domestica*. Acta Crystallogr Sect F Struct Biol Cryst Commun. 2006 62:750-2), Harada et al (*Preliminary X-ray crystallographic study of lysozyme produced by Streptomyces globisporus*. J Mol Biol. 1989 207:851-2) and Yao et al (*Crystallization and preliminary X-ray structure analysis of pigeon egg-white lysozyme*). J. Biochem. 1992 111:1-3).

The length of the stable, folded protein insertion may be between 80-500 amino acids, e.g., 100-200 amino acids in length, although stable, folded protein insertions having lengths outside of this range are also envisioned.

As noted above, the stable, folded protein insertion is not fluorescent or light-emitting. As such, the stable, folded protein insertion is not CFP, GFP, YFP, luciferase, or other light emitting, fluorescent variants thereof. In certain cases, a stable, folded protein insertion region does not contain a flexible polyglycine linker or other such conformationally unrestrained regions. In certain cases, the stable, folded protein insertion contains a sequence of amino acids from a protein that has a crystal structure that has been solved. In certain cases, the stable, folded protein insertion should not have highly flexible loop region characterized by high crystallographic temperature factors (i.e., high B-factors).

In certain cases, once a suitable polypeptide is identified, a stable, folded protein insertion may be designed by deleting amino acid residues from the N-terminus, the C-terminus or both termini of the polypeptide such that the closest alpha carbon atoms in the backbone at the termini of the polypeptide are spaced by a distance of in the range of 6 Å to 16 Å, e.g., 7 Å to 15 Å, 7 Å to 10 Å, 12 Å to 15 Å, 10 Å to 13 Å, or about 11 Å (i.e. 10 Å to 12 Å). The stable, folded protein insertion, disposed between the TM3 and TM4 regions of a GPCR, spaces those regions by that distance. The distance may be modified by adding or removing amino acids to or from the stable, folded protein insertion.

The amino acid sequence for an exemplary lysozyme fusion protein is set forth in FIG. 3.

FIG. 4 shows exemplary insertion points for a representative selection of family C GPCRs. The amino acid sequences of exemplary alternative insertions (which may be substituted into any of the sequences of FIG. 4 in place of the lysozyme sequence) are shown in FIG. 5. These sequences include the sequences of trypsin inhibitor, calbindin, barnase, xylanase and glucokinase although other sequences can be readily used.

Nucleic Acids

A nucleic acid comprising a nucleotide sequence encoding a subject fusion protein is also provided. A subject nucleic acid may be produced by any method. Since the genetic code and recombinant techniques for manipulating nucleic acid are known, the design and production of nucleic acids encoding a subject fusion protein is well within the skill of an artisan. In certain embodiments, standard recombinant DNA technology (Ausubel, et al, Short Protocols in Molecular Biology, 3rd ed., Wiley & Sons, 1995; Sambrook, et al., Molecular Cloning: A Laboratory Manual, Second Edition, (1989) Cold Spring Harbor, N.Y.) methods are used.

For example, site directed mutagenesis and subcloning may be used to introduce/delete/substitute nucleic acid residues in a polynucleotide encoding GPCR. In other embodiments, PCR may be used. Nucleic acids encoding a polypeptide of interest may also be made by chemical synthesis entirely from oligonucleotides (e.g., Cello et al., Science (2002) 297:1016-8).

In certain embodiments, the codons of the nucleic acids encoding polypeptides of interest are optimized for expression in cells of a particular species, particularly a mammalian, e.g., human, species. Vectors comprising a subject nucleic acid are also provided. A vector may contain a subject nucleic acid, operably linked to a promoter.

A host cell (e.g., a host bacterial, mammalian, insect, plant or yeast cell) comprising a subject nucleic acid is also provided as well a culture of subject cells. The culture of cells may contain growth medium, as well as a population of the cells. The cells may be employed to make the subject fusion protein in a method that includes culturing the cells to provide for production of the fusion protein. In many embodiments, the fusion protein is directed to the plasma membrane of the cell, and is folded into its active form by the cell.

The native form of a subject fusion protein may be isolated from a subject cell by conventional technology, e.g., by solubilization, precipitation, centrifugation, affinity, filtration or any other method known in the art. For example, affinity chromatography (Tilbeurgh et al., (1984) FEBS Lett. 16:215); ion-exchange chromatographic methods (Goyal et al., (1991) Biores. Technol. 36:37; Fliess et al., (1983) Eur. J. Appl. Microbiol. Biotechnol. 17:314; Bhikhabhai et al., (1984) J. Appl. Biochem. 6:336; and Ellouz et al., (1987) Chromatography 396:307), including ion-exchange using materials with high resolution power (Medve et al., (1998) J. Chromatography A 808:153; hydrophobic interaction chromatography (Tomaz and Queiroz, (1999) J. Chromatography A 865:123; two-phase partitioning (Brumbauer, et al., (1999) Bioseparation 7:287); ethanol precipitation; reverse phase HPLC; chromatography on silica or on a cation-exchange resin such as DEAE; chromatofocusing; SDS-PAGE; ammonium sulfate precipitation; or size exclusion chromatography using, e.g., Sephadex G-75, may be employed.

In particular embodiments, the GPCR, e.g., the N- or C-terminus of the GPCR or an external loop of the GPCR, may be tagged with an affinity moiety, e.g., a his tag, GST, MBP, flag tag, or other antibody binding site, in order to facilitate purification of the GPCR fusion protein by affinity methods.

Before crystallization, a subject fusion protein may be assayed to determine if the fusion protein is active, e.g., can bind ligand and change in conformation upon ligand binding, and if the fusion protein is resistant to protease cleavage. Such assays are well known in the art.

In certain cases the subject fusion protein may be combined with a ligand for the GPCR of the fusion protein prior to crystallization.

Crystallization Methods

A subject fusion protein may be crystallized using any of a variety of crystallization methods, many of which are reviewed in Caffrey (*Membrane protein crystallization.* J Struct. Biol. 2003 142:108-32) and those that employ detergent micelles, bicelles and lipidic cubic phase (LCP). In general terms, the methods are lipid-based methods that include adding lipid to the fusion protein prior to crystallization. Such methods have previously been used to crystallize other membrane proteins. Many of these methods, including the lipidic cubic phase crystallization method and the bicelle crystallization method, exploit the spontaneous self-assembling properties of lipids and detergent as vesicles (vesicle-fusion method), discoidal micelles (bicelle method), and liquid crystals or mesophases (in meso or cubic-phase method). Lipidic cubic phases crystallization methods are described in, for example: Landau et al, *Lipidic cubic phases: a novel concept for the crystallization of membrane proteins.* Proc. Natl. Acad. Sci. 1996 93:14532-5; Gouaux, It's not just a phase: crystallization and X-ray structure determination of bacteriorhodopsin in lipidic cubic phases. Structure. 1998 6:5-10; Rummel et al, *Lipidic Cubic Phases: New Matrices for the Three-Dimensional Crystallization of Membrane Proteins.* J. Struct. Biol. 1998 121:82-91; and Nollert et al *Lipidic cubic phases as matrices for membrane protein crystallization* Methods. 2004 34:348-53, which publications are incorporated by reference for disclosure of those methods. Bicelle crystallization methods are described in, for example: Faham et al *Crystallization of bacteriorhodopsin from bicelle formulations at room temperature.* Protein Sci. 2005 14:836-40. 2005 and Faham et al, *Bicelle crystallization: a new method for crystallizing membrane proteins yields a monomeric bacteriorhodopsin structure.* J Mol Biol. 2002 Feb. 8; 316(1):1-6, which publications are incorporated by reference for disclosure of those methods.

In particular cases, a GPCR may be crystallized using methods described in Rosenbaum et al (Nature. 2011 469: 236-40), Cherezov et al (Science. 2007 318:1258-65), Rosenbaum (Science. 2007 318:1266-73) and Rasmussen et al (Nature. 2007 450:383-7), among others. Such methods have been used to crystallize other GPCRs containing a lysozyme fusion.

In particular embodiments, the GPCR may be co-crystallized with or tested for activity using an allosteric modulator for the GPCR. Exemplary allosteric modulators for Family C GPCRs include those listed in Table 1 and described in Table 2 of Conn (Nature Reviews: Drug Discovery 2009 8: 41-54; incorporated by references), which are shown below. Others are known.

TABLE 1

| Receptor | Modulator example(s) |
| --- | --- |
| Calcium sensing receptor | Fendeline; cinacalcet; NPS 467; NPS 568; L-amino acids; NPS 2143; calhex 231 |
| GABA | CGP7930; CGP13501; GS39783 |
| mGluR$_1$ | (−)-C PC C OEt; Ro 67-7476; Ro 01-6128; BAY36-7620; [$^3$H]R214127; NPS 2390; EM-TBPC; cis-64a; JNJ 16259685 |
| mGluR$_2$ | LY487379; BINA; LY181837; Ro 67-6221 |
| mGluR$_4$ | SIB-1893; MPEP; (−)-PHCCC; VU0155041; VU0080421 |
| mGluR$_5$ | MPEP; MTEP; DFB; DCB; DMeOB; CPPHA; CDPPB: VU-29; ADX-47273 |
| mGluR$_7$ | AMN082 |

TABLE 2

| Potential indications for allosteric modulators of mGluRs | | |
| --- | --- | --- |
| compound structure | compound name (reference from Conn) | mglur subtype |
| Pain | | |
| 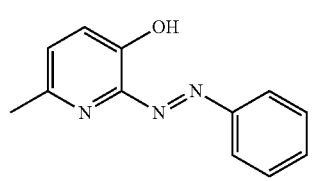 [SMILES: Cc1ccc(O)c(/N=N/c2ccccc2)n1] | CPCCOEt (27) | 1 NAM |
| Anxiety, fragile X syndrome, GERD, chronic pain, depression, migraine | | |
| | SIB-1757 (28) | 5 NAM |

TABLE 2-continued
Potential indications for allosteric modulators of mGluRs
| compound structure | compound name (reference from Conn) | mglur subtype |
|---|---|---|
| 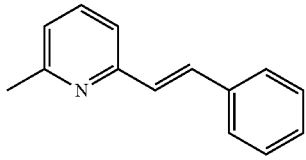 | SIB-1893 (28) | 5 NAM |
| 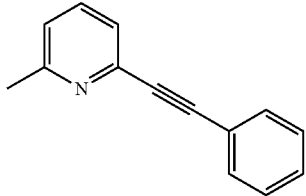 | MPEP (29) | 5 NAM |
| 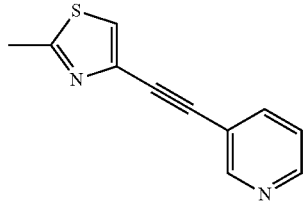 | MTEP (30) | 5 NAM |
| 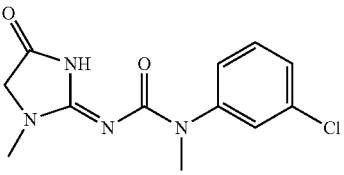 [SMILES: CN1CC(=O)N/C1=N\C(=O)N(C)c1cccc(Cl)c1] | Fenobam (34) | 5 NAM |
| 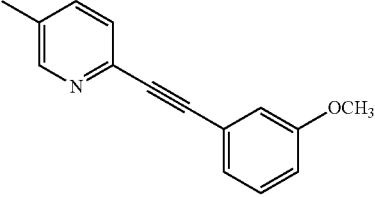 [SMILES: COc1cccc(C#Cc2ccc(C)cn2)c1] | M-5MPEP (41) | 5 Partial antagonist |
| 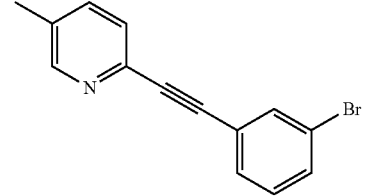 [SMILES: Cc1ccc(C#Cc2cccc(Br)c2)nc1] | Br-5MPEPy (41) | 5 Partial antagonist |
Schizophrenia, cognition, extinction
| | DFB (48) | 5 PAM |
|---|---|---|
| 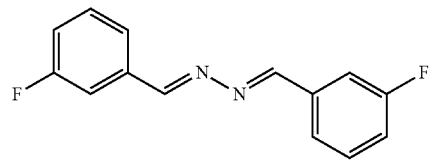 [SMILES: Fc1cccc(/C=N/N=C/c2cccc(F)c2)c1] | | |

TABLE 2-continued
Potential indications for allosteric modulators of mGluRs
| compound structure | compound name (reference from Conn) | mglur subtype |
|---|---|---|
| 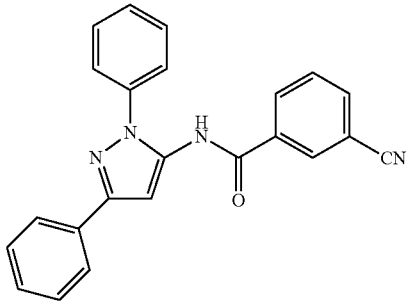 [SMILES: N#Cc1cccc(C(=O)Nc2cc(-c3ccccc3)nn2-c2ccccc2)c1] | CDPPB (51) | 5 PAM |
| 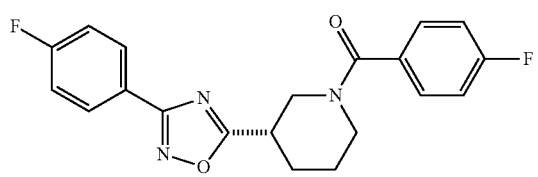 | ADX47273 (56) | 5 PAM |
| Anxiety disorders, schizophrenia | | |
| 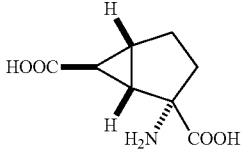 [SMILES: N[C@@]1(C(=O)O)CC[C@H]2[C@H](C(=O)O)[C@H]21] | LY354740 (58) | 2/3 agonist |
| 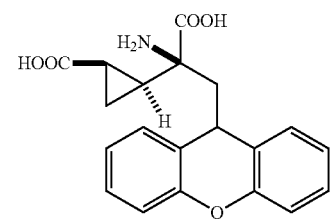 [SMILES: N[C@](CC1c2ccccc2Oc2ccccc21)(C(=O)O)[C@H]1C[C@H]1C(=O)O] | LY341495 | 2/3 antagonist |
| 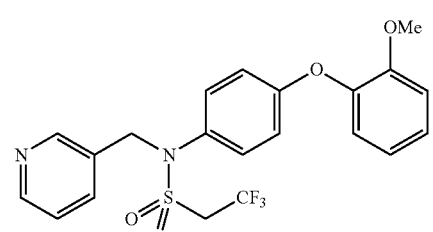 | LY487379 (66) | 2 PAM |
| 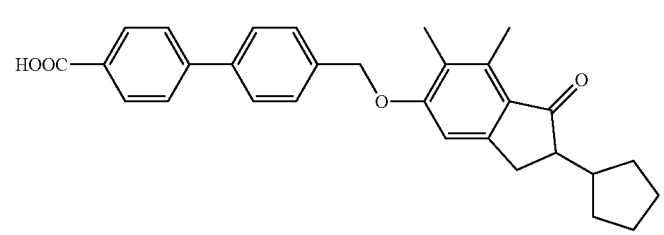 [SMILES: Cc1c(OCc2ccc(-c3ccc(C(=O)O)cc3)cc2)cc2c(c1C)C(=O)C(C1CCCC1)C2] | BINA (70) | 2 PAM |
| Parkinson's disease, movement disorders | | |

TABLE 2-continued

Potential indications for allosteric modulators of mGluRs

| compound structure | compound name (reference from Conn) | mglur subtype |
|---|---|---|
| 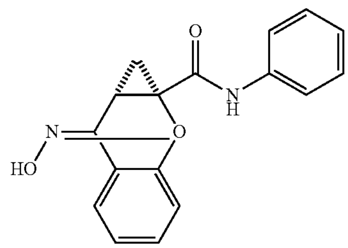 | (−)-PHCCC (86, 88) | 4 PAM |
| 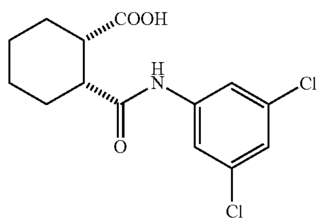 [SMILES: O=C(O)[C@H]1CCCC[C@H]1C(=O)Nc1cc(Cl)cc(Cl)c1] | VU0155041 (87 | 4 PAM/ Allosteric agonist |

Also provided is a method of determining a crystal structure. This method may comprise receiving an above described fusion protein, crystallizing the fusion protein to produce a crystal; and obtaining atomic coordinates of the fusion protein from the crystal. The fusion protein may be received from a remote location (e.g., a different laboratory in the same building or campus, or from a different campus or city), and, in certain embodiments, the method may also comprise transmitting the atomic coordinates, e.g., by mail, e-mail or using the internet, to the remote location or to a third party.

A method for producing a GPCR crystal is provided. This method may comprise: a) isolating a subject GPCR fusion protein; and b) crystallizing the isolated protein, thereby producing a GPCR crystal.

In other embodiments, the method may comprise forwarding a fusion protein to a remote location where the protein may be crystallized and analyzed, and receiving the atomic coordinates of the fusion protein.

Computer Modeling and Computer Systems

In certain embodiments, the above-described computer readable medium may further comprise programming for displaying a molecular model of a GPCR crystallized by the instant method, programming for identifying a compound that binds to the GPCR and/or a database of structures of known test compounds, for example. A computer system comprising the computer-readable medium is also provided. The model may be displayed to a user via a display, e.g., a computer monitor, for example.

The atomic coordinates may be employed in conjunction with a modeling program to provide a model of the GPCR. As used herein, the term "model" refers to a representation in a tangible medium of the three dimensional structure of the a GPCR or a complex of the same. For example, a model can be a representation of the three dimensional structure in an electronic file, on a display, e.g., a computer screen, on a piece of paper (i.e., on a two dimensional medium), and/or as a ball-and-stick figure. Physical three-dimensional models are tangible and include, but are not limited to, stick models and space-filling models. The phrase "imaging the model on a computer screen" refers to the ability to express (or represent) and manipulate the model on a computer screen using appropriate computer hardware and software technology known to those skilled in the art. Such technology is available from a variety of sources including, for example, Evans and Sutherland, Salt Lake City, Utah, and Biosym Technologies, San Diego, Calif. The phrase "providing a picture of the model" refers to the ability to generate a "hard copy" of the model. Hard copies include both motion and still pictures. Computer screen images and pictures of the model can be visualized in a number of formats including space-filling representations, backbone traces, ribbon diagrams, and electron density maps. Exemplary modeling programs include, but are not limited to PYMOL, GRASP, or O software, for example.

In another embodiment, the invention provides a computer system having a memory comprising the above-described atomic coordinates; and a processor in communication with the memory, wherein the processor generates a molecular model having a three dimensional structure representative of a GPCR or a complex of the same. The processor can be adapted for identifying a candidate compound having a structure that is capable of binding to the a GPCR or a complex of the same, for example.

In the present disclosure, the processor may execute a modeling program which accesses data representative of the GPCR structure. In addition, the processor also can execute another program, a compound modeling program, which uses the three-dimensional model of the GPCR or a complex of the same to identify compounds having a chemical structure that binds to the GPCR or a complex of the same. In one embodiment the compound identification program and the structure modeling program are the same program. In another embodiment, the compound identification program and the structure modeling program are different programs, which programs may be stored on the same or different storage medium.

A number of exemplary public and commercial sources of libraries of compound structures are available, for example the Cambridge Structural Database (CSD), the Chemical Directory (ACD) from the company MDL (US), ZINC (Irwin and Shoichet, J. Chem. Inf Model. (2005) 45:177-82) as well as various electronic catalogues of publicly available compounds such as the National Cancer Institute (NCI, US) catalogue, ComGenex catalogue (Budapest, Hungary), and Asinex (Moscow, Russia). Such libraries may be used to allow computer-based docking of many compounds in order to identify those with potential to interact with the GPCR using the atomic coordinates described herein.

In certain cases, the method may further comprise a testing a compound to determine if it binds and/or modulates the GPCR or a complex of the same, using the atomic coordinates provided herein. In some embodiments, the method may further comprise obtaining the compound (e.g., purchasing or synthesizing the compound) and testing the compound to determine if it modulates (e.g., activates or inhibits) the GPCR e.g., acts an agonist, antagonist or inverse agonist of the GPCR).

In some embodiments, the method employs a docking program that computationally tests known compounds for binding to the GPCR or complex of the same. Structural databases of known compounds are known in the art. In certain cases, compounds that are known to bind and modulate the GPCR or complex of the same may be computationally tested for binding to GPCR or complex of the same, e.g., in order to identify a binding site and/or facilitate the identification of active variants of an existing compound. Such compounds include compounds that are know to be agonists of the GPCR. In other cases, the method may include designing a compound that binds to the GPCR, either de novo, or by modifying an existing compound that is known to bind to the GPCR.

A method that comprises receiving a set of atomic coordinates for the GPCR or complex of the same; and identifying a compound that binds to said GPCR or complex of the same using the coordinates is also provided, as is a method comprising: forwarding to a remote location a set of atomic coordinates for the GPCR or complex of the same; and receiving the identity of a compound that binds to the GPCR or complex of the same.

In certain embodiments, a computer system comprising a memory comprising the atomic coordinates of a GPCR or complex of the same is provided. The atomic coordinates are useful as models for rationally identifying compounds that bind to the GPCR or complex of the same. Such compounds may be designed either de novo, or by modification of a known compound, for example. In other cases, binding compounds may be identified by testing known compounds to determine if the "dock" with a molecular model of the GPCR. Such docking methods are generally well known in the art.

The structure data provided can be used in conjunction with computer-modeling techniques to develop models of ligand-binding sites on the GPCR or complex of the same selected by analysis of the crystal structure data. The site models characterize the three-dimensional topography of site surface, as well as factors including van der Waals contacts, electrostatic interactions, and hydrogen-bonding opportunities. Computer simulation techniques are then used to map interaction positions for functional groups including but not limited to protons, hydroxyl groups, amine groups, divalent cations, aromatic and aliphatic functional groups, amide groups, alcohol groups, etc. that are designed to interact with the model site. These groups may be designed into a candidate compound with the expectation that the candidate compound will specifically bind to the site.

The ability of a candidate compound to bind to a GPCR can be analyzed prior to actual synthesis using computer modeling techniques. Only those candidates that are indicated by computer modeling to bind the target with sufficient binding energy (i.e., binding energy corresponding to a dissociation constant with the target on the order of $10^{-2}$ M or tighter) may be synthesized and tested for their ability to bind to and modulate the GPCR. Such assays are known to those of skill in the art. The computational evaluation step thus avoids the unnecessary synthesis of compounds that are unlikely to bind the GPCR with adequate affinity.

A candidate compound may be computationally identified by means of a series of steps in which chemical entities or fragments are screened and selected for their ability to associate with individual binding target sites on the GPCR. One skilled in the art may use one of several methods to screen chemical entities or fragments for their ability to associate with the GPCR, and more particularly with target sites on the GPCR. The process may begin by visual inspection of, for example a target site on a computer screen, based on the coordinates, or a subset of those coordinates. Selected fragments or chemical entities may then be positioned in a variety of orientations or "docked" within a target site of the GPCR as defined from analysis of the crystal structure data. Docking may be accomplished using software such as Quanta (Molecular Simulations, Inc., San Diego, Calif.) and Sybyl (Tripos, Inc. St. Louis, Mo.) followed by energy minimization and molecular dynamics with standard molecular mechanics forcefields such as CHARMM (Molecular Simulations, Inc., San Diego, Calif.) and AMBER (University of California at San Francisco).

Specialized computer programs may also assist in the process of selecting fragments or chemical entities. These include but are not limited to: GRID (Goodford, P. J., "A Computational Procedure for Determining Energetically Favorable Binding Sites on Biologically Important Macromolecules," J. Med. Chem., 28, pp. 849-857 (1985)); GRID is available from Oxford University, Oxford, UK; MCSS (Miranker, A. and M. Karplus, "Functionality Maps of Binding Sites: A Multiple Copy Simultaneous Search Method," Proteins: Structure, Function and Genetics, 11, pp. 29-34 (1991)); MCSS is available from Molecular Simulations, Inc., San Diego, Calif.; AUTODOCK (Goodsell, D. S. and A. J. Olsen, "Automated Docking of Substrates to Proteins by Simulated Annealing," Proteins: Structure, Function, and Genetics, 8, pp. 195-202 (1990)); AUTODOCK is available from Scripps Research Institute, La Jolla, Calif.; DOCK (Kunts, I. D., et al. "A Geometric Approach to Macromolecule-Ligand Interactions," J. Mol. Biol., 161, pp. 269-288 (1982)); DOCK is available from University of California, San Francisco, Calif.; CERIUS II (available from Molecular Simulations, Inc., San Diego, Calif.); and Flexx (Raret, et al. J. Mol. Biol. 261, pp. 470-489 (1996)).

Utility

The above-described crystals may be used to obtain to obtain the atomic coordinates of at least the heptahelical part of the fusion protein. In certain embodiments, a method for obtaining an X-ray diffraction pattern is provided. This method may generally comprise: a) exposing a crystal of a GPCR fusion protein to a source of X-rays, wherein the GPCR fusion protein is described above; and b) collecting an X-ray diffraction pattern for the crystal. In certain cases, the method may further comprises resolving the diffraction pattern to provide a set of atomic coordinates for the GPCR. The GPCR may be analyzed by a) obtaining atomic coordinates of a GPCR, wherein said atomic coordinates are produced by subjecting crystals of a subject GPCR fusion protein to X-ray diffraction analysis; and b) analyzing said GPCR using the atomic coordinates. In these embodiments, the obtaining can be receiving or accessing a file stored on a computer. The atomic coordinates may be provided on a computer readable medium. In certain embodiments, a computer readable storage medium comprising atomic coordinates for a GPCR is provided, where the atomic coordinates are produced by: a) producing crystals of a subject GPCR fusion protein; and b) subjecting the crystals to X-ray diffraction analysis. The crystals can be employed to design or identify compounds that modulate the GPCR.

In order to further illustrate certain aspects of the present invention, the following specific examples are given with the understanding that they are being offered to illustrate the present invention and should not be construed in any way as limiting its scope.

EXAMPLES

In order to obtain high-resolution structural information on the MGluR5, the T4 lysozyme (T4L) protein is inserted into the IC2 loop of the GPCR. The N- and C-terminal tails are also eliminated. The fusion protein is crystallized in lipidic cubic phase.

mGluR5 crystallization is done by inserting into the ICL2 of that protein a well-structured, soluble domain that aids in the formation of lattice contacts. The initial criteria for choosing the inserted soluble protein are that the amino and carboxyl termini would approximate the predicted distance between the cytoplasmic ends of helix III and helix IV, and that the protein would crystallize under a variety of conditions. T4L is a small, stable protein that fulfills these criteria.

DNA encoding the T4L protein (C54T, C97A) (M. Matsumura, W. J. Becktel, M. Levitt, B. W. Matthews, Proc. Natl. Acad. Sci. USA 86, 6562 (1989)) is initially cloned into the human mGluR5, between residues K677 and K678 (see FIG. 3). In addition, the receptor was truncated at both ends. Further optimization is carried out to reduce the length of the junction between the receptor and the T4L termini, to optimize expression and activity.

Methods

Molecular Biology for Generation of Mammalian and Sf9 Expression Constructs.

The insect cell expression plasmid that is used in this method is described in X. Yao et al., (*Nat Chem Biol* 2, 417 (2006). The wild-type coding sequence of the human mGluR5 (starting at Ser555) was cloned into the pFastbac1 Sf-9 expression vector (Invitrogen) with the Flag epitope tag at the amino terminus, and the construct was further modified. A synthetic DNA cassette encoding the T4 Lysozyme protein was made by overlapping extension PCR using 50-base oligonucleotides. This cassette was amplified and inserted into the mGluR5 construct between K677 and K678 (see FIG. 3), using the Quickchange Multi protocol (Stratagene). The corresponding mammalian cell expression plasmid is made by amplifying the entire fusion gene and cloning it into pCDNA3 (Invitrogen). Further deletions in the Sf9 and mammalian cell constructs are made using appropriate synthetic oligonucleotides in the Quickchange Multi protocol (Stratagene). The construct was confirmed by sequencing. The amino acid sequence of the encoded fusion protein is shown in FIG. 3.

Expression in HEK293 Cells and Functional Characterization by Ligand Binding.

HEK293 cells were cultured on plastic dishes at 37° C. with 5% $CO_2$ in Dulbecco's modified Eagle's medium (Cellgro) with 5% fetal bovine serum. For an individual expression experiment, cells at confluency were split, and approximately 100,000 cells were used to seed glass cover slips in the same medium. After 2 d, cells are transfected with the addition of 1 μg of a given pCDNA3-receptor plasmid and 3 μl of Fugene 6 reagent (Roche). 48 h after transfection, cells were harvested and membranes prepared for ligand binding analysis.

Figure 6:
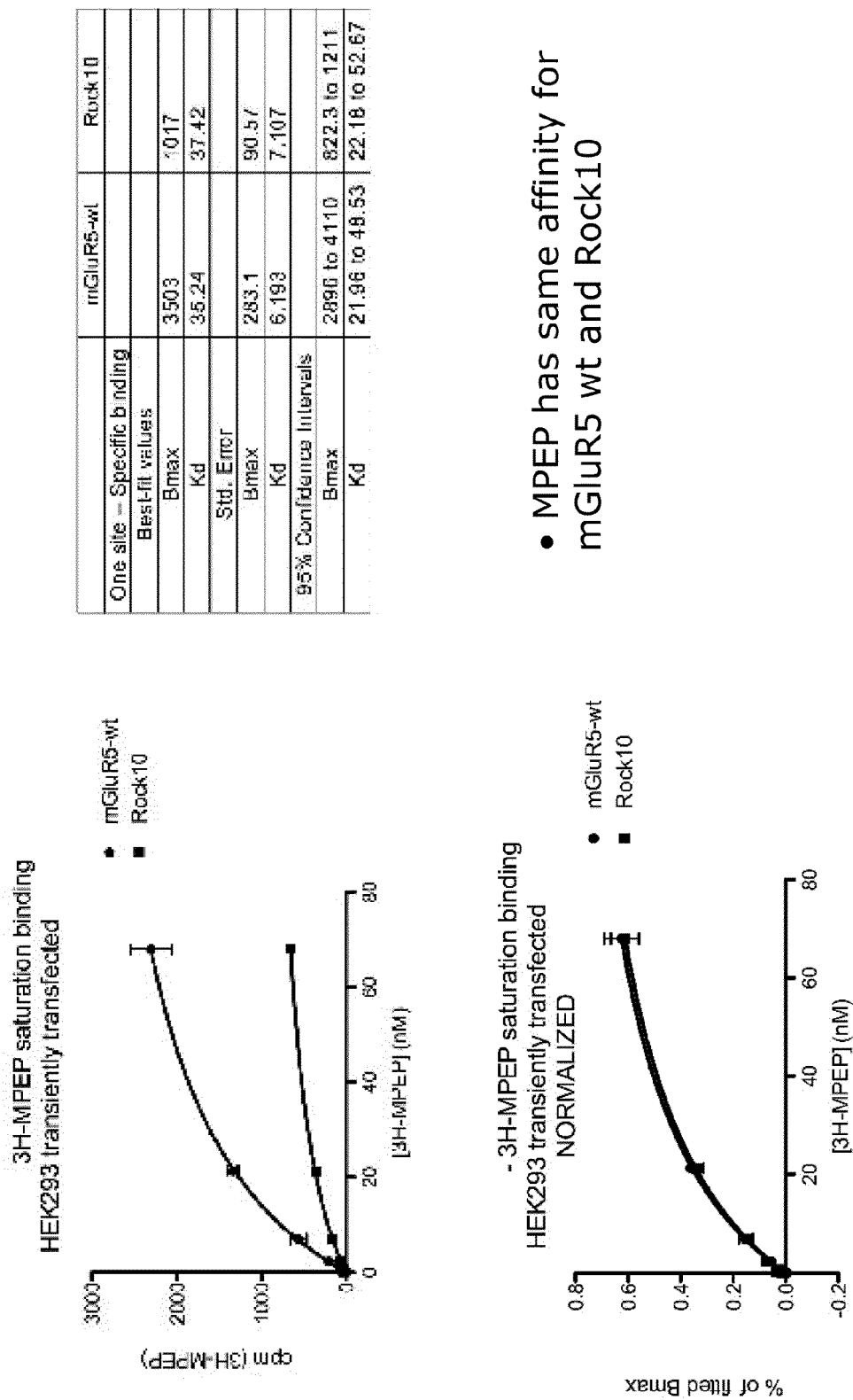
FIG. 6 shows two graphs and a table demonstrating that MPEP has same affinity for mGluR5 as Rock10, the fusion protein defined in FIG. 3.

$^3$H-MPEP (a negative allosteric modulator that binds to the transmembrane domains of mGluR5) was used to detect functional mGluR5 in HEK293 cell membranes (see FIG. 6).

Expression and Purification of mGluR5-T4L from Baculovirus-Infected Sf9 Cells.

Recombinant baculovirus are made from pFastbac1-mGluR2-T4L using the Bac-to-Bac system (Invitrogen), as described previously (X. Yao et al., *Nat Chem Biol* 2, 417 (2006)). The mGluR5-T4L protein is expressed in Sf9 insect cells infected with this baculovirus, and solubilized according to previously described methods (B. K. Kobilka, *Anal Biochem* 231, 269 (1995)). Dodecylmaltoside-solubilized receptor with the N-terminal FLAG epitope (DYKDDDA; SEQ ID NO:22) is purified by M1 antibody affinity chromatography (Sigma) and further purified by Sepharose chromatography to isolate only functional GPCR. Eluted receptor is re-bound to M1 FLAG resin, and ligand exchange is performed on the column. Protein is eluted from this final column with 0.2 mg/ml FLAG peptide in HLS buffer (0.1% dodecylmaltoside, 20 mM Hepes, 100 mM NaCl, pH 7.5) plus other reagents. Any N-linked glycolsylations is removed by treatment with PNGaseF (NEB). Protein is concentrated from ~5 mg/ml to 50 mg/ml with a 100 kDa molecular weight cut-off Vivaspin concentrator (Vivascience), and dialyzed against HLS buffer plus other reagents.

Lipidic Cubic Phase Crystallization

For lipidic cubic phase (LCP) crystallization, trials are performed using an in meso crystallization robot. 24-well glass sandwich plates (S1, S2) are filled with 25 or 50 nL protein-laden LCP drops overlaid by 0.8 μL of precipitant solution in each well and sealed with a glass coverslip. All operations starting from mixing lipid and protein are performed at room temperature (~21-23° C.). Trials are performed by varying the concentrations of, e.g., PEG 400, sodium sulfate, Bis-tris propane pH 6.5-7.0 and 1,4-butanediol using cholesterol in monoolein as the host lipid. Crystals are obtained in, e.g., 30-35% (v/v) PEG 400, 0.1-0.2 M sodium sulfate, 0.1 M Bis-tris propane pH 6.5-7.0 and 5-7% (v/v) 1,4-butanediol using 8-10% (w/w) cholesterol in monoolein as the host lipid. Other conditions may yield better crystals. PEG 400 and sulfate ion are used for crystallization, and the addition of cholesterol and 1,4-butanediol improved crystals size and shape enabling high-resolution diffraction. Additions of phospholipids (dioleoylphosphatidylcholine, dioleoylphosphatidylethanolamine, asolectin) alone and in combinations with cholesterol to the main host LCP lipid monoolein are also tried.

Crystal Harvesting

Crystals are harvested directly from the glass sandwich plates, even though these plates have been specifically designed for screening and optimization (S1, S2). Crystals are scooped directly from the LCP using 30 or 50 μm aperture MiTeGen MicroMounts and plunged into liquid nitrogen. Care is taken to drag as little as possible lipid around the crystal to decrease unwanted background scattering.

Data Collection

X-ray data is collected on the 23ID-B beamline (GM/CA CAT) at the Advanced Photon Source, Argonne, Ill. using a 10 μm minibeam (wavelength 1.0332 Å) and a MarMosaic 300 CCD detector. Several complete datasets are collected from single crystals at resolution expected to be between 2.8 and 3.5 Å using 5× attenuated beam, 5 s exposure and 1° oscillation per frame. Therefore, 10-20° wedges of high-resolution data could be collected from more than 40 crystals. Some of the best datasets are combined from independent crystals, scaling them against the lower resolution full dataset to obtain complete high resolution data.

Data Processing

Initial indexing of lattice parameters in spacegroup C2 and crystal orientation are performed using HKL2000. The refined lattice parameters and space group are implemented in the data processing program XDS for spot integration which models error explicitly for radiation decay, absorption, and rotation. The data, when obtained, is used as a scaling reference for incorporation of additional wedges of data collected at a much higher exposure. Each new dataset is indexed in XDS using the original unit cell parameters as constants which were then refined along with the crystal orientation, beam geometry, and mosaicity parameters. The refinement is generally stable, resulting in very similar unit cell constants which enabled subsequent scaling. All of the integrated wedges of data are then tested individually against the scaling reference set and included in the final scaled dataset if the merging statistics remained acceptable upon incorporation of the data. Each of the higher resolution datasets is exposed to a much larger dose of radiation resulting in a rapid decay in intensity. 10°-20° wedges are collected from each crystal or translation, 5°-7° of which expected to have a diffraction data to 2.4 Å. Based on the mean $F/\sigma(F)$ of reflections near the three crystallographic axes, the effective resolution can be calculated. The anisotropy results in the high merging R factors in the last few resolution shells despite the significant $I/\sigma(I)$ values. The anisotropy is either an inherent property of the crystals or the result of a preferential orientation of the crystals within the mounting loop. Thus, the higher resolution shells can be filled in anisotropically by incorporation of the additional data at high exposure levels, while the lower resolution shells have a very high redundancy and low anisotropy.

What is claimed is:

1. A fusion protein comprising, from N-terminus to C-terminus:
   a) a first portion of a G-protein coupled receptor (GPCR), wherein said first portion comprises the TM1, TM2 and TM3 regions of said GPCR;
   b) a stable, folded protein insertion , wherein said protein comprises a well-structured soluble domain which provides an amino and carboxyl termini that approximates the predicted distance between the cytoplasmic ends of TM3 and TM4 of said GPCR and which, when in crystalline form, aids in the formation of lattice contacts;
   c) a second portion of said GPCR, wherein said second portion comprises the TM4, TM5 TM6 and TM7 regions of said GPCR; and
   wherein said GPCR fusion protein is characterized in that it is crystallizable under lipid cubic phase or bicelle crystallization conditions.

2. The fusion protein of claim 1, wherein said GPCR is active.

3. The fusion protein of claim 1, wherein said GPCR is naturally occurring.

4. The fusion protein of claim 1, wherein said GPCR is non-naturally occurring.

5. The fusion protein of claim 1, wherein said stable, folded protein insertion element is a polypeptide that folds autonomously and is stable in its tertiary folded form.

6. The fusion protein of claim 1, wherein said stable, folded protein insertion comprises the amino acid sequence of lysozyme.

7. A composition a crystalline form of a fusion protein comprising, from N-terminus to C-terminus:
   a) a first portion of a G-protein coupled receptor (GPCR), wherein said first portion comprises the TM1, TM2 and TM3 regions of said GPCR;
   b) a stable, folded protein insertion , wherein said protein comprises a well-structured soluble domain which provides an amino and carboxyl termini that approximates the predicted distance between the cytoplasmic ends of helix III and helix IV of said GPCR and which, when in crystalline form, aids in the formation of lattice contacts; and
   c) a second portion of said GPCR, wherein said second portion comprises the TM4, TM5 TM6 and TM7 regions of said GPCR.

8. A method of crystallizing a fusion protein comprising contacting a fusion protein under lipid cubic phase or bicelle crystallization conditions which facilitates the growth of said fusion protein crystals, wherein said fusion protein is a fusion protein comprising, from N-terminus to C-terminus:
   a) a first portion of a G-protein coupled receptor (GPCR), wherein said first portion comprises the TM1, TM2 and TM3 regions of said GPCR;
   b) a stable, folded protein insertion , wherein said protein comprises a well-structured soluble domain which provides an amino and carboxyl termini that approximates the predicted distance between the cytoplasmic ends of helix III and helix IV of said GPCR and which, when in crystalline form, aids in the formation of lattice contacts; and
   c) a second portion of said GPCR, wherein said second portion comprises the TM4, TM5 TM6 and TM7 regions of said GPCR.

9. The method of claim 8, wherein said method comprises combining said fusion protein with lipid prior to crystallization.

10. The method of claim 8, further comprising:
    obtaining atomic coordinates of said fusion protein from said crystal.

11. A method of determining a crystal structure, comprising:
   receiving a fusion protein of claim 1, crystallizing said fusion protein to produce a crystal; and obtaining atomic coordinates of said fusion protein from said crystal.

12. A method of determining a three-dimensional atomic structure, comprising: forwarding a fusion protein of claim 1 to a remote location, and receiving atomic coordinates of said fusion protein.

13. The fusion protein of claim 1, wherein said GPCR is a family C GPCR.

14. The method of claim 8, wherein said GPCR is a family C GPCR.

15. The composition of claim 7, wherein said GPCR is a family C GPCR.

* * * * *